(12) United States Patent
Tracy et al.

(10) Patent No.: US 10,977,479 B2
(45) Date of Patent: Apr. 13, 2021

(54) TISSUE POTENCY DETERMINATION THROUGH QUANTITATIVE HISTOMORPHOLOGY ANALYSIS

(71) Applicant: Enzyvant Therapeutics, Inc., Cambridge, MA (US)

(72) Inventors: Alex Tracy, Apex, NC (US); Kristin Marks, Durham, NC (US); Michael Thomas Johnson, Bridgewater, NJ (US); Thomas Stephen Villani, Belle Mead, NJ (US)

(73) Assignee: ENZYVANT THERAPEUTICS GMBH, Basel (CH)

( * ) Notice: Subject to any disclaimer, the term of this patent is extended or adjusted under 35 U.S.C. 154(b) by 119 days.

(21) Appl. No.: 16/460,288

(22) Filed: Jul. 2, 2019

(65) Prior Publication Data
US 2020/0012845 A1    Jan. 9, 2020
US 2020/0285830 A9    Sep. 10, 2020

Related U.S. Application Data

(63) Continuation of application No. PCT/US2019/040275, filed on Jul. 2, 2019.
(Continued)

(51) Int. Cl.
*G06K 9/00* (2006.01)
*C12N 5/00* (2006.01)
(Continued)

(52) U.S. Cl.
CPC ....... *G06K 9/00147* (2013.01); *C12N 5/0018* (2013.01); *G01N 33/4833* (2013.01);
(Continued)

(58) Field of Classification Search
CPC .................................................. G06K 9/00147
See application file for complete search history.

(56) References Cited

U.S. PATENT DOCUMENTS 5,766,944 A     6/1998   Ruiz
2007/0264269 A1   11/2007  Harmon et al.
(Continued)

OTHER PUBLICATIONS

Markert ML et al., 2010, "Thymus transplantation," Clin Immunol., 135(2): 236-46.
(Continued)

*Primary Examiner* — Oneal R Mistry
(74) *Attorney, Agent, or Firm* — Raymond G. Arner; Pierce Atwood LLP

(57) ABSTRACT

Systems and methods for performing quantitative histopathology analysis for determining tissue potency are disclosed. According to some embodiments, a method training a tissue classifier is provided. According to the method, training the tissue classifier includes generating feature fingerprints of detected nuclei within slide images in a control library and clustering the slide images based on their corresponding feature fingerprints. According to some embodiments, a method for utilizing the trained tissue classifier is provided. According to the method, the trained tissue classifier determines whether tissue in an unknown slide image corresponds to slide images clustered during the training of the tissue classifier.

60 Claims, 61 Drawing Sheets
(33 of 61 Drawing Sheet(s) Filed in Color)

Related U.S. Application Data

(60) Provisional application No. 62/694,829, filed on Jul. 6, 2018.

(51) Int. Cl.
    *G01N 33/483*     (2006.01)
    *G06K 9/62*     (2006.01)
    *G06T 7/00*     (2017.01)

(52) U.S. Cl.
    CPC ......... *G06K 9/0014* (2013.01); *G06K 9/6218* (2013.01); *G06K 9/6256* (2013.01); *G06T 7/0012* (2013.01); *G06T 2207/20081* (2013.01); *G06T 2207/30024* (2013.01)

(56) References Cited

U.S. PATENT DOCUMENTS

| | | |
|---|---|---|
| 2010/0111396 A1 | 5/2010 | Boucheron |
| 2011/0008397 A1 | 1/2011 | Cohen |
| 2013/0089248 A1 | 4/2013 | Remiszewski et al. |
| 2015/0317537 A1* | 11/2015 | Jain .................. G06T 7/0012 382/128 |
| 2017/0103521 A1* | 4/2017 | Chukka .................. G06T 7/0012 |
| 2017/0145514 A1 | 5/2017 | Kennedy et al. |
| 2017/0323148 A1* | 11/2017 | Sarkar .................. G06K 9/00127 |
| 2017/0367580 A1 | 12/2017 | DiMaio et al. |
| 2017/0372117 A1 | 12/2017 | Bredno et al. |
| 2018/0204085 A1* | 7/2018 | Chennubhotla ........ G16H 30/40 |
| 2020/0258223 A1* | 8/2020 | Yip ....................... G06T 7/0012 |

OTHER PUBLICATIONS

Markert ML et al., 2004, "Postnatal thymus transplantation with immunosuppression as treatment for DiGeorge syndrome," Blood 104(8):2574-2581.

Markert ML et al., 1999, "Transplantation of thymus tissue in complete DiGeorge syndrome," N Engl J Med 341(16):1180-1189 27).

Markert ML et al., 2008, "Use of allograft biopsies to assess thymopoiesis after thymus transplantation," J Immunol 180(9):6354-6364.

Markert ML et al., 2007, "Review of 54 patients with complete DiGeorge anomaly enrolled in protocols for thymus transplantation: outcome of 44 consecutive transplants," Blood 109(10):4539-454728).

Chinn et al., 2008, "Long-term tolerance to allogeneic thymus transplants in complete DiGeorge anomaly," Clin Immunol 126(3):277-281 (8 pgs.).

Markert ML, 2014, Thymus Transplantation. Stiehm's Immune Deficiencies, eds Sullivan KE & Stiehm ER (Academic Pess), 1st Ed, pp. 1059-1067.

International Search Report and Written Opinion dated Oct. 1, 2019 in PCT/US2019/040275 (23 pages).

\* cited by examiner

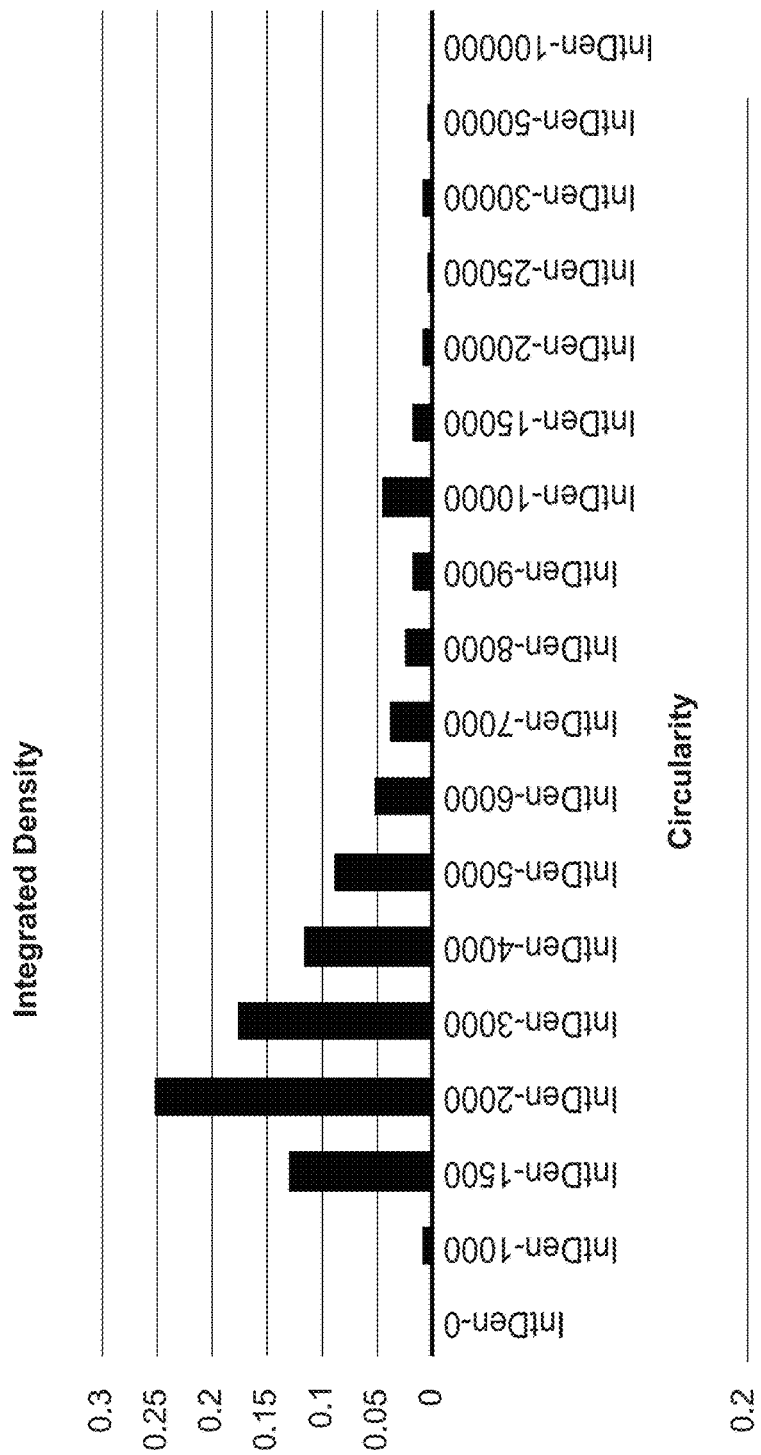
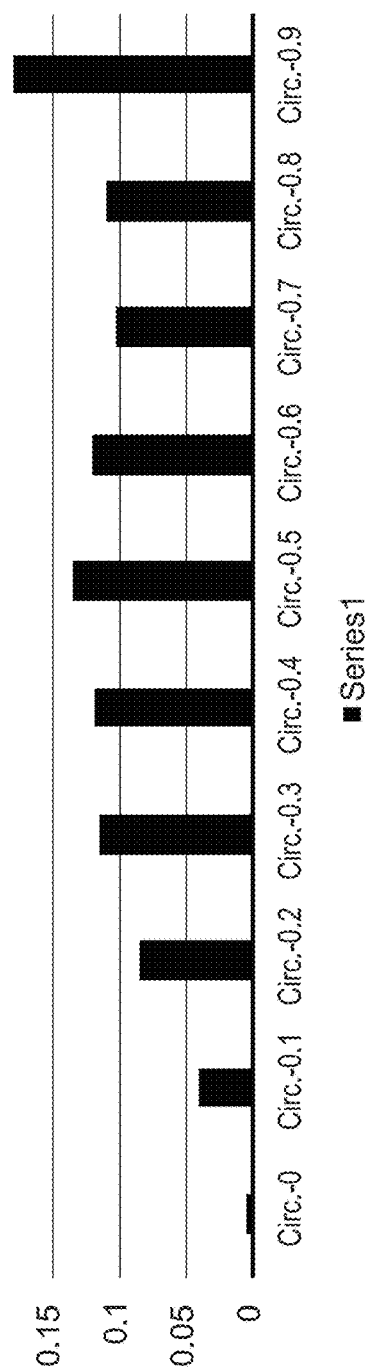
FIG. 6C
FIG. 6D

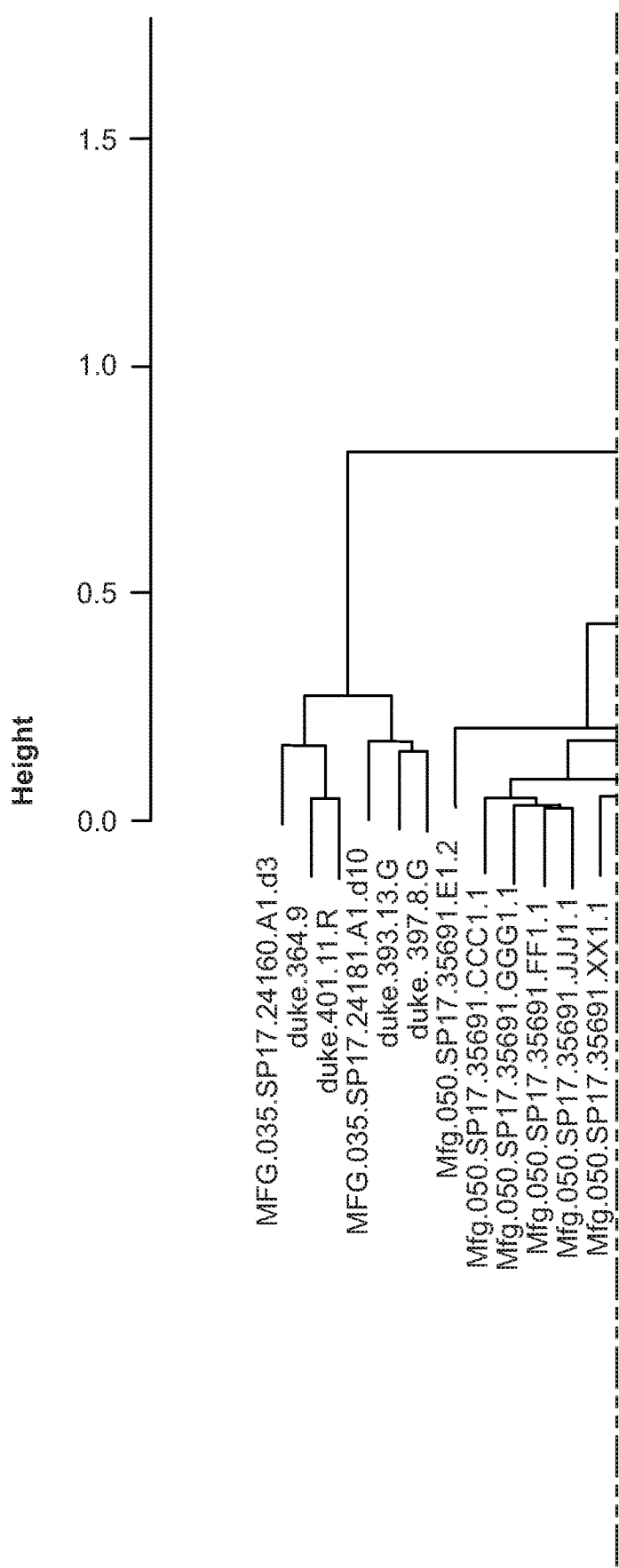

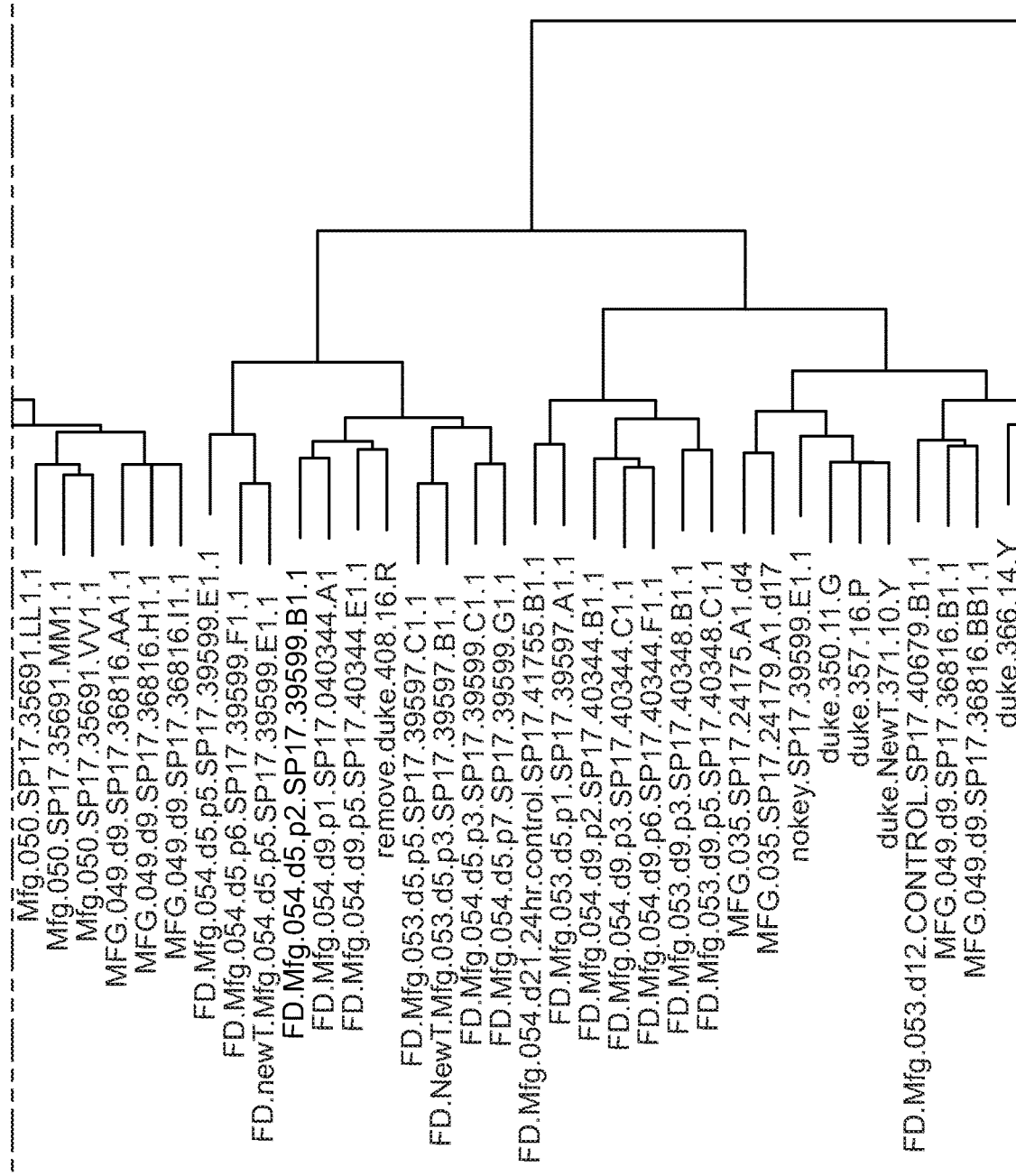

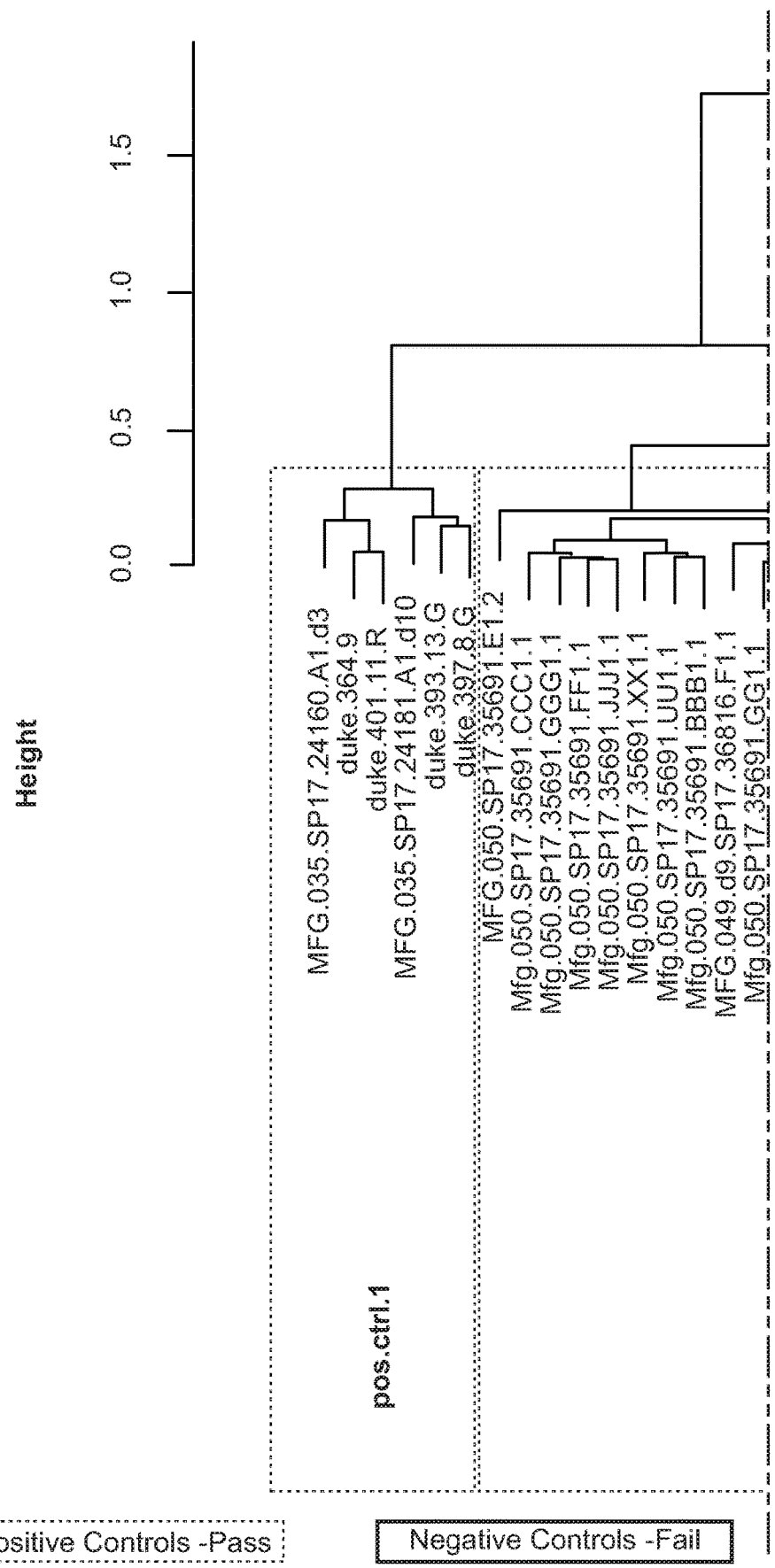

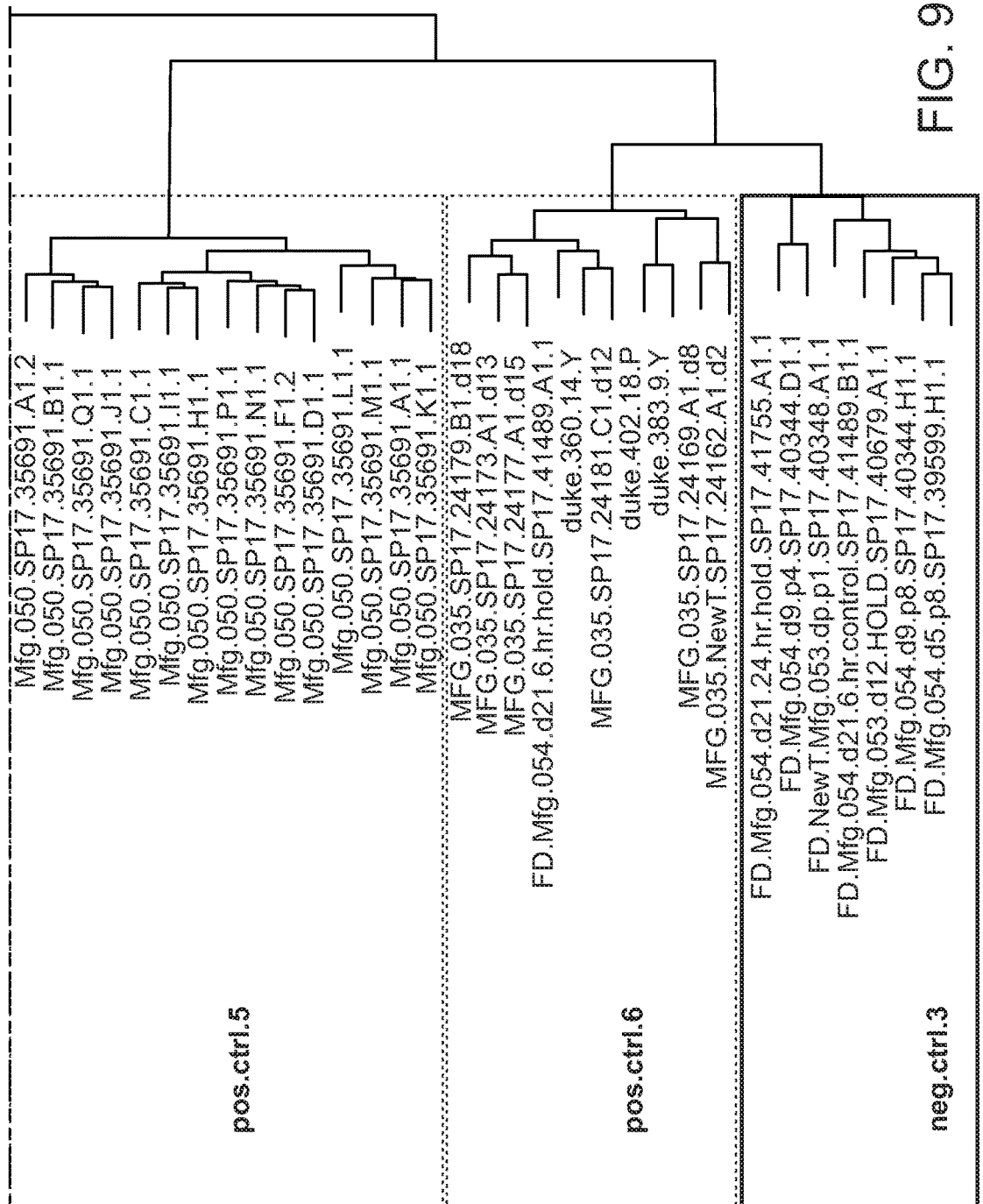

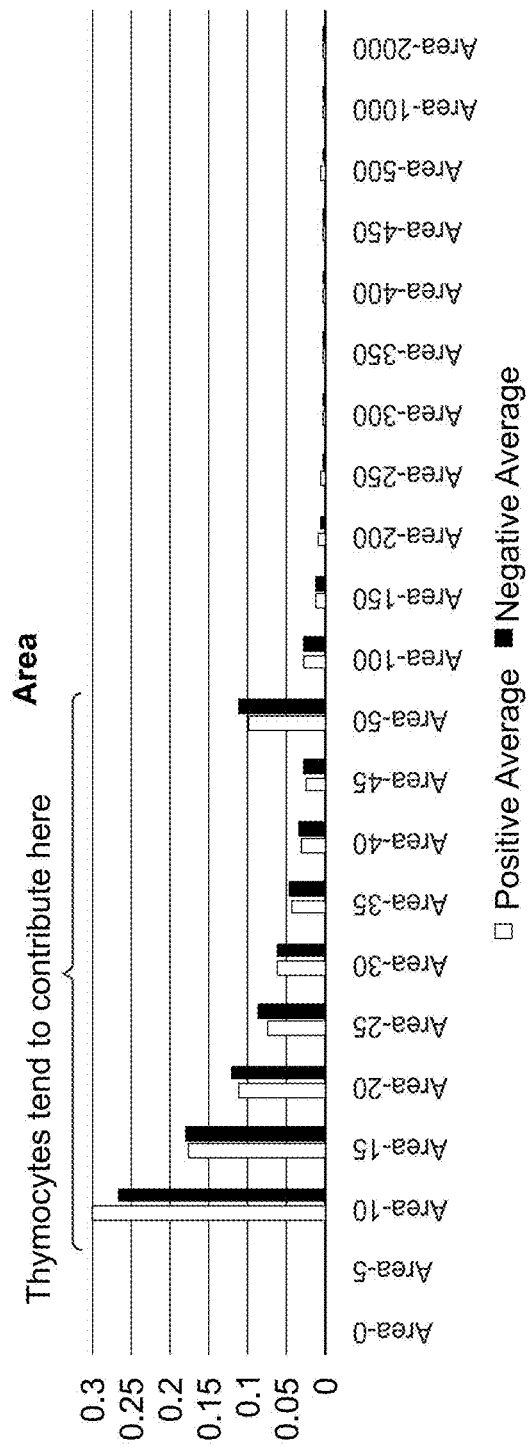
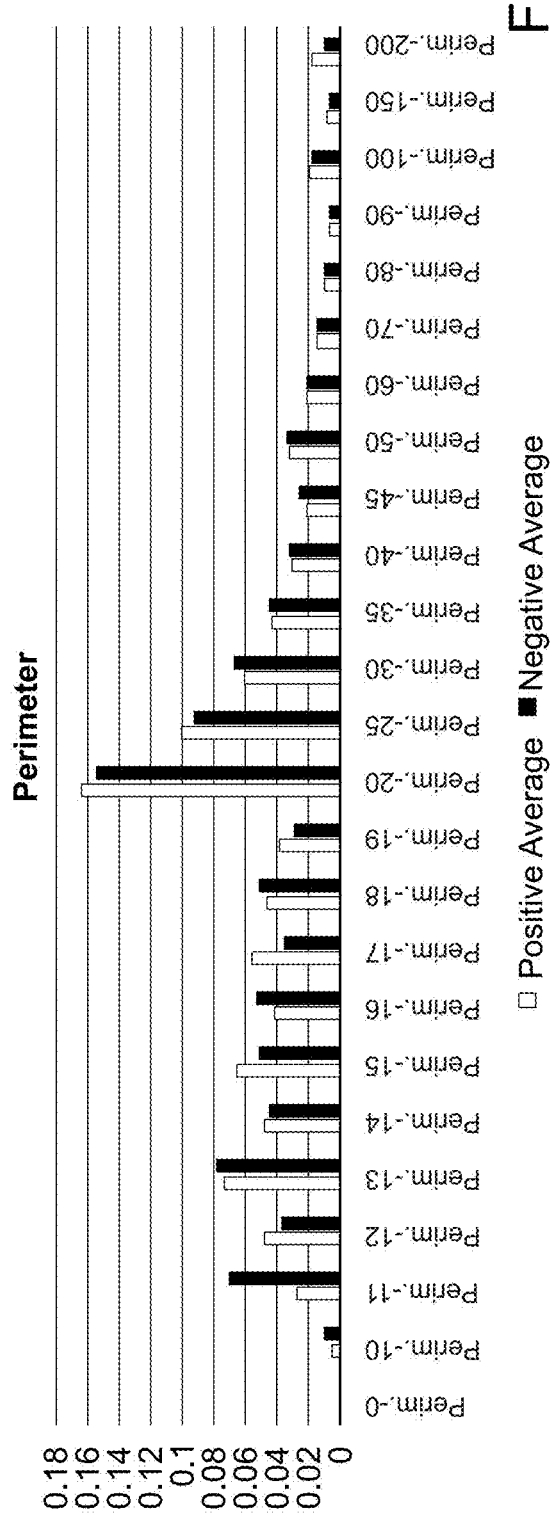

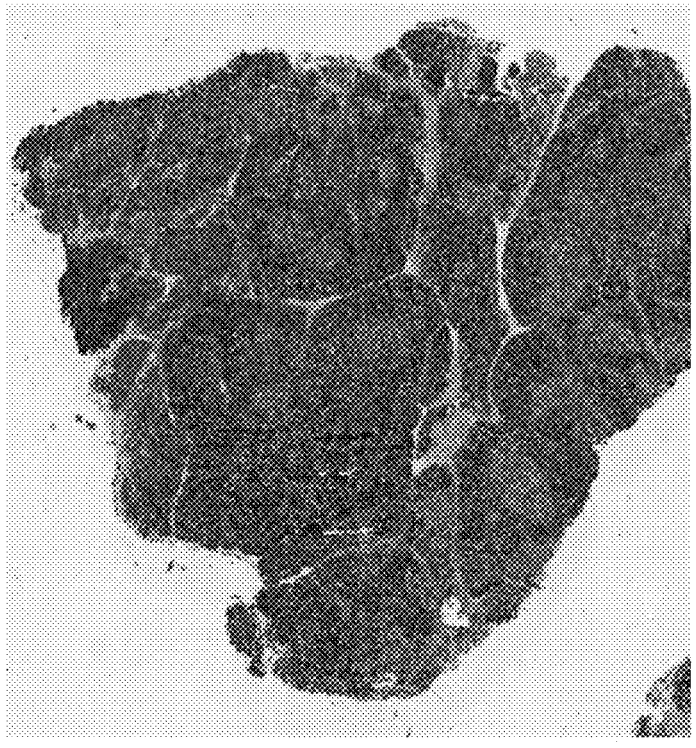
FIG. 13B Positive Control
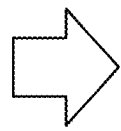
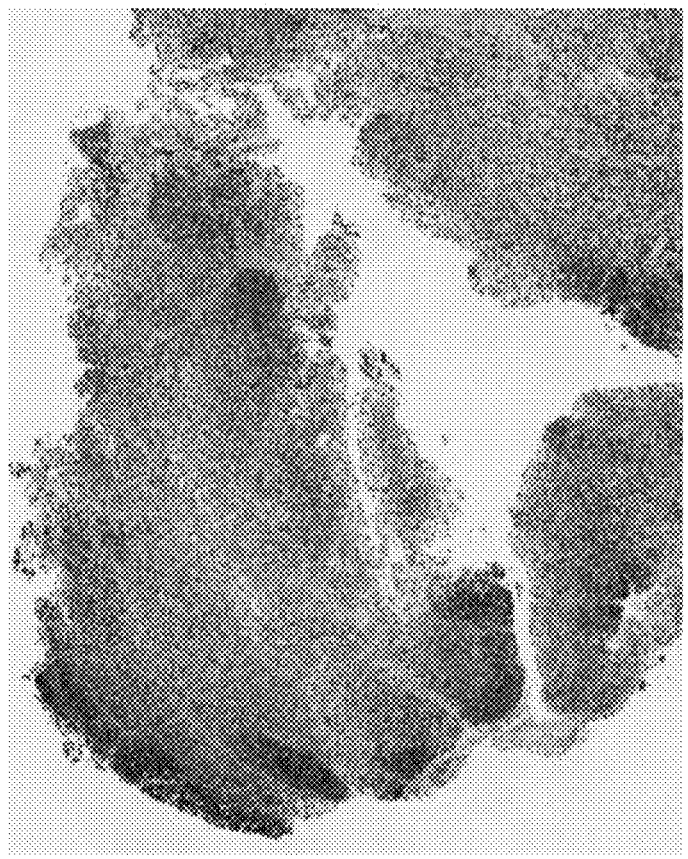
FIG. 13A Negative Control

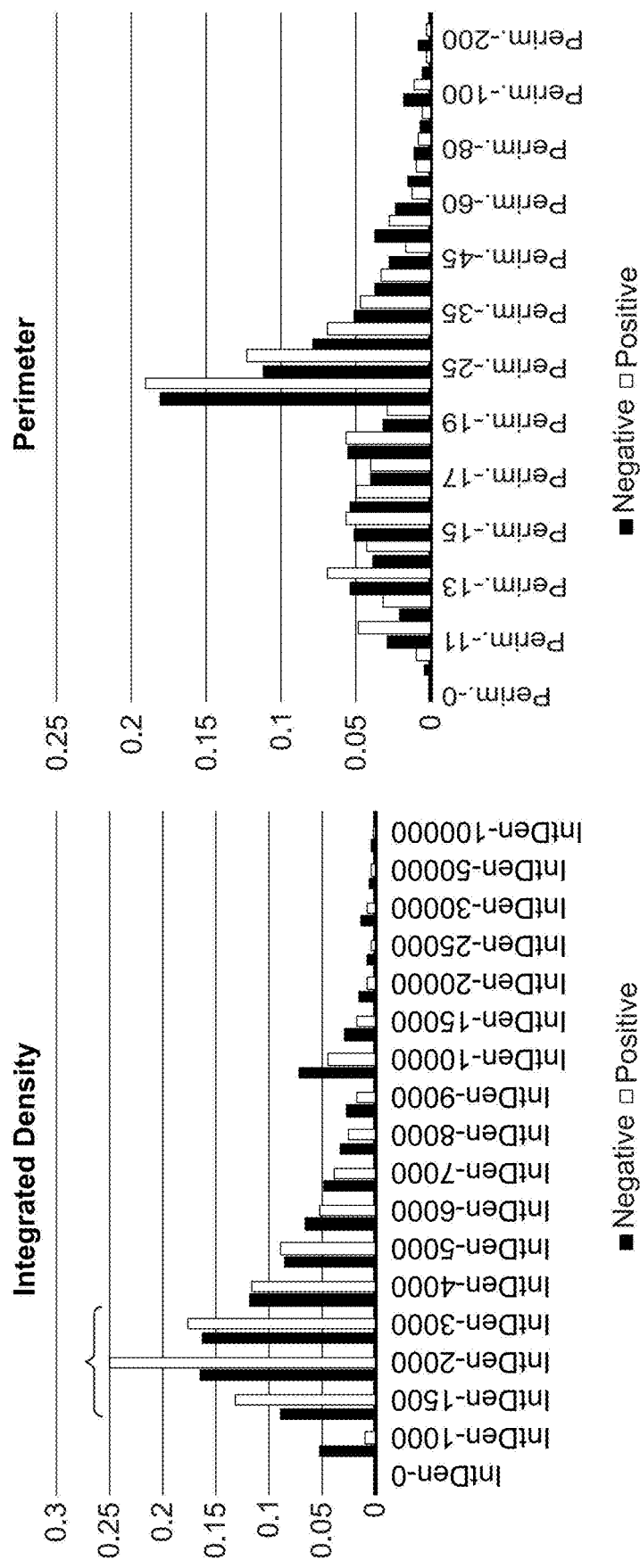

FIG. 35A   FIG. 35B   FIG. 35C
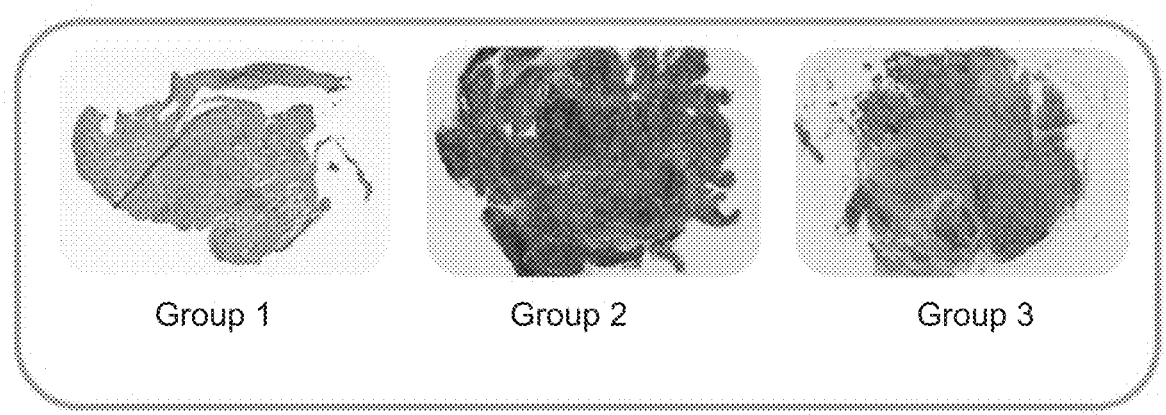
Group 1   Group 2   Group 3
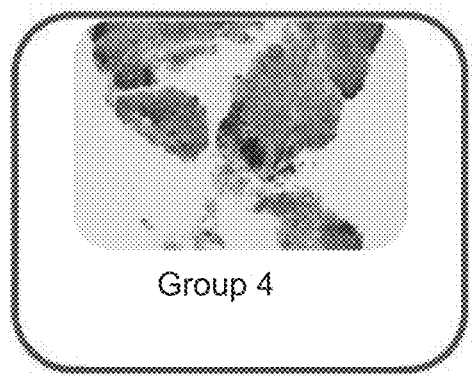
Group 4
FIG. 35D

TISSUE POTENCY DETERMINATION THROUGH QUANTITATIVE HISTOMORPHOLOGY ANALYSIS

CROSS REFERENCE TO RELATED APPLICATION

This application claims the benefit to and priority of U.S. Provisional Application No. 62/694,829, filed Jul. 6, 2018, and is a continuation application of PCT/US19/40275, filed Jul. 2, 2019, the subject matter of which is incorporated herein in its entirety by reference.

FIELD OF INVENTION

The described embodiments relate to a quantitative approach for performing quantitative histomorphology analysis of digital images of cells within a tissue sample for determining viable transplantation tissue candidates.

BACKGROUND OF THE INVENTION

The invention may be understood by reference to the preparation of allogeneic cultured postnatal thymus tissue-derived product, although this disclosure of and claims to the invention are not limited to such an embodiment of the invention.

Allogeneic cultured postnatal thymus tissue-derived product has been shown to be useful for the treatment of T cell immunodeficiency (primary immune deficiency) resulting from congenital athymia, for example in the treatment of complete DiGeorge Anomaly (cDGA) associated with 22q11.2 deletion and CHARGE (coloboma, heart defect, choanal atresia, growth or mental retardation, genital hypoplasia and ear anomalies or deafness) syndrome associated with mutations in the chd7 (chromodomain-helicase-DNA-binding protein 7) gene and in athymic patients with forkhead box protein N1 (FOXN1) deficiency. Congenital athymia is a rare fatal condition and currently has no drug treatment options utilizing regulatory approved drug products.

Experimental transplantation of an allogeneic cultured postnatal thymus tissue-derived product that retains thymus epithelial cells (TECs) has been successfully applied to treat pediatric patients with congenital athymia (Markert M L, Devlin B H, McCarthy E A, 2010, "Thymus transplantation," *Clin Immunol.*, 135(2): 236-46; Markert M L, et al., 2004, "Postnatal thymus transplantation with immunosuppression as treatment for DiGeorge syndrome," *Blood* 104 (8):2574-2581; Markert M L, et al., 1999, "Transplantation of thymus tissue in complete DiGeorge syndrome," *N Engl J Med* 341(16): 1180-1189 27).

Allogeneic cultured postnatal thymus tissue-derived product is a tissue-engineered product that is prepared, cultured and stored for up to 21 days to produce partially T cell-depleted thymus tissue slices and which is differentiated from native thymus by a conditioning process. The conditioning regimen partially depletes the donor thymocytes from the cultured thymus tissue slices. Based on in vitro data (immunohistochemistry) a culture period between 12 and 21 days preserves the epithelial network as assessed using cytokeratin antibodies. The culturing is preferably done at 37° C. in a 5% $CO_2$ incubator.

The culturing process significantly modifies the biological characteristics of the donor thymus tissue and constituent cells contained therein in the following manner to optimize the effective therapeutic properties of the Allogeneic cultured postnatal thymus tissue-derived product slices. The culturing process assures that a defined composition of the cultured cells/tissue having the pre-requisite biological characteristics is obtained in a manner suitable for surgical implantation into a subject to enable reconstitution of the subject's immune system. The culturing process results in a loss of thymocytes and relative enrichment of thymic epithelial cells and other stromal cells in the donor thymus tissue slices. The culturing process further results in depletion of thymocytes and maintenance of TECs to enable reconstitution of the recipient's immune system and allows tolerance to develop in the recipient to HLA antigens in the donor thymus. Overall, the manufacturing process is designed to deplete thymocytes from the donor thymus tissue and to preserve the functional architecture of the thymic stroma (thymic epithelial cells and fibroblasts).

The surgical administration of allogeneic, cultured postnatal thymus tissue-derived product (e.g., "RVT-802") in athymic patients leads to a cascade of events resulting in the development of a functional immune system. Following surgical placement of allogeneic, cultured postnatal thymus tissue-derived product in a recipient, T cells are educated by donor TECs and recipient dendritic cells (DCs). Donor TECs in conjunction with recipient DCs enable tolerance to the implanted donor thymus tissue, which is implanted as cultured thymus tissue slices. This is the same tolerance induction as in a normal thymus. The recipient TECs in conjunction with recipient DCs lead to tolerance to self.

Thymopoiesis has been documented by allograft biopsies and the presence of recipient naive T cells in the periphery (Markert M L, 2010; Markert M L, et al., 2008, "Use of allograft biopsies to assess thymopoiesis after thymus transplantation," J Immunol 180(9):6354-6364; Markert M L, et al., 2007, "Review of 54 patients with complete DiGeorge anomaly enrolled in protocols for thymus transplantation: outcome of 44 consecutive transplants," Blood 109(10): 4539-454728), which are incorporated herein by reference.

Studies of children treated with investigational allogeneic, cultured postnatal thymus tissue-derived product show tolerance to donor major histocompatibility complex (MHC) by mixed lymphocyte reactions (Chinn I K, Devlin B H, Li Y J, & Markert M L, 2008, "Long-term tolerance to allogeneic thymus transplants in complete DiGeorge anomaly," Clin Immunol 126(3):277-281). In addition, the infants with congenital athymia, after allogeneic, cultured postnatal thymus tissue-derived transplantation, are able to control infections such as Epstein Barr virus (Markert M L, 2014, Thymus Transplantation. Stiehm's Immune Deficiencies, eds Sullivan K E & Stiehm E R (Academic Press), 1st Ed, pp 1059-1067.

Historically, allogeneic cultured postnatal thymus tissue-derived product release criteria has included histopathological evaluation of H&E and immunostained sections of tissue at the mid-point of the manufacturing process, which was later refined to days 5-9 of the culture period. This histopathological evaluation has served as the potency assay, and has been performed as a qualitative analysis by a board-certified pathologist. Samples were prepared for evaluation either by freezing or formalin fixation prior to the tissue slice being sectioned and then fixed onto a slide. Samples prepared in this manner are stable over long periods of time, allowing for reanalysis to be performed.

The historical samples available from the 20+ years of development history can be linked to positive clinical outcomes, and thus provide a strong data set for development of a quantitative histology assay for evaluation of product quality.

A new digital histology assay was developed using scanned images of H&E slides from previous clinical lots and from experimental lots of allogeneic, cultured postnatal thymus-tissue derived product. These images were analyzed for development into a quantitative release assay, as described below.

SUMMARY OF THE INVENTION

The embodiments fully disclosed herein describe a method for quantitatively assessing the overall nuclear characteristics of a tissue represented within a slide image.

One application of the disclosed embodiments is the development, through training of a tissue classifier, of an assay that is capable of determining the potency or the quality of the tissue prior to transplantation into patients. For example, the approaches described below could be applied to determining potency of allogeneic cultured postnatal thymus tissue-derived product slices for complete DiGeorge Syndrome patients. The described embodiments can be utilized as an allogeneic cultured postnatal thymus tissue-derived product slices tissue characterization assay that evaluates thymus tissue potency based upon histological slide image analysis and associating passing tissues with a pass classification and failing tissues with a fail classification for potency. As shown in FIG. 1 below, a classifier receives, as input, an unclassified slide image and determines, based on an analysis of the unclassified slide image, whether the tissue in the unclassified slide image is a transplantation tissue candidate.

As will be discussed in additional detail below, the described embodiments describe a training phase that includes the training of the classifier based on a library of slide images and a classification phase that includes the utilization of the trained classifier on an unclassified slide image to determine the potency of the tissue represented in the unclassified slide image. The training phase trains the classifier through a quantitative assessment of nuclear characteristics that are associated with tissue composition and cell viability. The training phase includes analysis of both passing and failing slide images to train the classifier to recognize the corresponding nuclear characteristics in the passing and failing slide images. The resulting classifier implements an assay that recognizes passing and failing composition and viability characteristics based on the historical data that results in successful immune reconstitution following tissue implantation.

In an embodiment, the training phase includes two parts. The first part includes validation of a training dataset which is used to generate suitability criteria for appropriate metadata values, background values, and tissue entropy, and may define acceptable ranges or values that are considered to be acceptable for quantitative analysis. The training dataset includes slide images that are known to have a passing or failing classification for transplantation. These may be slide images that have been analyzed by a pathologist or other medical professional, for example. The second part includes applying the acceptable ranges or values generated in the first part to images within a control library, which results in clustering of the images into positive and negative control groups. As will be discussed further below in the specification and Examples, each control group includes slide images grouped based on having similar feature fingerprints. Positive control groups include slide images with similar feature fingerprints determined to pass the criteria for transplantation; negative control groups include slide images with similar feature fingerprints determined to fail the criteria for transplantation.

In an embodiment, the classification phase then analyzes new slide images based on the positive and negative control groups and clustering the new slide images based on the respective feature fingerprints. The classification phase then determines the potency of the new slide images based on the whether the new slide images are clustered with the positive or negative control groups.

In an embodiment, the feature fingerprints are based on four determinations of the cultured thymus cells. These include "area," "circularity," "integrated density," and "perimeter." As discussed below, "area" measures the nuclear area which is larger for thymic epithelial cells than for thymocytes. Cells undergoing apoptosis are also likely to be smaller. "Circularity" measures how circular the cells are. Circularity is measured on a scale of 0 to 1 with 1 being a perfect circle. Thymocytes have increased circularity compared to thymic epithelial cells. Non-viable cells have reduced circularity compared to viable cells. As such, circularity may be expected to decrease over culture time course, as both thymocytes are reduced and more non-viable cells can be expected to be observed in the tissue slices. Degraded samples are also expected to have decreased circularity as there would be more non-viable cells thereby shifting the distribution toward lower circularity. "Integrated Density" represents how dark a nucleus is stained. Integrated density is high for thymocytes, which shown uniformly dark staining. Thymic epithelial cells have dark-stained rims and mostly clear nucleoplasm with a prominent dark nucleolus. Finally, "Perimeter" represents the outline of the nuclei that are detected. The perimeter is related to cell viability; as cells degrade, the nuclear outline becomes irregular and its perimeter increases. Perimeter would also increase as the proportion of TEC cells to total cells increase as culture progresses. Perimeter changes are expected over time in culture as well as with degradation of tissue.

The described embodiments are an improvement over current approaches that rely solely on qualitative human-driven analysis, via immunohistochemistry (IHC) and hematoxylin and eosin (H&E) histopathology of slide images to determine potency. These current approaches suffer from a number of limitations that diminish the efficacy of the present qualitative analyses, including an inability to make such qualitative analyses either semi-quantitative or quantitative and that in the human assay, a pathologist cannot assess the entire tissue. Instead, the pathologist is looking at only a part of the tissue (an individual field of view) as opposed to the entire slice of tissue.

Moreover, the described embodiments are particularly more effective than conventional approaches for analyzing complex tissues, like the thymus. In complex tissues, the orientation of the sample tissue can markedly change outcome variations. For example, two separate slices with very different morphologies (e.g. corticomedullary ratio) could both be considered "good" samples (i.e., have a pass classification) with acceptable potency. The described embodiments avoid this limitation and, therefore, are effective in classifying all tissues.

The described embodiments rely on quantitative analysis by leveraging a library of slide images having known potency and efficacy. The slide images in the library include images of tissue that are known to have passed or failed the criteria for potency for that particular tissue by associating such tissues with good or poor clinical outcomes (e.g. survival or not). Slide images that have passed can be associated with a pass classification while slide images that have failed can be associated with a fail classification.

The described embodiments may be implemented on one or more processors. The one or more processors may be co-located or distributed over a network, such as a LAN, WAN, or the Internet (e.g., cloud). One or more of such processors may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc. The one or more processors may be coupled to a memory that includes one or more levels of cache, and which may have control logic (e.g., computer software) and/or data stored therein.

A first aspect of the present disclosure provides a method of training a tissue classifier for performing quantitative histopathological assessment, comprising:

converting a slide image into a binary slide image, wherein the slide image is selected from a library of control images, wherein each slide image in the library of control images is associated with a pass classification or a fail classification;

detecting one or more nuclei within the binary slide image;

for each detected nucleus, extracting a feature from the detected nucleus, wherein the feature represents a property of the detected nucleus within the binary slide image and comprises at least one of an area of the detected nucleus, a perimeter of the detected nucleus, an integrated density of the detected nucleus, or a circularity of the detected nucleus;

for each detected nucleus, generating, based on the feature, a feature fingerprint associated with the binary slide image, wherein the feature fingerprint is a numerical value calculated from processing the feature;

incorporating the binary slide image into a cluster wherein the cluster comprises a plurality of images, wherein each of the first plurality of images is associated with a corresponding feature fingerprint, and wherein the incorporating is based on comparing the feature fingerprint with the corresponding feature fingerprint;

applying a cutoff height to the cluster to form a plurality of groups, wherein the cutoff height minimizes a number of groups within the plurality of groups based on multivariate analysis of variance analysis of the cluster;

categorizing a first group within the plurality of groups as a positive control set if the first group comprises first slide images associated with the pass classification; and categorizing a second group within the plurality of groups as a negative control set if the second group comprises second slide images associated with the fail classification.

A second aspect of the present disclosure is a method for performing a quantitative histopathological assessment of an unclassified slide image of a tissue, comprising: detecting a hematoxylin channel from the unclassified slide image, wherein the hematoxylin channel is associated with a cellular nucleus within the unclassified slide image of a tissue;

extracting a feature from the detected hematoxylin channel, wherein the feature represents a property of the nucleus within the binary slide image and comprises at least one of an area of the nucleus, a perimeter of the nucleus, an integrated density of the nucleus, or a circularity of the nucleus;

generating, based on the feature, a feature fingerprint associated with the unclassified slide image, wherein the feature fingerprint is a numerical value calculated from processing the feature;

co-clustering the feature fingerprint with a first set of fingerprints associated with one or more positive control sets and a second set of fingerprints associated with a negative control set, wherein the positive control set(s) comprises a first set of slide images associated with a pass classification and the negative control set comprises a second set of slide images associated with a fail classification; and determining, based on the co-clustering, if the feature fingerprint is associated with the pass classification or the fail classification.

A third aspect of the present disclosure is a system for classifying objects within digital images of tissue, comprising:

means for converting a slide image into a binary slide image, wherein the slide image is selected from a library of control images, wherein each slide image in the library of control images is associated with a pass classification or a fail classification;

means for detecting a nucleus within the binary slide image;

means for extracting a feature from the detected nucleus, wherein the feature represents a property of the detected nucleus within the binary slide image and comprises at least one of an area of the detected nucleus, a perimeter of the detected nucleus, an integrated density of the detected nucleus, or a circularity of the detected nucleus;

means for generating, based on the feature, a feature fingerprint associated with the binary slide image, wherein the feature fingerprint is a numerical value calculated from processing the feature;

means for incorporating the binary slide image into a cluster wherein the cluster comprises a plurality of images, wherein each of the first plurality of images is associated with a corresponding feature fingerprint, and wherein the incorporating is based on comparing the feature fingerprint with the corresponding feature fingerprint;

means for applying a cutoff height to the cluster to form a plurality of groups, wherein the cutoff height minimizes a number of groups within the plurality of groups based on multivariate analysis of variance analysis of the cluster;

means for categorizing a first group within the plurality of groups as a positive control set if the first group comprises first slide images associated with the pass classification; and means for categorizing a second group within the plurality of groups as a negative control set if the second group comprises second slide images associated with the fail classification.

A fourth aspect of the present disclosure is a classifier, comprising:

means for detecting a hematoxylin channel from the unclassified slide image, wherein the hematoxylin channel is associated with a cellular nucleus within the unclassified slide image of a tissue;

means for extracting a feature from the detected hematoxylin channel, wherein the feature represents a property of the nucleus within the binary slide image and comprises at least one of an area of the nucleus, a perimeter of the nucleus, an integrated density of the nucleus, or a circularity of the nucleus;

means for generating, based on the feature, a feature fingerprint associated with the unclassified slide image, wherein the feature fingerprint is a numerical value calculated from processing the feature;

means for co-clustering the feature fingerprint with a first set of fingerprints associated with a positive control set and a second set of fingerprints associated with a negative control set, wherein the positive control set comprises a first set of slide images associated with a pass classification and the negative control set comprises a second set of slide images associated with a fail classification; and means for determining, based on the co-clustering, if the feature fingerprint is associated with the pass classification or the fail classification.

In certain embodiments of the first to fourth aspects of the present disclosure, the methods, system and classifier may comprise a tissue classifier or use of a tissue classifier capable of determining potency or the transplantability of a tissue of a subject, preferably a human subject.

In certain embodiments of the first to fourth aspects of the present disclosure, the tissue is a thymus tissue, preferably allogeneic cultured postnatal thymus tissue-derived product slices for implantation into a human subject.

In certain embodiments of the first to fourth aspects of the present disclosure, the human may be suffering from complete DiGeorge syndrome associated with 22q11.2 deletion; coloboma, heart defect, choanal atresia, growth or mental retardation, genital hypoplasia and ear anomalies or deafness syndrome (CHARGE), or athymia associated with forkhead box protein N1 (FOXN1) deficiency.

In certain embodiments of the first to fourth aspects of the present disclosure, the tissue classifier determines potency of an unknown tissue by generating feature fingerprints of detected nuclei within slide images in a control library and clustering the slide images based on their corresponding feature fingerprints, preferably a thymus tissue.

In certain embodiments of the first to fourth aspects of the present disclosure, the thymus tissue has been subjected to a culturing process in a thymus organ medium for a period of time to partially deplete the thymus tissue of thymocytes. In some embodiments, the period of time is up to 21 days. In other embodiments, the period of time is from about 12 to about 21 day, or from about 5 to about 9 days.

In certain embodiments of the first to the fourth aspects of the present disclosure, the culturing process preserves the functional architecture of the thymic stroma, preferably the thymic stroma comprises thymic epithelial cells and fibroblasts.

In certain embodiments of the first to the fourth aspects of the present disclosure, the tissue is selected from the group consisting of vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

In certain embodiments of the first to fourth aspects of the present disclosure, the feature fingerprint is generated from measurements comprising numerical values of an area of the detected nucleus, a perimeter of the detected nucleus, an integrated density of the detected nucleus, and a circularity of the detected nucleus.

It is further appreciated that certain features described herein, which are, for clarity, described in the context of different aspects of the present disclosure and/or in separate embodiments, can also be provided in combination in a single embodiment. Conversely, various features which are, for brevity, described in the context of a single aspect of the present disclosure and/or in a single embodiment, can also be provided separately or in any suitable subcombination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the principles disclosed herein, and the advantages thereof, reference is made to the following descriptions taken in conjunction with the accompanying drawings, in which:

FIG. 3A depicts a slide image showing a tissue sample on an appropriate amount of background pixels. FIGS. 3B and 3C illustrate slide images with too many background pixels. FIG. 3D illustrates a slide image with an insufficient number of background pixels.

FIG. 4A illustrates a slide image with correctly segmented nuclei while FIGS. 4B and 4C illustrate slide images with incorrectly segmented nuclei.

FIG. 5 depicts a hematoxylin stained thymus tissue specimen, which identifies a field for analysis as outline in the box, which is magnified in the middle image, and converted to a red channel of the slide image, which has been extracted and inverted to form the binary image, in the image on the right.

FIGS. 6A-6D illustrate exemplary results of feature extraction in an embodiment where the tissue is thymus tissue and the extracted features include area, perimeter, integrated density, and circularity. FIG. 6A illustrates area determinations. FIG. 6B illustrates perimeter determinations. FIG. 6C illustrates integrated density determinations. FIG. 6D illustrates circularity determinations.

FIG. 10 shows that the population of slide images within each group did not vary significantly, which indicates that those slide images share similar feature fingerprints.

FIGS. 12A-12D are prophetic examples that show example feature fingerprints based on certain extracted features of a slide image of thymus tissue. FIG. 12A illustrates a difference between slide images associated with positive and negative control groups in feature fingerprints generated for the area of the nuclei. FIG. 12B illustrates a difference between slide images associated with positive and negative control groups in feature fingerprints generated for the perimeter of the nuclei. FIG. 12C illustrates a difference between slide images associated with positive and negative control groups in feature fingerprints generated for the integrated density of the nuclei. FIG. 12D illustrates a difference between slide images associated with positive and negative control groups in feature fingerprints generated for the circularity of the nuclei.

FIGS. 13A-13F illustrates feature fingerprints from an exemplary application of the classifier to an example slide image of cortical thymocytes with a positive and a negative control group. FIG. 13A is an exemplary slide image of thymus tissue associated with a positive control group. FIG. 13B is an exemplary slide image of thymus tissue associated with a negative control group. FIG. 13C illustrates feature fingerprints associated with circularity determinations. FIG. 13D illustrates feature fingerprints associated with area determinations. FIG. 13E illustrates feature fingerprints associated with integrated density determinations. FIG. 13F illustrates feature fingerprints associated with perimeter determinations.

FIGS. 14A-14C are representative of three batches of cultured thymus clinical tissue samples. FIG. 14D is representative of degraded thymus tissue.

FIG. 16A is a photograph of the cultured H&E stained thymus tissue at Day 0. FIG. 16B is a close-up magnification of a portion of the cultured H&E stained thymus tissue at 40× magnification.

FIG. 17A is a photograph of the cultured H&E stained thymus tissue at Day 5. FIG. 17B is a close-up magnification of a portion of the cultured H&E stained thymus tissue at 40× magnification.

FIG. 18A is a photograph of the cultured H&E stained thymus tissue at Day 9. FIG. 18B is a close-up magnification of a portion of the cultured H&E stained thymus tissue at 40× magnification.

FIG. 19A is a photograph of the cultured H&E stained thymus tissue at Day 12. FIG. 19B is a close-up magnification of a portion of the cultured H&E stained thymus tissue at 40× magnification.

FIG. 20A is a photograph of the cultured H&E stained thymus tissue at Day 21. FIG. 20B is a close-up magnification of a portion of the cultured H&E stained thymus tissue at 40× magnification.

FIG. 21A shows a high proportion of the nuclei have a higher integrated density indicative of a high number of thymocytes. As thymocytes are washed out of the tissue, the tissue at Day 5 (FIG. 21B), 9 (FIG. 21C), 12 (FIG. 21D) and 21 (FIG. 21E) show a marked decrease in integrated density and a profile more similar to the profile for thymic epithelial cells.

FIGS. 35A-35D depict representative images for each cluster group in final sample library. Groups 1 (FIG. 35A), 2 (FIG. 35B), and 3 (FIG. 35C) are comprised of samples with positive clinical outcomes. Group 4 (FIG. 35D) is comprised of confirmed degraded samples. Group 1 sample is from LOT-345, Group 2 sample is from LOT-160, Group 3 sample is from LOT-194, and Group 4 sample is from FD.SP17-40348-C1.1 (method of degradation: Freezing at −20° C.).

FIG. 36A is a graphical representation of clusters of data on area determinations. FIG. 36B is a graphical representation of clusters of data on circularity determinations. FIG. 36C is a graphical representation of clusters of data on integrated density determinations. FIG. 36D is a graphical representation of clusters of data on perimeter determinations.

DETAILED DESCRIPTION OF THE INVENTION

Figure 1:
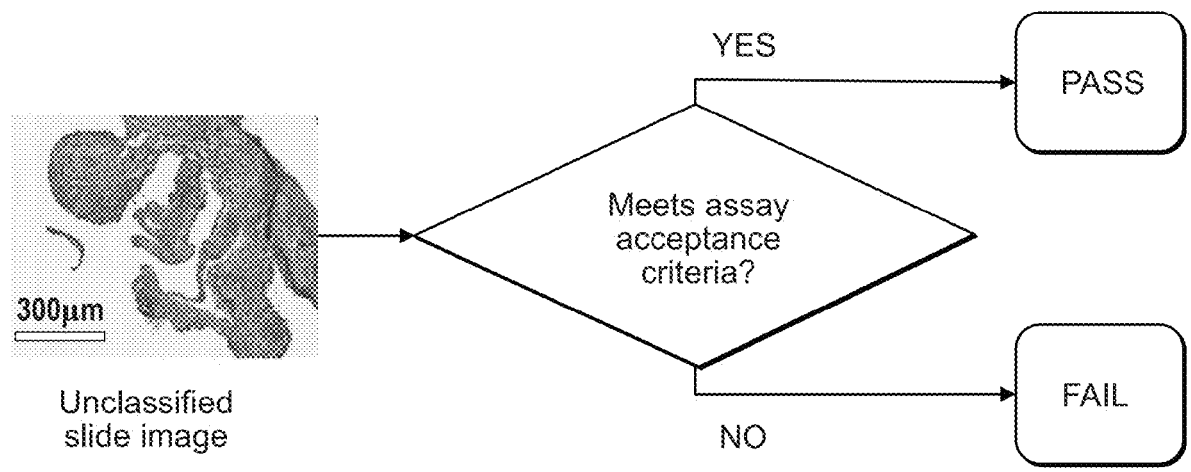
FIG. 1 is a schematic of the operation of a classifier that receives an input of an unclassified slide image and determines, based on an analysis of the unclassified slide image and a comparison to pre-established acceptance criteria, whether the tissue in the unclassified slide image is a transplantation tissue candidate.

The titles, headings and subheadings provided herein should not be interpreted as limiting the various aspects of the disclosure. Accordingly, the terms defined below are more fully defined by reference to the specification in its entirety. All references cited herein are incorporated by reference in their entirety.

Unless otherwise defined, scientific and technical terms used herein shall have the meanings that are commonly understood by those of ordinary skill in the art. Further, unless otherwise required by context, singular terms shall include pluralities and plural terms shall include the singular. In this application, the use of "or" means "and/or" unless stated otherwise. In the context of a multiple dependent claim, the use of "or" refers back to more than one preceding independent or dependent claim in the alternative only.

It is further noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The instant invention is most clearly understood with reference to the following definitions.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of +/−10%. As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps. Additionally, a term that is used in conjunction with the term "comprising" is also understood to be able to be used in conjunction with the term "consisting of" or "consisting essentially of."

The term "tissue" as used herein refers to any type of tissue in human or animals, and includes, but is not limited to, vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

As described herein, any concentration range, percentage range, ratio range or integer range is to be understood to include the value of any integer within the recited range and, when appropriate, fractions thereof (such as one tenth and one hundredth of an integer), unless otherwise indicated. Ranges are approximate and may vary by more than an integer.

Units, prefixes, and symbols are denoted in their Systeme International de Unites (SI) accepted form. Numeric ranges are inclusive of the numbers defining the range. Measured values are understood to be approximate, taking into account significant digits and the error associated with the measurement.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

"Area"—is reported in $\mu m^2$. The nuclear area is larger for thymic epithelial cells than for thymocytes. Cells undergoing apoptosis are also likely to be smaller.

"Circularity"—is a measure of how circular the cells are. Circularity is measured on a scale of 0 to 1 with 1 being a perfect circle. Thymocytes have increased circularity compared to thymic epithelial cells. Non-viable cells have reduced circularity compared to viable cells. As such, circularity may be expected to decrease over culture time course, as both thymocytes are reduced and more non-viable cells can be expected to be observed in the tissue slices. Degraded samples are also expected to have decreased circularity as there would be more non-viable cells thereby shifting the distribution toward lower circularity.

"Integrated Density"—represents how dark a nucleus is stained. Integrated density is high for thymocytes which show uniformly dark staining. Thymic epithelial cells have dark-stained rims ad mostly clear nucleoplasm with a prominent dark nucleolus.

"Perimeter"—represents the outline of the nuclei that are detected and is reported in $\mu m$. The perimeter is related to cell viability; as cells degrade, the nuclear outline becomes irregular and its perimeter increases. Perimeter would also increase as the proportion of TE cells to total cells increase as culture progresses. Perimeter changes are expected over time in culture as well as with degradation of tissue.

Overview of the Quantitative Histology Method

The quantitative histology method developed is an image based algorithm that clusters like images based on properties that were determined to have statistical and biological relevance to allogeneic cultured postnatal thymus tissue-derived product. Scanned H&E histology slides are created. The slide is uploaded into the validated thymus tissue analysis software as either an SCN or TIFF image. If the file uploaded is a SCN image, the algorithm will convert it into a TIFF image for analysis. The red channel of the image is extracted and then inverted such that the nuclei that are highlighted with the eosin stain are now black shapes on a white background.

The area, perimeter, integrated density (how dark the shape is), and circularity are then measured for each nuclei. The frequency distributions for each of these attributes are then able to be compared to known good and bad samples in a database. A statistical clustering comparison is then performed for the attributes to determine if the new input sample is statistically similar to the known samples and thus can be determined as "passing" or "failing" per previously identified criteria.

A selection of clinical and R&D H&E slides of allogeneic cultured postnatal thymus tissue-derived product were scanned at 40× or 20× magnification. The images were then uploaded for development of a quantitative histology method.

Figure 5:
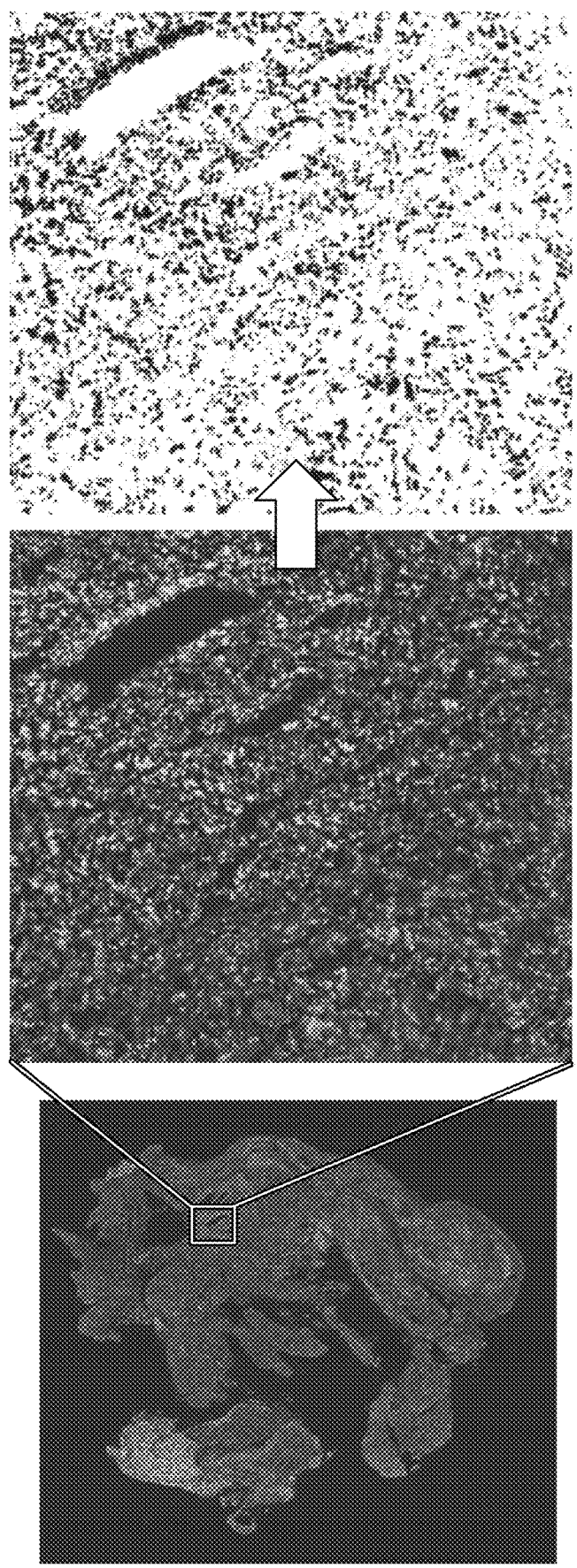
FIG. 5 depicts the image processing steps of analyzing the hematoxylin image of a thymus tissue specimen.

To quantify the slides, the images were first analyzed such that attribute data could be extracted from the images. To achieve this, the images were converted into the TIFF FGP format and then processed by an image processing algorithm through ImageJ where the images were calibrated to 1 $\mu m$/pixel, the red channel is extracted, and then the red channel is inverted such that the darker stained nuclei result in higher pixel intensity. Refer to FIGS. 5A-C for a depiction of this analysis.

Thresholds were determined and set to appropriate values for selection of nuclei to ensure image analysis is consistent from image to image. Images were analyzed for particles (cell nuclei), here defined as contiguous regions of pixels, exceeding 10 $\mu m^2$ in area. Parameters were then extracted for each particle including area, perimeter, width etc. (refer to Table 1 for full list of parameters evaluated).

Features that were determined to be of statistical significance through principle component analysis in the tissue population initially analyzed were area, perimeter, integrated density, and circularity. Other features were found incapable in aiding to distinguish between samples and were subsequently no longer analyzed.

FIGS. 14A-14D depict three batches of clinical cultured thymus tissue samples (FIGS. 14A-14C) and a degraded thymus tissue sample. The four features of area, perimeter, integrated density, and circularity for the sample depicted in FIG. 14A were: area=11.34; circularity=0.696; perimeter=14.310 and integrated density=1889.2. The four features of area, perimeter, integrated density, and circularity for the sample depicted in FIG. 14B were: area=11.41; circularity=0.993; perimeter=11.982 and integrated density=1912.4. The four features of area, perimeter, integrated density, and circularity for the sample depicted in FIG. 14C were: area=10.53; circularity=0.846; perimeter=12.510 and integrated density=1707.4. The four features of area, perimeter, integrated density, and circularity for the sample depicted in FIG. 14D were: area=13.0; circularity=0.352; perimeter=21.556 and integrated density=1786.0. A single nuclei in each image is identified by a circle.

Once the four parameters have been recorded for each nuclei, a frequency distribution is created for each parameter to show the distribution of nuclei over the entire slide. There are generally more than 100,000 data points for each slide. The bin width and cut-off for each parameter within a distribution were determined by selecting the fewest bins that still showed variability between the slides. The proportion of nuclei in each bin is determined and those values are used for the clustering analysis.

Overview of Quantitative Analysis and Clustering

The quantitative analysis described herein is an unbiased/emergent approach to digital pathology. Both the training phase and the classification phase include computerized feature extraction to generate a feature fingerprint for each image. In an embodiment, the feature fingerprint represents the underlying nuclear features of each image. Utilization of cellular feature extraction enables quantitative characterization of the underlying cell population within the tissue that represented in each slide image. Both phases also include a statistical hierarchical agglomerative clustering technique to classify histology sections by quantitative features describing each cell within a slide image. The clustering analysis categorizes the slide images into different groups based on similarities between the fingerprints generated for each slide image. In an embodiment, hierarchical agglomerative clustering is used within the context of image analysis for both training a tissue classifier and utilizing the trained tissue classifier for determining potency of unknown tissue. Examples of clustering embodiments of the disclosure are set forth below in the specification, Figures and Examples. For example, and not by way of limitation, the clustering techniques described in connection with FIGS. 2, 7-9, 32 et seq. and the accompanying text and Tables.

Hierarchical agglomerative clustering, in the context of tissue classification, includes assembling clusters directly from data in order to reveal emergent properties of the underlying dataset. In the classification phase, according to an embodiment, the clustering technique allows for classification of unknown tissue based on the similarity of generated feature fingerprints of the unknown tissue to previously clustered feature fingerprints of known tissue (e.g., from a library of slide images). The clustering technique also relies on analysis of the relative height of a cluster dendrogram (see FIG. 2) which indicates a distance between cluster center points. The relative height is typically proportionate to the difference between numerical features of clusters (discussed further below).

Figure 2:
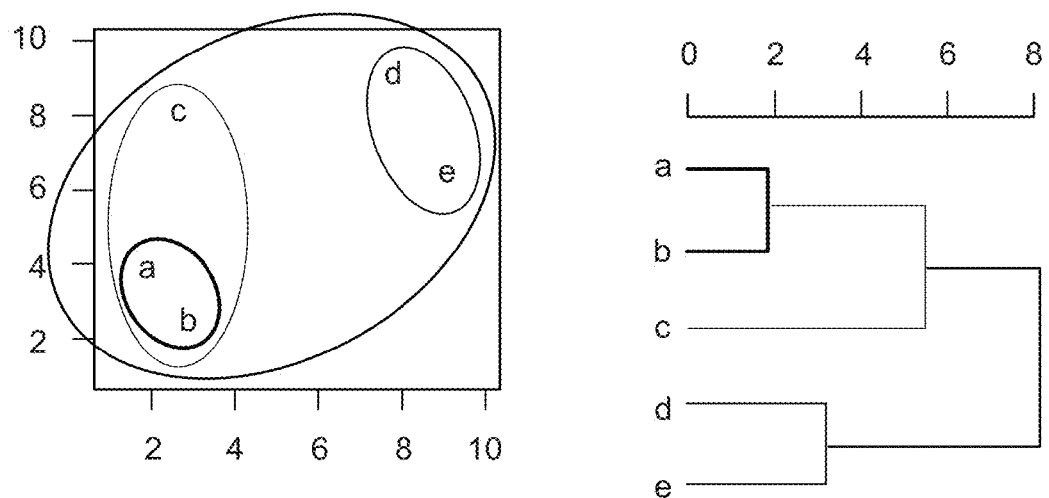
FIG. 2 shows an exemplary cluster and cluster dendrogram where the cluster has been segregated into different groups a, b, c, d and e.

FIG. 2 shows an exemplary cluster and cluster dendrogram where the cluster has been segregated into different groups a, b, c, d and e. After generation of the cluster and/or cluster dendrogram, statistical analysis techniques may be applied to determine the groups that differ from each other statistically significantly. One example of a statistical analysis technique is multivariate analysis of variance, or MANOVA, which is a procedure for determining variance between datasets having two or more (i.e., multiple) variables.

The training and classification phase may include one or more of the following steps: suitability determination, image processing, feature extraction, and clustering.

Suitability Determination

Suitability determination refers to assessing a slide image's characteristics to determine whether the slide image is suitable for further quantitative analysis as described in the disclosed embodiments. Suitability determination may be performed both for a training set of images as well as for new slide images. In an embodiment, suitability determination of a slide image includes metadata analysis, background pixel analysis (e.g., examination of the amount of background pixels present in the slide image), and tissue entropy (and nuclei segmentation) analysis (e.g., examination of the amount of entropy in the slide image).

Metadata Analysis

Metadata analysis of slide images determines whether a slide image has the appropriate metadata properties for the quantitative analysis. Examples of metadata that may be considered include but are not limited to: filename (e.g., whether the filename is unique), last modified date (date the file was last modified), file size (e.g., the size of the file in bytes), format (e.g., the file type such as TIF), image width (e.g., a value containing the width of the slide image in pixels), image height (e.g., a value containing the height of the slide image in pixels), bit depth (total number of bits for color channels in the slide image), color type (color type of the image, e.g., RGB), x-resolution (e.g., a value representing the resolution of the slide image in the X-direction), y-resolution (e.g., a value representing the resolution of the slide image in the Y direction), resolution units (e.g., a string containing the units of the x-resolution and y-resolution properties), image background ratio (ratio of the amount of background pixels to the total number of pixels), background label (label describing the amount of background pixels in the image), tissue entropy (entropy describing only the issue pixels segmented), and nuclei segmentation label (label describing the success of the nuclei segmentation analysis).

In an embodiment, a slide image may be considered suitable for quantitative analysis based on an analysis of one or more metadata properties described above. For example, in an embodiment, if all the above fields are present and readable within the header of the slide image, and the slide image has an x-resolution between 0.8 µm-1.2 µm and a y-resolution between 0.8 µm-1.2 µm, then slide image is suitable for quantitative analysis. In another embodiment, if any fields are missing or corrupted, the slide image may be excluded from quantitative analysis.

Background Analysis

Analysis of background pixels is a step to ensure that the image of the tissue is suitable for further analysis that requires a view of the tissue to be analyzed on a background. In an embodiment, quantitative analysis utilizes a standardized amount of background pixels in a slide image to ensure accurate segmentation takes place during tissue segmentation and nuclei segmentation. Images with too many background pixels (empty images) or images with not enough background pixels (cropped images) will perform poorly during the segmentation analysis (described below) and therefore the range for background pixels must be determined such that images outside of this range are screened out prior to continuing with quantitative analysis of the disclosed embodiments.

Figure 3A:
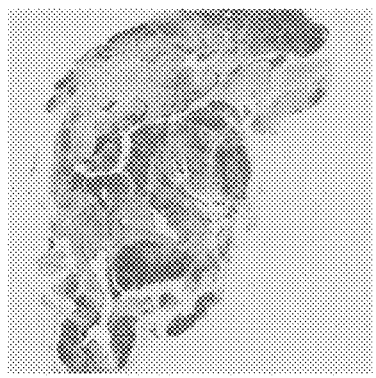
FIGS. 3A-3D below show slide images having varying amounts of background pixels.

The results of the background analysis may result in associating a background label (e.g., pass or fail) with the slide image. For example, FIGS. 3A-3D show slide images having varying amounts of background pixels. FIG. 3A depicts a slide image showing a tissue sample on an appropriate amount of background pixels. In an embodiment, a slide image with the appropriate amount of pixels is considered suitable for further analysis. This type of image may be considered a first background class.

Figure 3B:
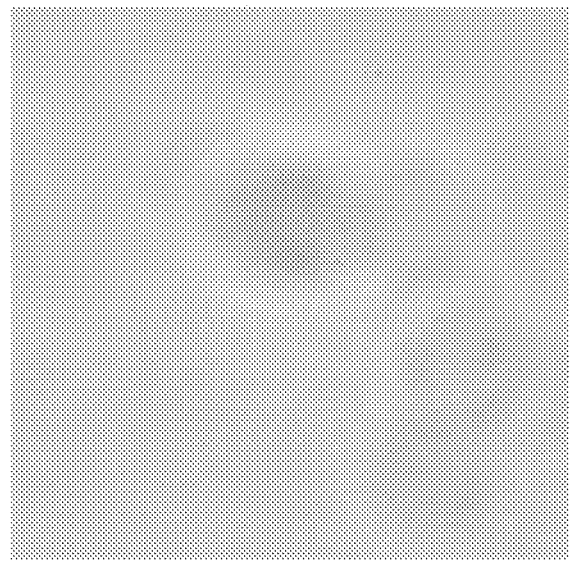
Figure 3C:
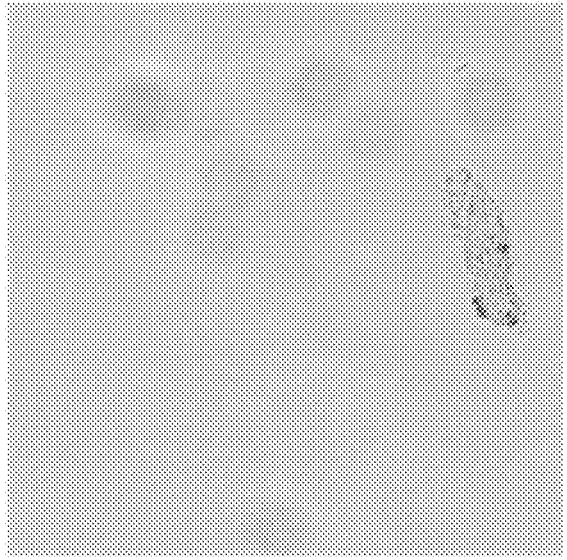

FIGS. 3B and 3C illustrate slide images with too many background pixels. In an embodiment, a slide image with too many background pixels is considered not to be suitable for further analysis. This type of image may be considered a second background class.

Figure 3D:
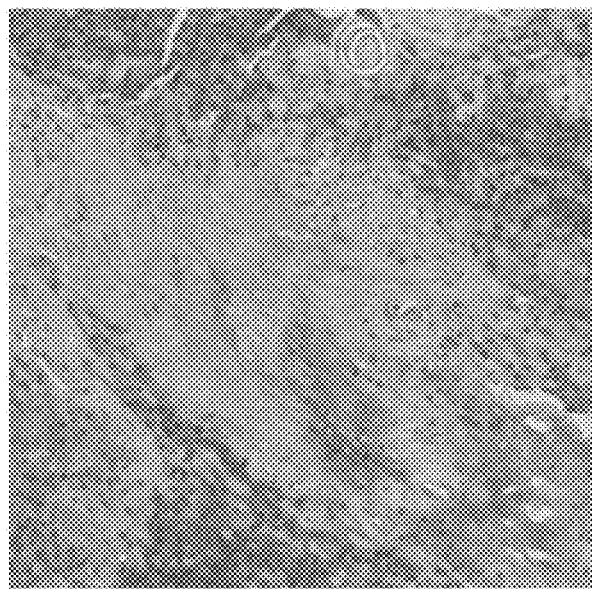

FIG. 3D illustrates a slide image with an insufficient number of background pixels. In an embodiment, such a slide image is considered not to be suitable for further analysis. This type of image may be considered a third background class.

Exemplary steps of the background analysis will now be discussed. The image background for slide images will be classified using classification intervals based on the ratio of the amount of background pixels to the total number of pixels. For example, empty images (e.g., FIGS. 3B, 3C) exhibit a very high image background ratio (e.g., 95%); cropped images exhibit a very low image background ratio (e.g., 5%) (e.g., FIG. 3D), and images with a normal amount of background pixels and tissue exhibit a moderate image background ratio (e.g., 200/% to 80%) (e.g., FIG. 3A). These values are merely exemplary and may be determined dynamically based on analysis of images within a training set.

The background analysis is performed for images within a training set (e.g., to generate the appropriate ranges for values that are considered to be suitable for quantitative analysis), for images in a control set (e.g., to determine whether the background values of images in the control set fall within the generated appropriate ranges) and for new unspecified images. In an embodiment, determining the image background ratio classification for slide images includes but is not limited to the following steps.

In an embodiment, determining the image background ratio classification for slide images for the training set includes but is not limited to the following steps:

1. Calculate the image background ratio for all images in the training set.
   a. Calculate the normalized image histogram counts.
   b. Use an inversion function on all image pixels from the red color channel to segment tissue pixels from background pixels (e.g., otsu_dark function in application ImageJ)
   c. Generate histogram counts from all image pixels with N bins where $N=2^{Bit\ depth}$ of slide image
   d. Divide all histogram counts by the total number of pixels in the image to normalize the data.
   e. Calculate the proportion of pixels greater than the threshold. This proportion represents the image background ratio.
2. Calculate classification interval of image background ratio for images that are considered to have an appropriate number of background pixels (e.g., pass).
   a. Calculate the mean image background ratio and standard deviation for each of the first, second, and third background classes.
   b. Calculate the upper bound of the classification range.
      i. Calculate the midpoint between the mean image background ratio for the first and second background classes. This value may be assigned as the upper range bound of the accepted classification interval.
   c. Calculate the lower bound of the classification range.
      ii. Calculate the midpoint between the mean image background ratios for first, second and third background classes. This value is assigned as the lower range bound of the accepted classification interval.

In an embodiment, the results of the foregoing steps performed on a training class of slide images produce an acceptable background range. Slide images having background values within this acceptable background range may be considered suitable for further quantitative analysis. The acceptable background range may then be applied to classify new images outside of the training class, such as images within a control library. For example, new slide images determined to have a background ratio within the background range calculated for images with the first background class (e.g., FIG. 3A) are classified as having an appropriate amount of background pixels and are accepted for the next step of analysis. Conversely, new slide images that are outside the background range calculated for images with a first background class (e.g., FIGS. 3B-D) are rejected and will not move forward for further analysis.

Tissue Entropy Analysis

Nuclei segmentation analysis ensures that nuclei pixels are suitably separated from other pixels in the slide image. Feature fingerprints of slide images are based, in part, on nuclei characteristics, so correctly segmented nuclei pixels are necessary for the quantitative analysis in embodiments. The results of the nuclei segmentation analysis may result in associating a nuclei segmentation label (e.g., pass or fail) with the slide image.

Nuclei segmentation analysis includes evaluating entropy of tissue pixels to ensure enough entropy exists such that accurate nuclei segmentation will take place. Image entropy, like thermodynamic entropy, corresponds to the number of states in a system. An image that has many different pixels values evenly distributed amongst the image has a high number of states, and therefore, a high entropy. An image with pixel values unevenly distributed amongst the image will have a low number of states, and therefore, a low entropy. Evaluation of entropy of tissue pixels in a slide image ensures proper contrast and sharpness exists in the image, which aid in the quantitative analysis of the slide image. Images with a low tissue contrast will have lower entropy compared to images with a normal amount of tissue contrast. The number and arrangement of pixels per nuclei corresponds to their "features" and for generation of feature fingerprints that are used to cluster the tissue samples. These features will vary from nuclei-to-nuclei in the slide image. In an embodiment, images that have passed the two previous steps (metadata analysis, image background) will proceed to this tissue entropy analysis.

When applied to a training set, the tissue entropy analysis creates a range for the accepted tissue entropy within an image. In an embodiment, tissue entropy analysis may include, but is not limited to, the following steps:

1. Segment all tissue pixels from background pixels.
   i. Use an inversion function on all image pixels from the red color channel to segment tissue pixels from background pixels (e.g., otsu_dark function in application ImageJ).
   ii. Calculate the entropy of all tissue pixels using an entropy equation and save the corresponding values. An example of an entropy equation is shown below where ET is the tissue entropy for all tissue pixels, p is the normalized histogram counts of the tissue pixels in bin i, and N is the number of histogram bins used in the histogram:

$$E_T = -\sum_{i=0}^{N} p_i \log_2 p_i$$

iii. Create a binary mask of all segmented nuclei within the slide image (e.g., applying function otsu_dark with all tissue pixels). A binary mask corresponds to a particular image and points to the pixels that will be used. Binary masks are usually created when segmentation is performed. For example, a binary nuclei mask that corresponds to an H&E image would be a matrix with the same dimensions as the original image where the nuclei mask is only 1-bit and only contains predetermined values (e.g., 0 or 1). Pixel locations that match the location of nuclei in the original image will have a predetermined value (e.g., 1), where non-nuclei pixels will have a predetermined value of (e.g., 0).
2. Create Nuclei Segmentation labels for all images. This label describes the success of the nuclei segmentation performed in the image processing routine described above with respect to tissue entropy analysis. Nuclei segmentation is the separation of nuclei pixels from all other pixels in the original slide (e.g., H&E) image. Nuclei segmentation is performed so the object analysis is performed only on cell nuclei in the image.

i. Determine accuracy of the nuclei segmentation. For example, this step may be performed using an application and comparing to an image key that provides examples of accurate and inaccurate segmentation.
   1. Overlay the binary nuclei mask on the red channel image using a certain opacity value (FIGS. 4A-C below).
   2. Examine a predetermined number of nuclei (e.g., 50) for correct segmentation that is defined as masks being properly overlaid on top of nuclei.
      a. If more than or equal to a certain number of nuclei (e.g., 45) of the predetermined number of nuclei are correctly segmented, the image may be given a first Nuclei Segmentation label (e.g., "0") (FIG. 4A).
      b. If less than the certain number of nuclei is correctly segmented, the image may be given a second Nuclei Segmentation label (e.g., "1") (FIGS. 4B, C).
   3. Calculate the classification interval of tissue entropy for images with the first Nuclei Segmentation label.
      i. Calculate the mean tissue entropy and standard deviation for each of the images having the first and second Nuclei Segmentation labels.
      ii. Calculate the lower bound of the classification range.
         1. Calculate the midpoint between the mean tissue entropy for the first and second Nuclei Segmentation labels. This value is assigned as the lower bound of the tissue entropy range.
         2. The accepted range of tissue entropies may span from the lower bound of the range calculated in step 3.ii.1 to infinity.

In an embodiment, the results of the foregoing steps performed on a training class of slide images produce an acceptable classification range for tissue entropy in a slide image. The acceptable classification range may then be applied to classify new slide images. Slide images with a tissue entropy value greater than the lower bound of the classification range (see step 3.ii.1) are classified as having an appropriate amount of tissue entropy and are accepted for analysis using this method. Slide images with a tissue entropy value that are less than the lower bound of the classification range are rejected and will not move forward for further quantitative analysis.

Figure 4A:
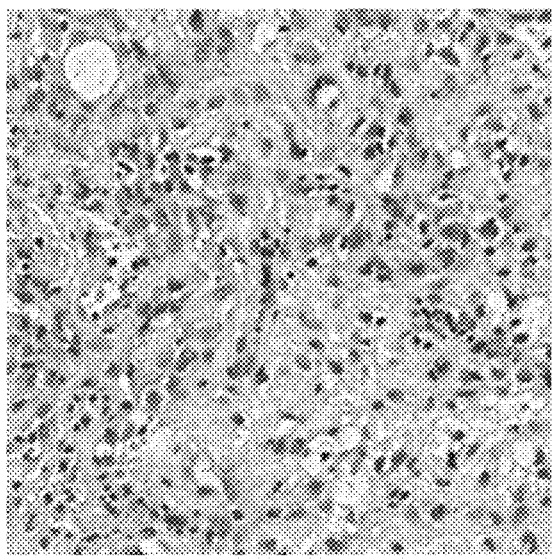
FIGS. 4A-4C illustrate slide images with varying degrees of nuclei segmentation.
Figure 4B:
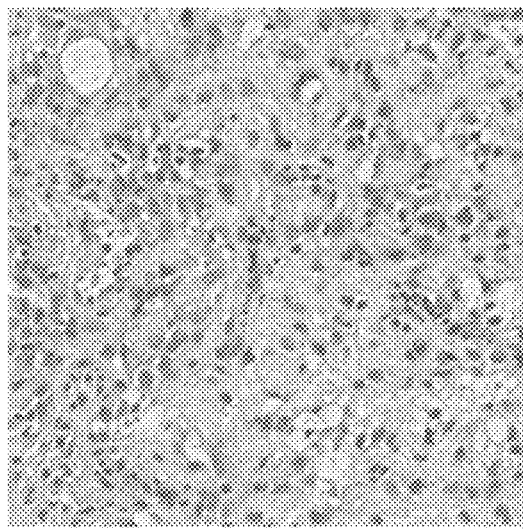
Figure 4C:
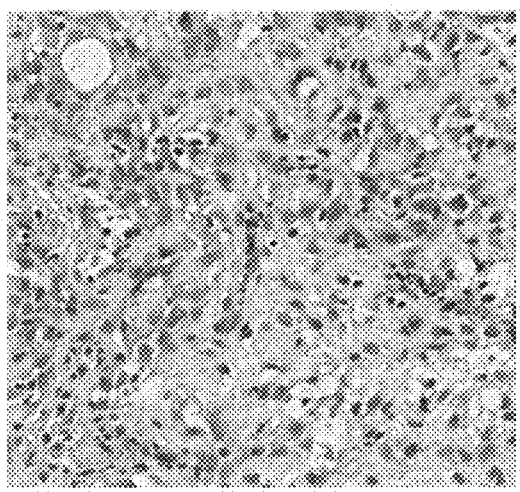

FIGS. 4A-4C illustrate slide images with varying degrees of nuclei segmentation. FIG. 4A illustrates a slide image with correctly segmented nuclei while FIGS. 4B and 4C illustrate slide images with incorrectly segmented nuclei.

Image Processing

The image processing feature is discussed further below with respect to analyzing hematoxylin channels of slide images since this channel depicts nuclear features of each cell. In an embodiment, the hematoxylin image is separated from the eosin image. In an embodiment, the image processing step also may include, as shown in FIGS. 5A-C below, transforming slide images into binary images for analysis. In an embodiment, slide images (FIG. 5A) are analyzed using the same resolution and scale. Contiguous regions of pixels are then extracted from the binary images in order to detect nuclei and the corresponding features of the nuclei (as shown in FIG. 5B). In an embodiment, the red channel of the slide image is extracted and inverted to form the binary image as shown in FIG. 5C. The red channel of the image, in some systems, provides the best image of the nuclei within slide images.

Feature Extraction

In an embodiment, the feature extraction step includes extracting features for each nucleus detected in the slide image and generating a fingerprint for each of the extracted features. In an embodiment, features are represented as numerical feature values. Table 1 below lists features that, for example and without limitation, are detectable and therefore capable of being extracted for each nucleus. One or more features may be extracted for each nucleus. For example, certain features may be more relevant for the purposes of different potency applications. That is, certain features may be determined to vary significantly between passing and failing tissues.

In an embodiment, when the tissue to be classified is thymus tissue (which may or may not be part of the assay), the relevant features extracted are area of each detected nucleus, perimeter of each detected nucleus, integrated density of each detected nucleus, and circularity of each nucleus. With regard to area, the nuclear area is larger for thymic epithelial cells than for thymocytes. The perimeter is related to cell viability, as cells degrade, the nuclear outline becomes irregular and its perimeter increases. Integrated density is high for thymocytes, which show uniformly dark staining. Thymic epithelial cells have dark-stained rims and mostly clear nucleoplasm with a prominent dark nucleolus. Thymocytes have increased circularity compared to thymic epithelial cells. Non-viable cells have reduced circularity compared to viable cells.

In an embodiment, the integrated density is represented by the size of the detected nucleus and a darkness value associated with the detected nucleus. The circularly represents an assessment of the circular shape of the detected nucleus and, in an embodiment, may be represented by a range (e.g., 0.0 to 1.0 where 1.0 represents a perfect circle).

TABLE 1

| Features extracted for each particle | | |
| --- | --- | --- |
| Area | Median | FeretX |
| Mean | Raw Integrated Density | FeretY |
| Perimeter | Integrated Density | FeretAngle |
| Width | Circularity | MinFeret |
| Height | Feret | Aspect Ratio |
| Major | Skew | Round |
| Minor | Kurtosis | Solidity |
| Angle | Min. distance to neighbor | Avg. distance to neighbor |

Figure 6A:
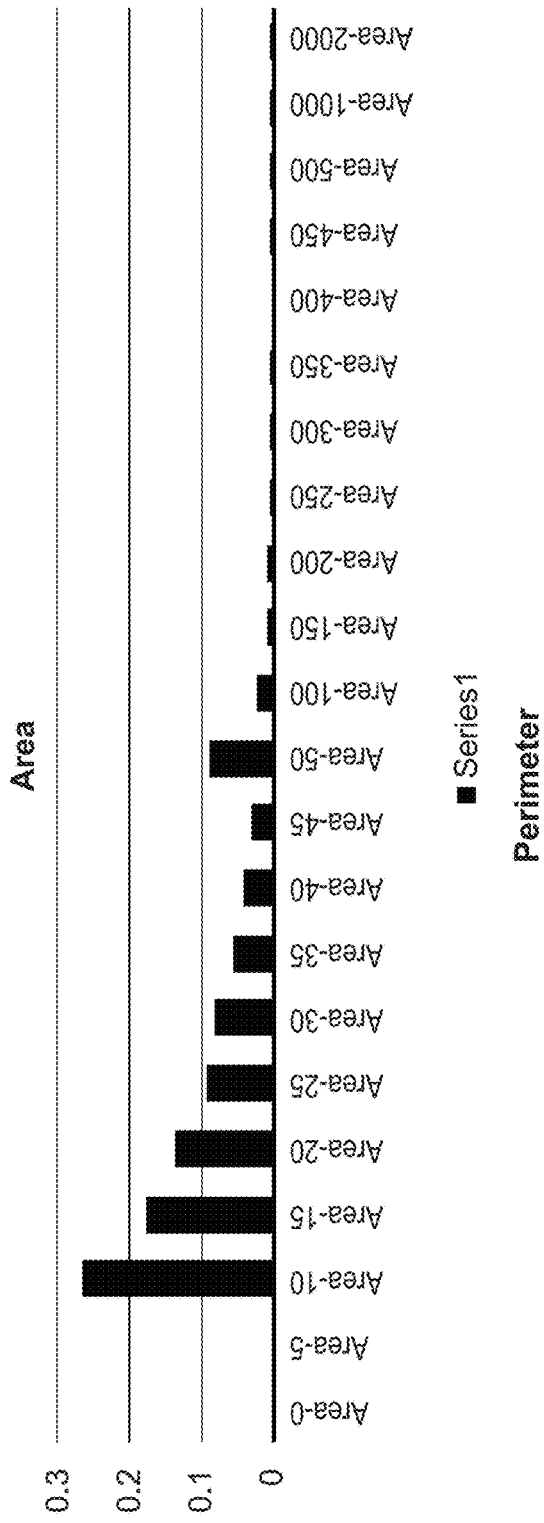
Figure 6B:
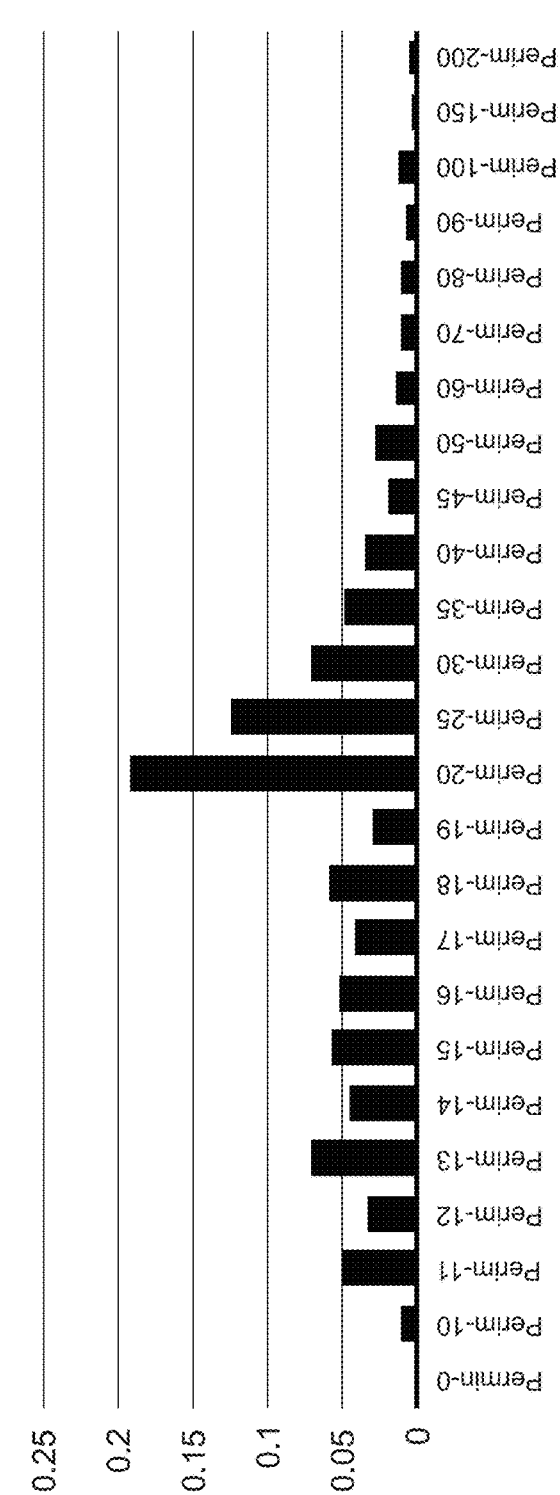

Determination of the feature fingerprint for a slide image according to an embodiment is now discussed. Initially, a numerical fingerprint is created for each of the extracted features. For example, in the embodiment described above, a feature fingerprint is generated for each the area, perimeter, integrated density, and circularity of nuclei within slide images. In an embodiment, histograms are generated for each of the extracted features (e.g., area, perimeter, integrated density and circularity). Each histogram shows the frequency of results in specific ranges (bins) for a feature. A feature fingerprint is generated from the combined histograms for each slide image. Clustering (discussed below and in the Examples set forth below) is based on the statistical analysis of the extracted features. Histograms are shown in FIGS. 6A-6D. FIGS. 6A-D illustrate exemplary results of feature extraction in an embodiment where the tissue is thymus tissue and the extracted features include area, perimeter, integrated density, and circularity. FIG. 6A illustrates area determinations. FIG. 6B illustrates perimeter determinations. FIG. 6C illustrates integrated density determinations. FIG. 6D illustrates circularity determinations.

Clustering

In an embodiment, clustering may include assembling clusters based on feature fingerprints of a slide image. In an embodiment, a Euclidian distance matrix for the generated feature fingerprint is tabulated. The distance matrix may then be used for hierarchical agglomerative clustering by looking for the optimum arrangement of slide images such that the within-group variance of slide images is minimized.

In an embodiment, feature fingerprints may be represented by a numerical value for each slide image generated from the combined histograms of extracted features as noted above. In the training phase, hierarchical agglomerative clustering is applied to the feature fingerprints of the slide images from a library of control images with known datasets such as Duke (Markert Lab), Forced Degradation (CT2), and Manufacturing (CT2) specimen slides. In an embodiment, clustering also includes performing statistical analysis to determine a cutoff height at which to segregate clusters into groups to ensure statistical significance between slide images within each group. In the classification phase, unknown samples are classified by co-clustering with the slide images from the library. The unknown samples are then classified based on the group within the cluster in which the unknown samples are co-clustered.

Figure 7:
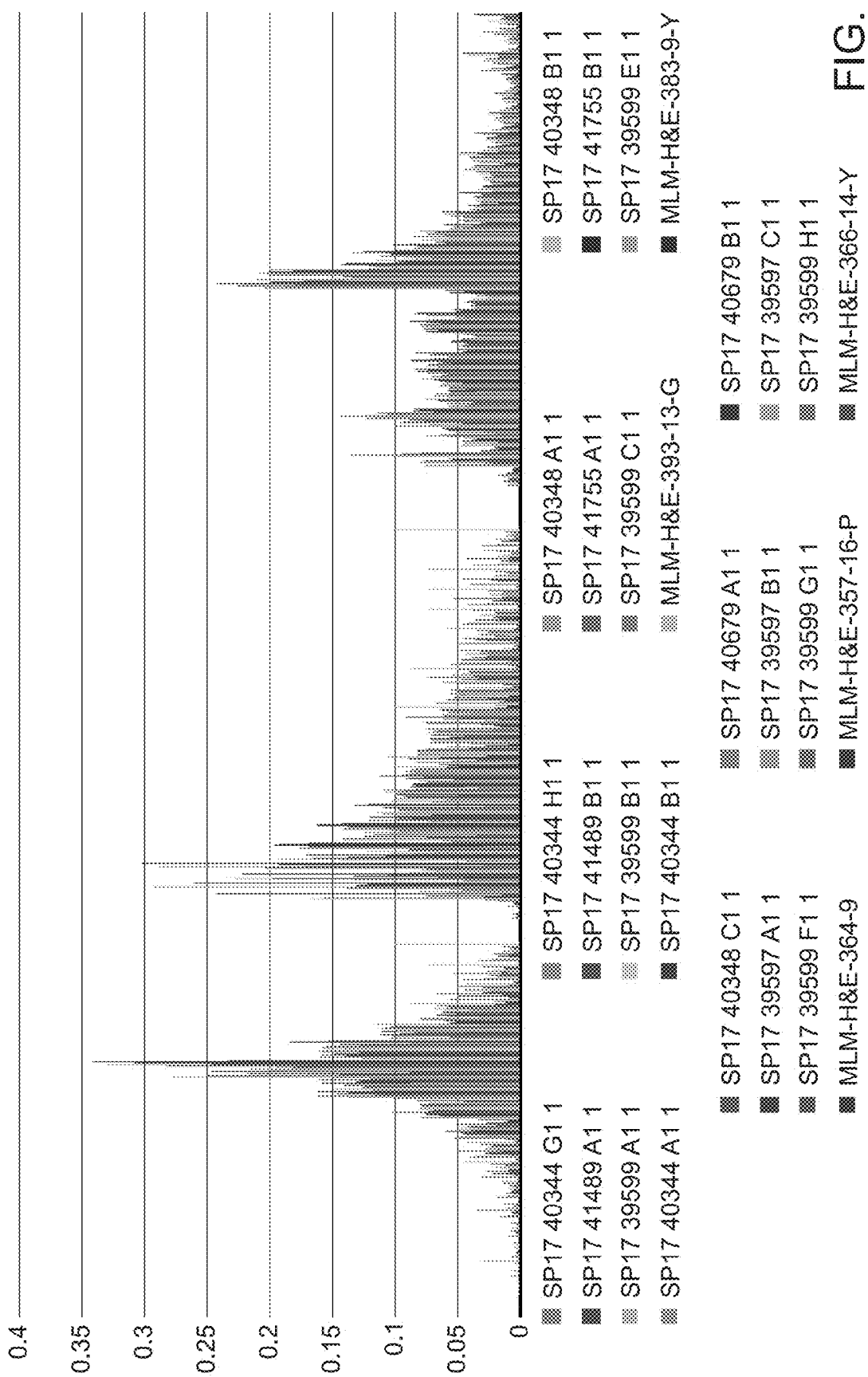
FIG. 7 illustrates a representation of fingerprints generated for slide images. Fingerprints are quantitative representations of underlying features of nuclei within an image.

FIG. 7 below illustrates an exemplary representation of fingerprints generated for slide images. As noted above, fingerprints are quantitative representations of underlying features of nuclei within an image.

Figure 8:
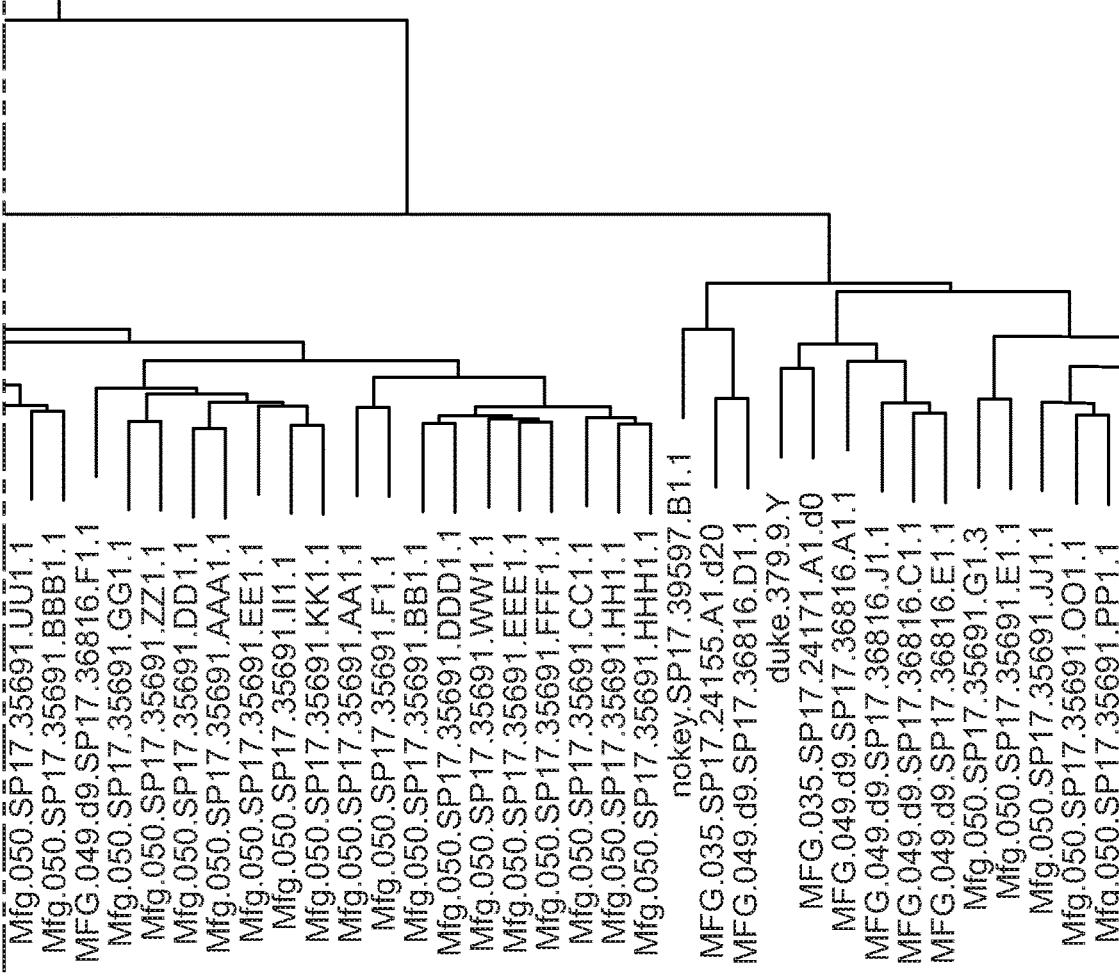
FIG. 8 illustrates a representation of a raw output from a clustering step that includes thymus specimens received from Duke University.
Figure 8:
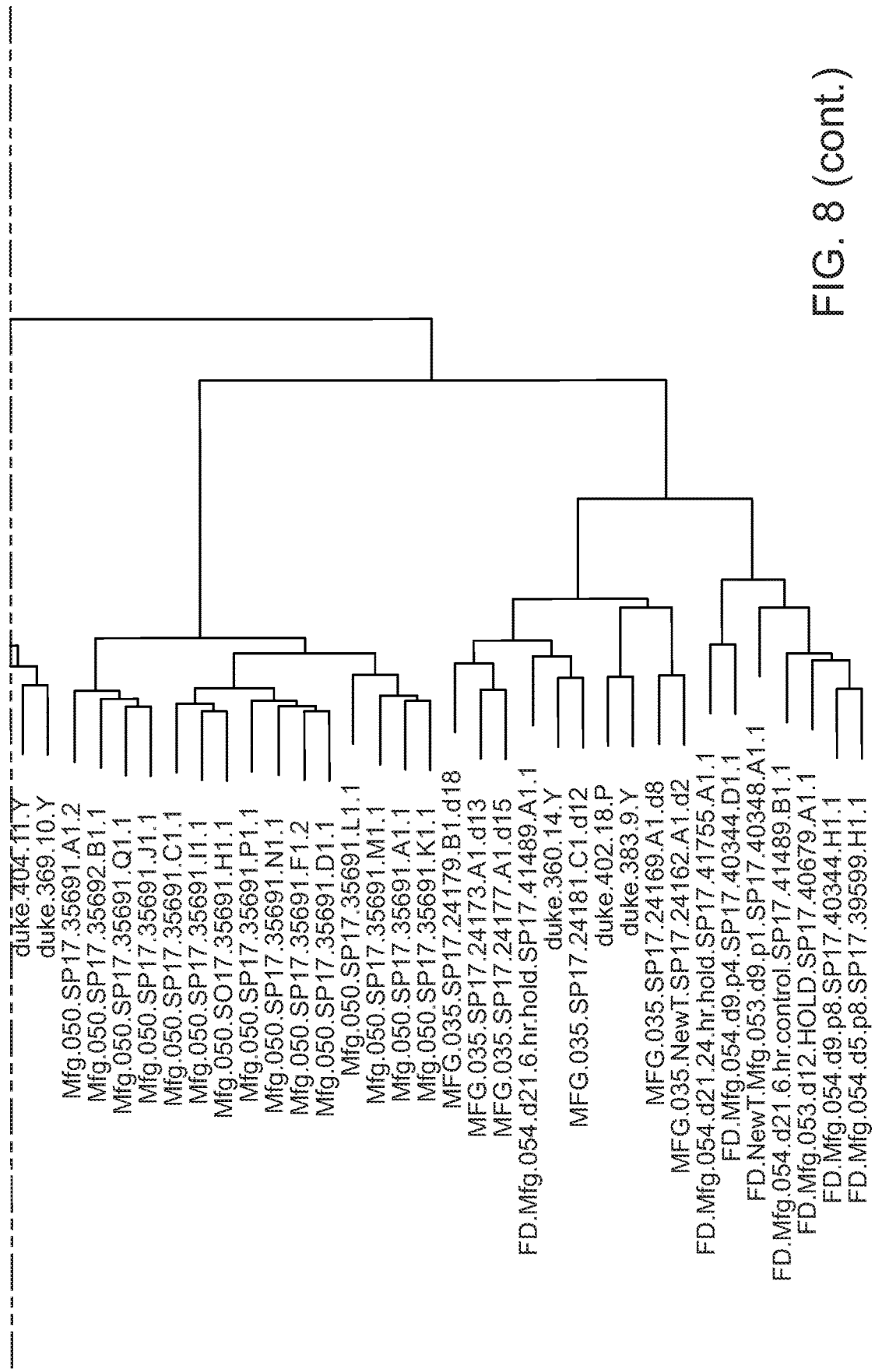

FIG. 8 below illustrates an exemplary representation of a raw output from a clustering step that includes data from tissue samples supplied by Duke University.

In an embodiment, the clustering step may include segregation of a cluster into groups. A cutoff height must be calculated by which to perform the segregation in a statistically significant manner. In an embodiment, the cutoff height is calculated through a systematic increase of a cut-off height with corresponding multiple analysis of variance (MANOVA) between and amongst groupings and the selected cutoff height minimizes the number of groups while maximizing the statistical significance of differences in feature fingerprints between the group populations. In an example experimental test where the tissue was thymus tissue and the extracted features included area, perimeter, integrated density, and circularity, a cutoff height (e.g., 0.4) was determined for segmentation of clusters which resulted in segregating the clusters into a certain number of groups (e.g., 9).

In an example experimental test, after groups were formed, groups were assigned as a positive control group if the population of samples within the group consisted of slide images from samples previously determined to have passed the potency criteria (i.e., "good" samples having a pass classification). Examples of these groups include the Duke and manufacturing datasets. Groups were assigned as a negative control group if the population of samples within the group consisted of slides previously determined to have failed the potency criteria (i.e., "bad" samples having a fail classification). Examples of these groups included the forced degradation dataset.

Figure 9:
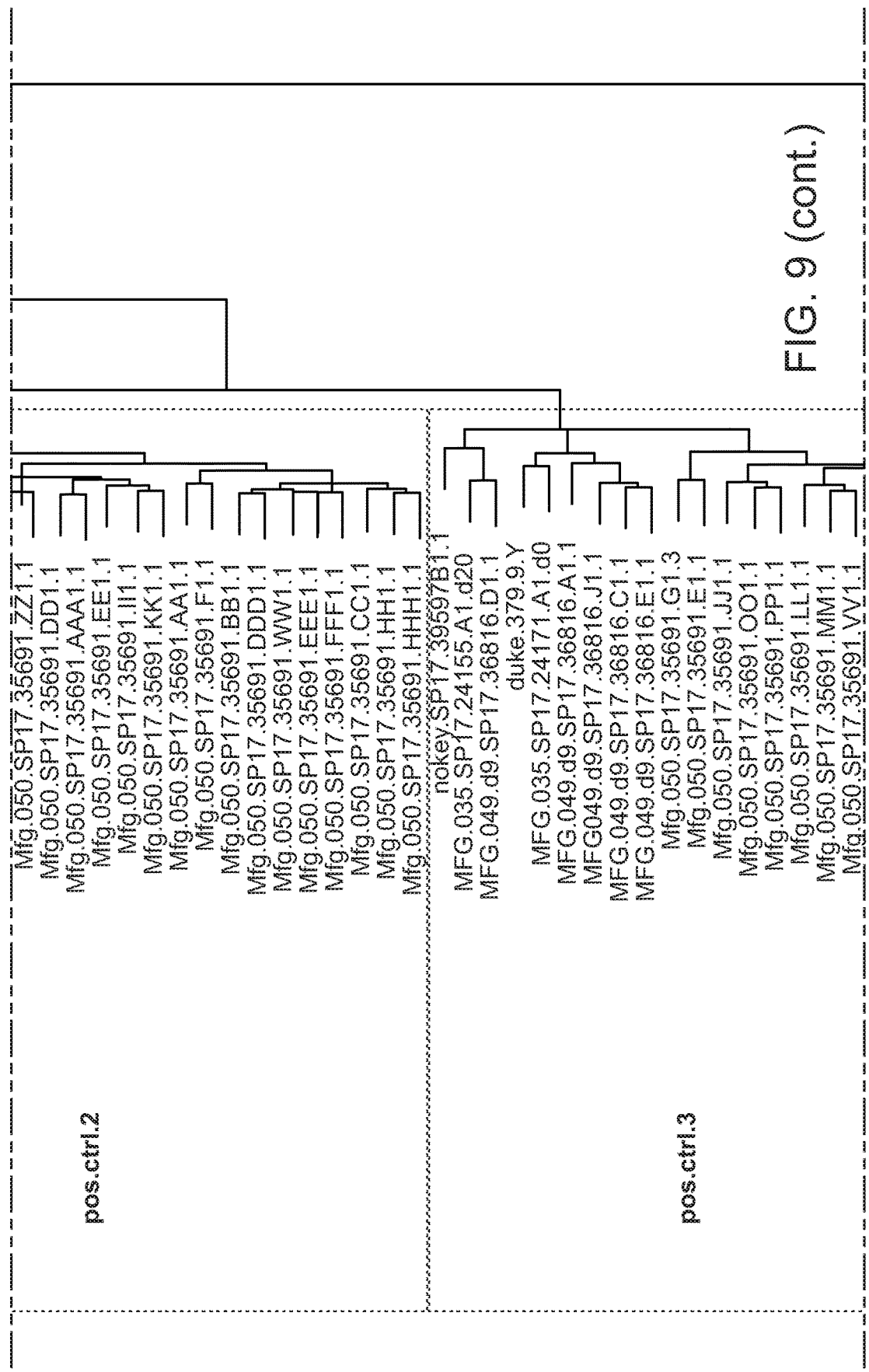
FIG. 9 illustrates a result of the grouping step during the training phase. Illustrated in FIG. 9 are multiple positive and negative control groups clustered based on slide images of experimental samples of thymus tissue.
Figure 9:
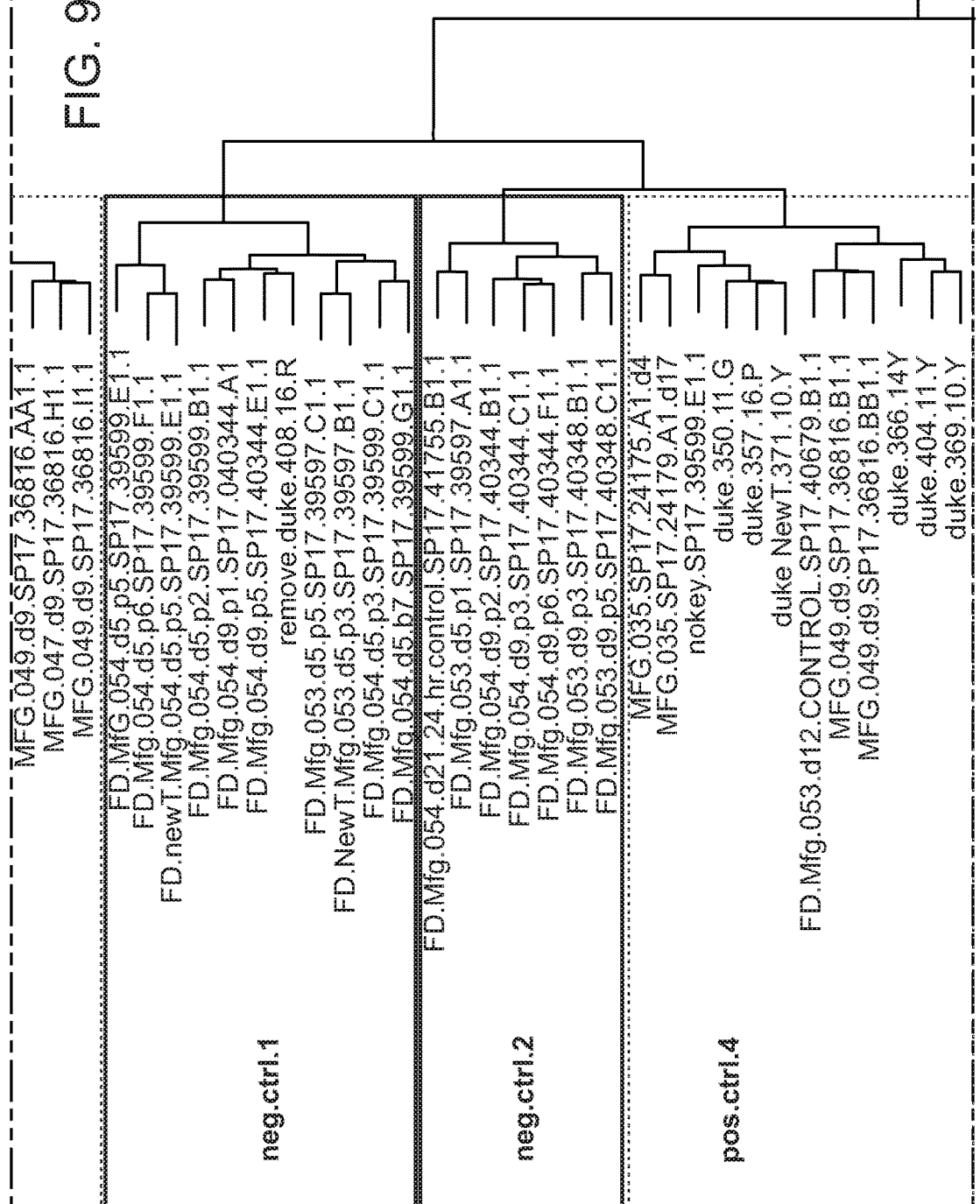

FIG. 9 below illustrates an example result of the grouping step during the training phase.

FIG. 9 illustrates multiple positive and negative control groups clustered based on slide images of thymus tissue. In such an embodiment, there may be no single pass/fail criterion for potency. Rather, multiple features may differentiate samples and may be considered for potency. There can be more variation among the positive control groups based on variation in the slide images such as in the region that the section was taken from and the size of tissue. For example, sections taken from different regions of a more complex tissue such as a thymus will have different corticomedullary ratios (e.g., distribution of thymocytes, epithelial reticular cells, and number of Hassall Bodies) but can still meet the pass criteria for potency.

In an embodiment, the following description of the control groups in FIG. 9 is merely exemplary and is meant to illustrate possible common features of slide images that result in the formation of the respective control groups. Control groups may be formed based on other features or combination of features within the slide images contained in them. In the example of FIG. 9, a first negative control group in FIG. 9 ("neg.ctrl.1") was grouped based on the presence of Hassall Bodies, poorly defined medulla and cortical regions, and extensive necrosis and fibrosis. A second negative control group in FIG. 9 ("neg.crtl.2") was grouped based on minimal or no presence of Hassall Bodies, fibrosis and necrosis, and poorly defined medulla and cortical regions. A third negative control group in FIG. 9 ("neg.crtl.3") was grouped based on minimal or no presence of Hassall Bodies, fibrosis and necrosis, and poorly defined medulla and cortical regions.

Regarding the positive control groups shown in FIG. 9, in this example, a first control group in FIG. 9 ("pos.crtl.1") was grouped based on lack of defined cortex or medulla region, presence of Hassall Bodies, and low to normal amount of lymphocytes. A second control group in FIG. 9 ("pos.crtl.2 was is grouped based on presence of normal epithelial cells, normal cortex and medulla regions, presence of Hassall Bodies, and lymphocytes with normal mature T cell changes. A third control group in FIG. 9 ("pos.crtl.3") was grouped based on presence of normal epithelial cells, normal cortex and medulla regions, presence of Hassall Bodies, and lymphocytes with normal mature T cell changes. A fourth control group in FIG. 9 ("pos.crtl.4") was grouped based on low amount of lymphocytes, varying degrees of medullar and cortical regions, presence of necrosis extending from medulla into cortex for some tissues, and varying epithelial cells from none to present. A fifth control group in FIG. 9 ("pos.crtl.5") was grouped based on normal cortex and medulla regions, presence of Hassall Bodies, normal thymocyte distribution, and lymphocytes with normal mature T cell changes. A sixth control group in FIG. 9 ("pos.crtl.6") was grouped based on minimal or no presence of Hassall Bodies, lack of identification for cortex and medulla areas, and high degree of fibrous tissue. Alternative clustering techniques of the present disclosure may be found in the Examples of the present specification.

Tables 2 and 3 below illustrate example results of a statistical analysis of forming groups after performing a co-clustering analysis. In an embodiment, MANOVA analysis is performed. Table 2 illustrates that groups based on a co-clustering analysis resulted in populations between the clustered groupings differing significantly from each other.

TABLE 2

| | Grouped by clusters of co-clustering analysis | | | | | |
|---|---|---|---|---|---|---|
| | Deg. freedom | Pillai | approx F | num Df | den Df | P |
| Group | 8 | 7.2422 | 6.0573 | 568 | 360 | <2.2e−16* |
| Residuals | 108 | | | | | |

TABLE 3

| | Df | Pillai | approx F | num Df | den Df | P |
|---|---|---|---|---|---|---|
| Group | 4 | 2.318 | 0.87345 | 284 | 180 | 0.8456** |
| Residuals | 112 | | | | | |

Figure 10:
FIG. 10 illustrates example results of a statistical analysis of the differences between populations within each segmented group of Table 2.

FIG. 10 further illustrates example results of the statistical analysis of the differences between populations within each segmented group of Table 2. FIG. 10 shows that the population of slide images within each group did not vary significantly, which indicates that those slide images share similar feature fingerprints.

Table 3 illustrates that groups of randomly generated groups (i.e., without performing co-clustering) resulted in no statistical significance between the populations of each group.

In an embodiment, after the training phase, the classifier has established segmented groupings of the slide images from the library. The groupings are separated into positive control groups and negative control groups, where the positive control groups include slide images that have been previously determined to be candidates for transplantation (i.e., pass classification) and the negative control groups include slide images that have been previously determined to not be candidates for transplantation (i.e., fail classification).

In the classification phase, a sample slide image to be classified is analyzed to assess the potency of the tissue in the slide image. The slide image is processed in preparation for the analysis. In an embodiment, this includes conversion of the image into a binary image. Feature detection is next performed. In an embodiment, a hematoxylin channel (i.e., nuclei) is extracted from the slide image. Features are determined for the extracted channel. A feature fingerprint is generated based on the features of the extracted channel. In an embodiment, the feature fingerprint may be represented by a histogram as shown in FIG. 8 above. In another embodiment, the feature fingerprint is generated from area, perimeter, integrated density, and circularity features of the extracted channel.

The generated feature fingerprint may then be compared with feature fingerprints of positive and negative control groups that were generated during the training phase. In an embodiment, the comparison step includes co-clustering the generated feature fingerprint with the feature fingerprints of the positive and negative control groups.

After co-clustering, statistical analysis (e.g., MANOVA) may be performed to evaluate the formed clusters for determining whether the generated feature fingerprint clusters correlate in a statistically significant manner with any of the positive or negative control groups. If the results of the statistical analysis indicate a lack of statistically significant clustering or that generated feature fingerprint clusters with a negative control group, the slide image is either considered to have failed the potency criteria and may be associated with a fail classification or it may be assessed qualitatively for disposition. If the results of the statistical analysis indicate clustering with a positive control group, the slide image is considered to have passed the potency criteria and may be associated with a pass classification.

Figure 11:
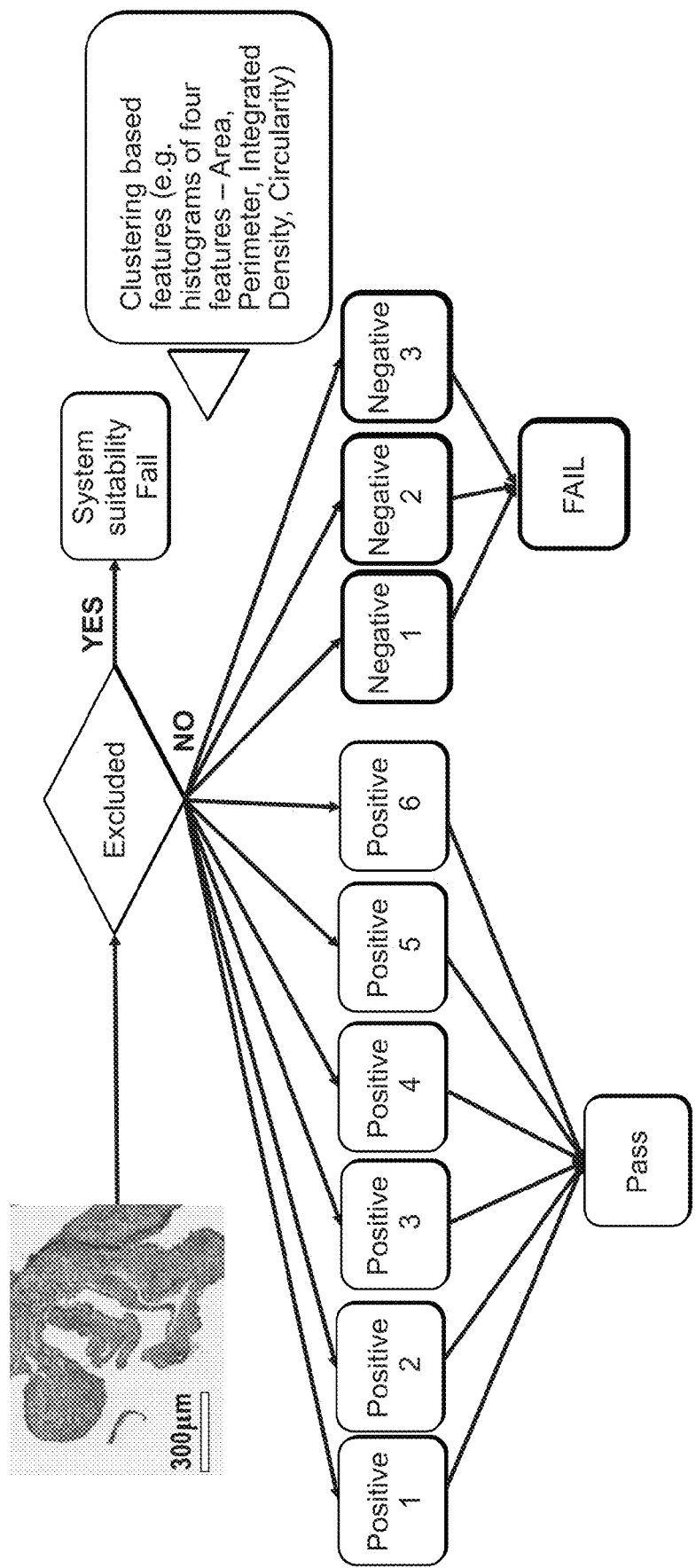
FIG. 11 is a flowchart of an example analysis of a slide image. In an embodiment, the flowchart is implemented by a classifier that performs the processing steps described above. A slide image may first be evaluated to determine whether the image is suitable for being analyzed during the classification step.

FIG. 11 below represents a flowchart of an example analysis of a slide image. In an embodiment, the flowchart is implemented by a classifier that performs steps described above. A slide image may first be evaluated to determine whether the image is suitable for being analyzed during the classification step. If not, the slide image is excluded and is determined to have failed to the suitability requirements for analysis. If the slide image meets the necessary suitability requirements, the slide image is not excluded and is analyzed. The analysis includes at least one of the image processing, feature extraction and clustering steps discussed above. The results of the test result may result in determining whether the feature fingerprint of the slide image is clustered with one of the positive control groups or negative control groups. As shown in FIG. 11 below, if clustered with a positive control group, the slide image is considered to meet the potency criteria and therefore may be associated with a pass classification. If clustered with a negative control group, the slide image is considered not to meet the potency criteria and therefore may be associated with a fail classification.

Table 4 below describes corresponding qualitative characteristics of tissue from slide images in negative control groups and positive control groups in an experimental embodiment when the classification phase was applied to a library of slide images of thymus tissue.

TABLE 4

| | Negative Control Groups | Positive Control Groups |
|---|---|---|
| Cortical and Medullary Regions | Poorly defined | Mostly normal cortical and medullary regions with some samples having poorly defined areas |
| Thymocytes | Generally low quantity of medullary thymocytes and low overall quantity | Varying quantity and distribution from normal to absent |
| Necrosis | Significant degree of necrosis | Minimal Necrosis - focal areas of necrosis in few tissues in medulla |
| Fibrosis | Significant degree of fibrosis | Minimal fibrosis - primarily seen in Duke control samples |
| Hassall Bodies | Primarily present - few tissues without Hassall Bodies | Primarily present - few tissues with Hassall Bodies |

Table 5 illustrates characteristics corresponding between negative control groups (labelled Negative 1-5) and positive control groups (labelled Positive 1-6).

TABLE 5

| | Hassall Bodies Present | Number of Thymocytes | Necrosis and Fibrosis | Defined Medulla and Cortical Regions |
|---|---|---|---|---|
| Negative 1 | Yes | Low to None | Yes | No |
| Negative 2 | Minimal | Low to None | Yes | No |
| Negative 3 | Minimal | Low to None | Yes | No |

TABLE 5-continued

| | Hassall Bodies Present | Number of Thymocytes | Necrosis and Fibrosis | Defined Medulla and Cortical Regions |
|---|---|---|---|---|
| Positive 1 | Yes | Low to Normal | No | No |
| Positive 2 | Yes | Normal | No | Yes |
| Positive 3 | Yes | Normal | No | Yes |
| Positive 4 | Yes | Low | None to Moderate | Variable |
| Positive 5 | Yes | Normal | No | Yes |
| Positive 6 | None to Minimal | Low | Yes | No |

In an embodiment, clustering is based on composition and features of nuclei for all cells within slide images. For thymus cells, thymocytes may be a contributing factor for the analysis, as they comprise a majority of population nuclei. Medulla and cortical thymocytes contribute differently to the feature fingerprints based on the features used for the fingerprints. Quantitative differences in the cell population lead to quantitative differences in the feature fingerprints that lead to differences in clustering. Thymocyte composition portrays tissue health as significant variations in composition indicate necrosis, fibrosis, and general degradation. Clustering groups samples that share a similar fingerprint pattern, and hence share similar features of their cellular populations. Sample images whose fingerprints differ statistically significantly will be located in different groups.

The disclosed embodiments for quantitative analysis and feature fingerprint generation enable a classifier to detect shifts in cell population, because feature fingerprinting evaluates every detectable nuclei in a slide image. During culturing, the overall number of thymocytes should reduce in tissues. However, the relative proportion of cortical to medullary thymocytes should stay consistent. Significant alterations to these proportions can indicate uneven tissue degradation or compromise of potency. Significant changes in cell population will be detected as shifts in the quantitative feature fingerprints. Significant change in corticalmedullary thymocyte ratio (increase or decrease) will cause a shift in feature fingerprints toward negative control groups, and hence the sample will cluster with negative control samples.

Figure 12C:
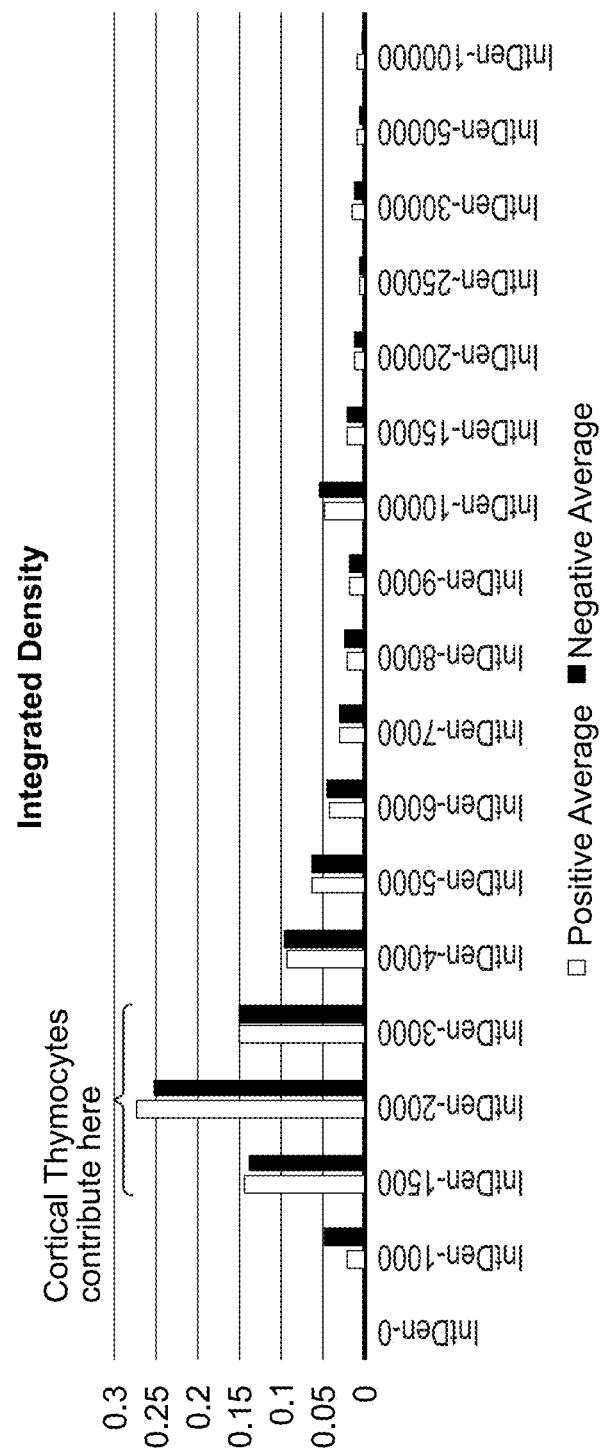
Figure 12D:
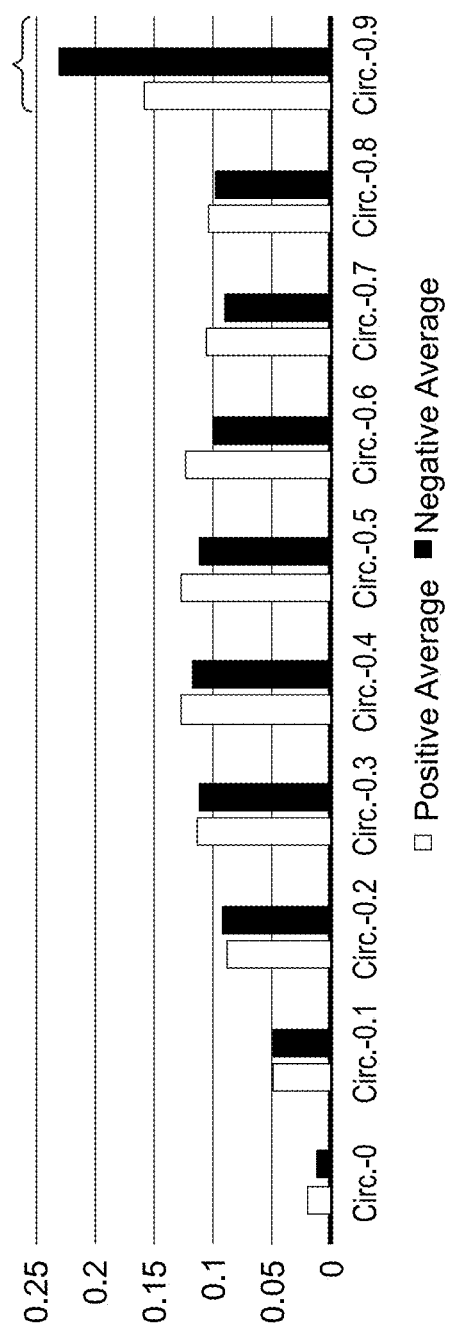

FIGS. 12A-12D are prophetic examples that may show example feature fingerprints based on certain extracted features of a slide image of thymus tissue. FIG. 12A illustrates a difference between slide images associated with positive and negative control groups in feature fingerprints generated for the area of the nuclei. FIG. 12B illustrates a difference between slide images associated with positive and negative control groups in feature fingerprints generated for the perimeter of the nuclei. FIG. 12C illustrates a difference between slide images associated with positive and negative control groups in feature fingerprints generated for the integrated density of the nuclei. FIG. 12D illustrates a difference between slide images associated with positive and negative control groups in feature fingerprints generated for the circularity of the nuclei.

Figures 13C, 13D:
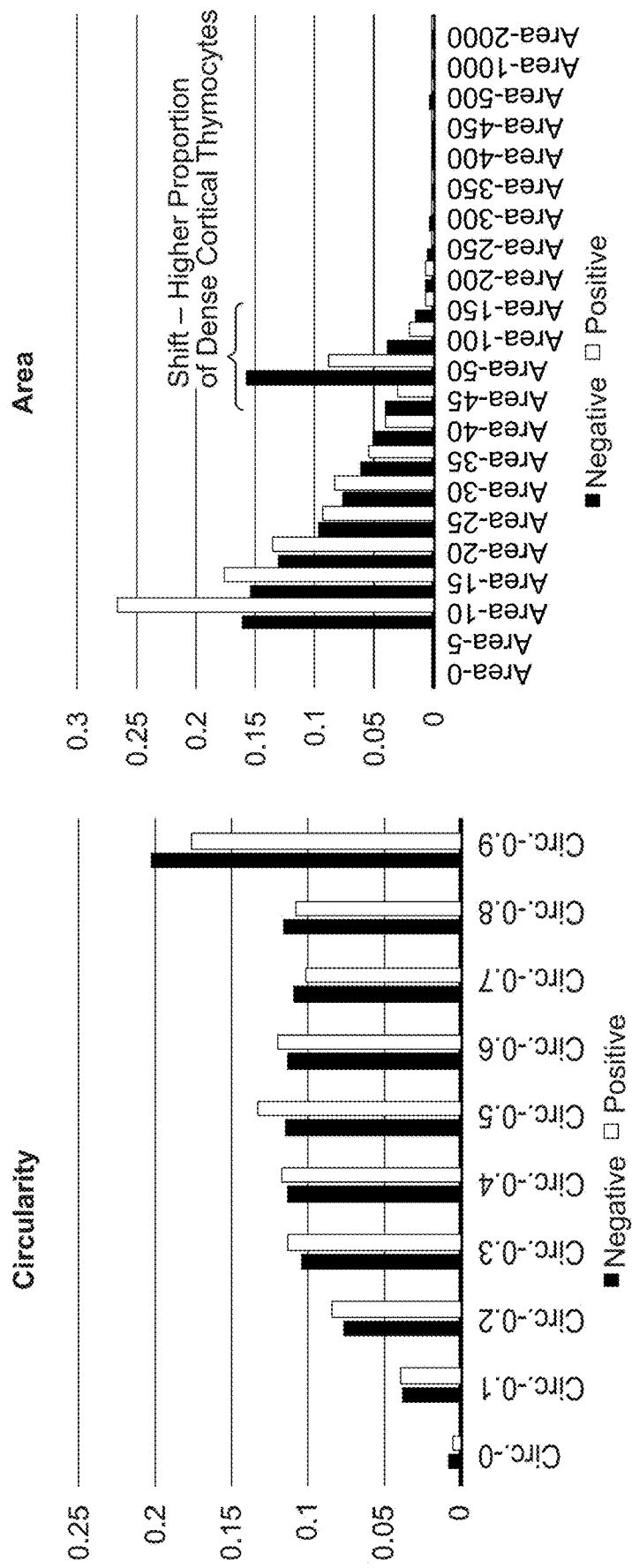
Figure 14A:
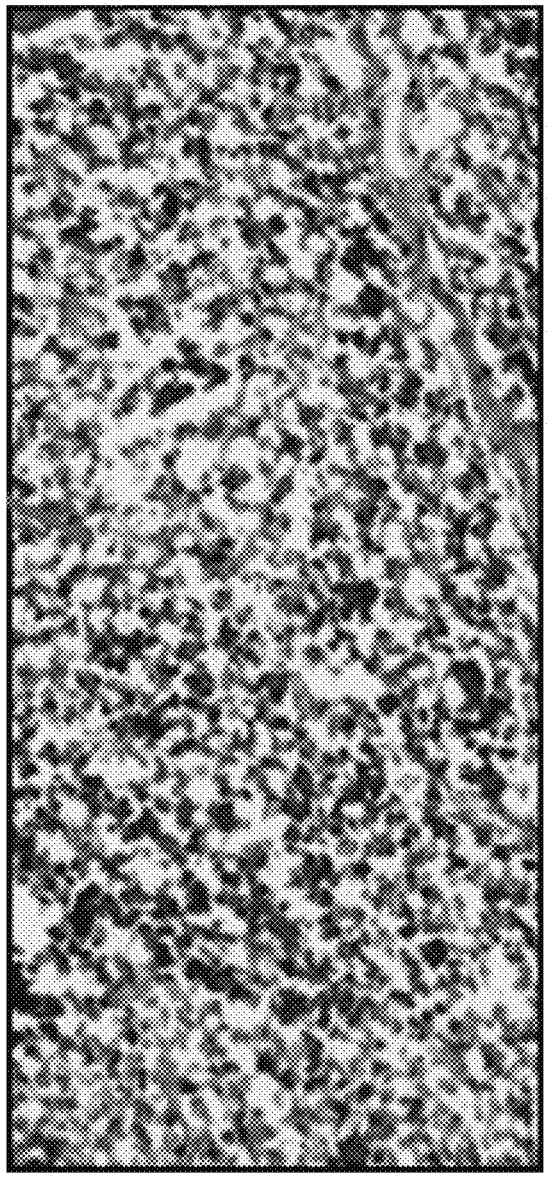
FIGS. 14A-14D depict nuclei of clinical and degraded cultured thymus tissue.
Figure 14B:
Figure 14C:
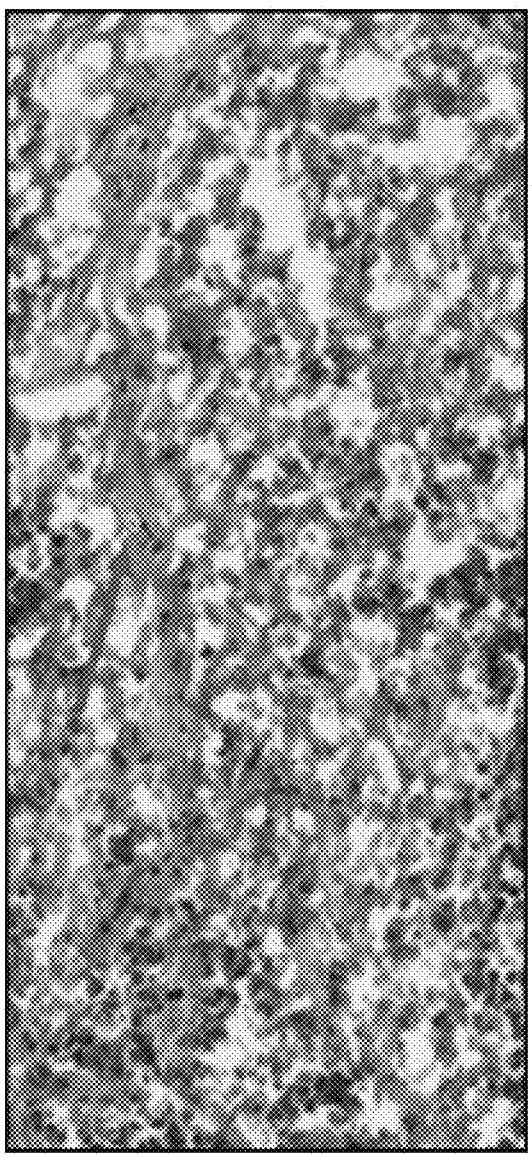
Figure 14D:
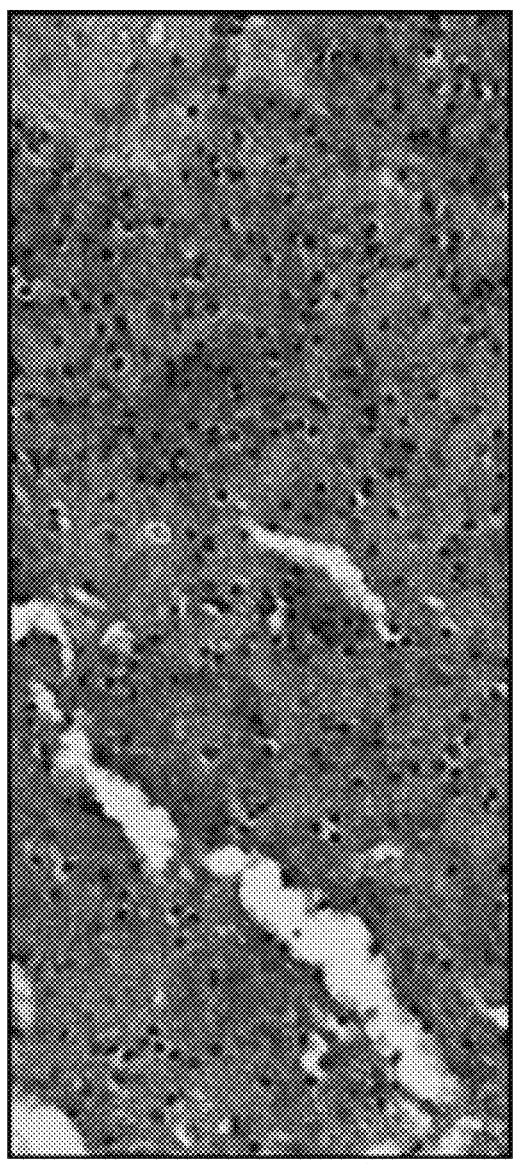

FIG. 13 illustrates feature fingerprints from an exemplary application of the classifier to an example slide image of thymus tissue associated with a negative control group and an example slide image of thymus tissue associated with a positive control group. The feature fingerprints, including those for area and integrated density features, illustrate differences in cortical thymocytes between the negative control group slide image and the positive control group slide image.

In a preferred embodiment of the present invention, the methods of performing quantitative histopathological assessment of an unclassified slide image of a tissue and methods of training a tissue classifier to perform quantitative histopathological assessments can be performed in the following exemplary manner.

A culturing time period for the tissue to be examined is selected based on results constituting positive clinical outcomes following the implantation of a desired tissue-engineered product. With regard to allogeneic cultured post-natal thymus tissue-derived product, the culturing time period allows the tissue to deplete thymocytes either through washing them out of the tissue and/or through apoptosis. TECs in the cultured thymus tissue are substantially maintained throughout the culturing time.

An assay examines a sample taken from between days 5-9 of culture to assess the suitability of the cultured thymus tissue for release and transplantability. To help understand the product better and to better assess the discerning capabilities of the assay, samples are taken from days 1 to 21 and beyond, data on which can be assessed to determine apparent trends.

For example, batches of clinical cultured thymus tissue samples and a degraded thymus tissue sample may be examined for histopathological features such as area, perimeter, integrated density, and circularity. The overall trend in the number of nuclei detected are examined, this is expected to decrease over time as thymocytes wash out of the tissues or undergo apoptosis. These data are then normalized for tissue area as different slices from multiple lots are examined on the different days. Tissue section size can differ between slices and can cause variability in the data set, but a general negative trend can be seen with increasing culture days, with a visual step change in the data around day 10. Previous data has shown that the majority of thymocytes are depleted earlier in the culture period when compared to the decrease in the total number of cells. The cultured tissue samples may then be analyzed in time course studies to assess, for example, inter-tissue variability. For illustrative purposes, the process will be described for assessing inter-thymus tissue variability. This will include an assessment of thymic epithelial cells and thymocytes. The data obtained in the inter-thymus variability step will be subjected to hierarchal cluster analysis. A training set of data will be established and then a group by group analysis of the cultured thymus tissue will be determined. These data will be compared to data obtained in either a forced degradation study of the tissue and/or by comparing the group by group determination to s set of data associated with failed specimens with negative clinical outcomes.

The general appearance of the tissue, and consequently the histology slides, changes over the course of the selected culture period, for example at 0, 5, 9, 12 and 21 days for cultured thymus tissue. Again, in the illustration of cultured thymus tissue, as thymocytes are washed out of the cultured thymus tissue. The tissue at Day 5, 9, 12 and 21 shows a marked decrease in integrated density and a profile more similar to the profile for thymic epithelial cells. The number of cells with very high circularity diminishes over time throughout the culturing process. This is likely due to apoptosis resulting in nuclei that are less circular as well as washing out of the very circular thymocytes. For samples at Day 0 with lower circularity it is likely due to clumping of thymocytes being measured as a single entity with lower circularity than a single nuclei. At Day 0 there are a large proportion of cells with high perimeters, which is likely due to clumps of cells being read in the program as a single shape resulting in the large perimeter values. The increase in perimeter is likely a combination of the thymocyte washing out as well as cells undergoing apoptosis over culture time and a resulting increase in perimeter from that event. Overall, nuclear characteristics over the course of culture time aligns with theoretical expectations for trends. Most of the apparent shifts in the data are prior to the intended release days of the lots. This suggests that many of the changes occur during the initial days of culture, after which the environment is able to be sustained for up to 21 days. This is supportive of the assay to detect true trends in the cell populations and how they change over time.

Inter-thymus variability is examined to better understand if samples are similar between thymuses. Inter-thymus variability may be assessed in a similar manner to intra-thymus variability where samples examined are from a single day, but instead of being restricted to a single thymus, the assessment includes samples across lots. The Euclidean distance of each sample can be calculated to the center point of all samples within the isolated data set. ANOVA's are then performed on the distances to center by thymus. Such an analysis is performed on samples on Days 5 and 9. Inter-thymus variability may be examined to better understand if samples are similar between thymuses. Ninety-five percent confidence intervals at each day are generated per thymus. A more specific analysis of only thymic epithelial cells is performed to help characterize the allogeneic, cultured postnatal thymus tissue-derived product. Thymic epithelial cells are hypothesized to be critical for the mechanism of action of the allogeneic, cultured postnatal thymus tissue-derived product. A pathologist selects nuclei for cells identified as thymic epithelial cells. The nuclei of thymic epithelial cells differ from other cells in the tissue population. TECs are generally larger, and have a nucleolus present, which appears as a darker purple dot within the center of the lighter purple outer nucleus. Known marked cells are then extracted as individual data points from the software. Using this data, a filter can be devised to enable the following steps to be performed in sequential order. Two size filters remove any cells outside of the size range window both pre- and post-splitting of conjoined cells. The following filtering steps were carried out.

The darkest cells are removed from the dataset by defining threshold of inclusion below darkest pixels. Cells below 50 µm in area are then removed. Holes are filled, and watershed applied to split conjoined cells. Cells outside a range of 30-250 µm$^2$ and circularity <0.75 are then filtered out of the dataset. The foregoing filters permit analysis of images with data sets generated and restricted to characterize the TEC cells. When examining the total proportion of cells in the tissue over the course of the culture period, there is a general increase in TECs. The increase in TECs is because, as the thymocytes are washed out of the tissue, a larger number of the remaining cells are TECs. The foregoing analysis of TECs also provides a better view of the trends of the thymocytes washing out of the tissue through the culture period. A similar analysis can be inferred from the data, that the number of thymocytes is reduced during the course of the culture as the ratio of TECs increase. The foregoing data may be used to show the samples broken into groups. The groups are generated through hierarchal cluster analysis. This analysis systematically and statistically identifies samples with similar characteristics by iteratively grouping data based on similarities resulting in meaningful clusters of data of similar properties (referred to as "groups"). The process for grouping cells required the following steps:

The distance between groups is calculated. Distance is a measure of similarity between groups. The cost: of joining two groups is calculated. The cost here is how much error is added by joining the groups. The groups that have the least merging cost are joined. The process is repeated until all data are joined into one group. The resulting data set essentially shows a family tree of how "related" or similar the samples are to each other. The height between the branches shows how related two groups are to each other. Distance on the horizontal x-axis does is not indicative of any closer relationship when graphed. Samples within each group are considered to be statistically similar, while those in different groups are considered statistically different.

To determine where the cut height is between the different groups, a Scree Plot can be used to examine where the distances between the groups are most significant. This ensures that minimal differences between samples do not overly influence the algorithm. Too small of differences will result in more likely fracturing of future samples into independent groups as the samples have to be too similar to cluster together than is realistic for allogeneic, cultured postnatal thymus tissue-derived product. Alternatively, the groups must have an appropriate cut off to ensure that there is differentiation between samples. In the case of allogeneic, cultured postnatal thymus tissue-derived product, there is high likelihood of heterogeneity due to the nature of the tissue and the lot-to-lot variability that can present itself. By examining samples that showed previous positive clinical outcomes (here defined by survival) and comparing to tissues that were degraded, the appropriate level of differentiation can be determined.

A training set may be selected that contains the most information relating to clinical outcomes. Initially, samples are included from various representative R&D studies as well as multiple forced degradation conditions and clinical samples. These data may be clustered into good and bad groups. The training set may be deemed most informative if restricted to known "good" and known "bad" samples that are representative of future in-process samples to be examined for lot release. This step restricts the samples in the following manner.

Samples may be removed if they were not from the mid-point or Day 5-9 of the culture period. In the example of allogeneic cultured thymus tissue-derived tissue, this is when in-process samples for lot release based on quantitative histology may be taken. Samples may also be removed if they were from R&D lots that are believed to be representative but there are no associated clinical outcomes to examine. Furthermore, samples may be removed if they were associated with negative clinical outcomes. Samples may also be removed from the forced degradation arm if orthogonal methods were unable to confirm degradation.

The underlying data may be grouped to better understand what underlying features result in the various clusters. Groups may be associated with positive clinical outcomes and forced degraded samples and/or tissues associated with negative clinical outcomes. Different parameters may drive the differentiation of the groups with positive clinical outcomes (e.g. mid-sized area, high circularity, and high perimeter) from forced degraded samples and/or negative clinical outcomes.

For example, a group may be characterized by a larger proportion of nuclei that have large perimeters, high integrated densities, and high area with lower circularity. This may be due to the presence of clumps of nuclei that cannot be read as independent cells by the software. This would more likely occur in tissues that still have larger number of thymocytes present in the earlier days of the culture period.

Additional groups may be defined that have positive clinical outcomes. For example groups may be designated by having large numbers of cells with high circularity values and/or higher area when compared to other groups and/or mid-range integrated density. These values are expected for healthy viable tissues in the mid-range of the culture period. Histograms of the measurements of area, circularity, integrated density and perimeter may be constructed from the data.

For comparison a forced degradation study may be conducted where the samples are placed back in thymus organ medium (TOM) prior to the samples being removed on days 5 and 9. This shows how hardy allogeneic cultured postnatal thymus tissue-derived product is to variations in process conditions. Not all culturing condition may cause degradation detectable via any of the measures used. It is believed that these conditions do not permanently damage the tissue to a point where it was either not functional or not viable. As would be expected of degraded samples, there are large proportions of cells with lower circularity, and low area and higher perimeters. This shows cells that are no longer able to maintain viability and are therefore changed in morphology and shrinking with shriveled edges. To show the similarity within a group, analysis of the variability for each group is examined; "good" and "bad" (pass versus fail) classifications may be determined. Using the foregoing steps, the analysis of tissue specimens associated with pass and fail characteristics may be assessed.

EXAMPLES

Allogeneic, cultured postnatal thymus tissue-derived product (e.g., "RVT-802") is typically cultured from 12 to 21 days prior to implantation into the recipient. This culturing time period historically has been demonstrated to result in positive clinical outcomes following implantation of the tissue-engineered product. Not intending to be bound by theory, this culturing time period is believed to allow the tissue to deplete thymocytes either through washing them out of the tissue or through apoptosis. Thymic epithelial cells are maintained through the culture time.

The validated assay examines a sample taken from between days 5-9 of culture to assess the suitability of the cultured thymus tissue for release. To help understand the product better and to better assess the discerning capabilities of the assay, samples were run through the software program taken from days 1 to 21 and beyond and the resulting data were compared to each other to assess what trends were apparent.

FIGS. 14A-14D depict three batches of clinical cultured thymus tissue samples (FIGS. 14A-14C) and a degraded thymus tissue sample. The four features of area, perimeter, integrated density, and circularity for the sample depicted in FIG. 14A were: area=11.34; circularity=0.696; perimeter=14.310 and integrated density=1889.2. The four features of area, perimeter, integrated density, and circularity for the sample depicted in FIG. 14B were: area=11.41; circularity=0.993; perimeter=11.982 and integrated density=1912.4. The four features of area, perimeter, integrated density, and circularity for the sample depicted in FIG. 14C were: area=10.53; circularity=0.846; perimeter=12.510 and integrated density=1707.4. The four features of area, perimeter, integrated density, and circularity for the sample depicted in FIG. 14D were: area=13.0; circularity=0.352; perimeter=21.556 and integrated density=1786.0. A single nuclei in each image is identified by a circle.

Figure 15:
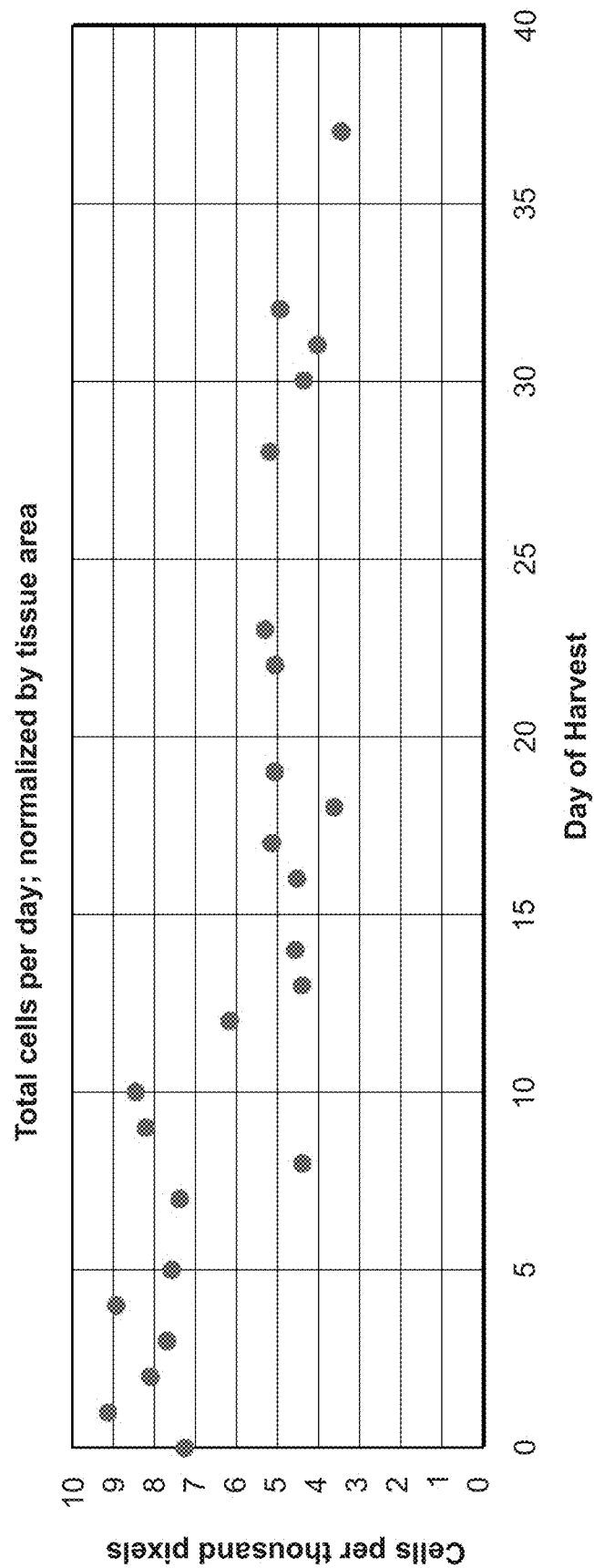
FIG. 15 illustrates the trend of number of cells per day normalized for tissue area.
Figure 16A:
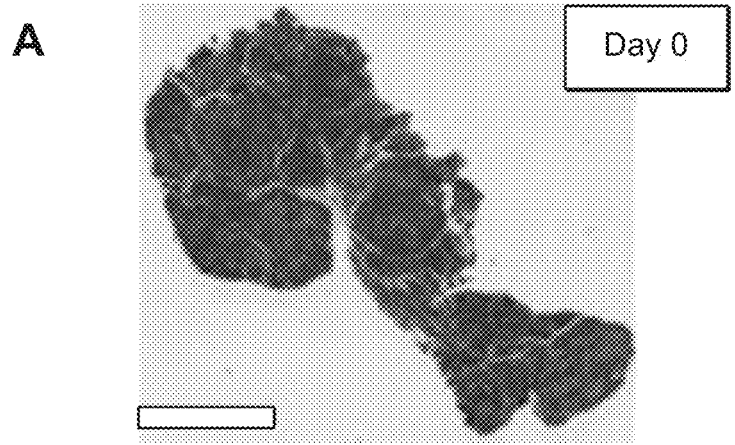
FIGS. 16A-16B are images of thymus tissue at Day 0 of the culturing process.
Figure 16B:
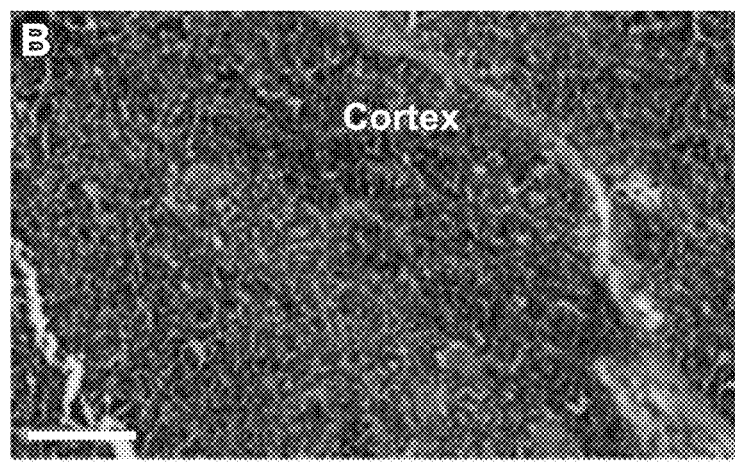

The overall trend in the number of nuclei detected was also examined, this is expected to decrease over time as thymocytes wash out of the tissues or undergo apoptosis which can be observed in FIG. 15. These data were normalized for tissue area as different slices from multiple lots were examined on the different days; tissue section size can differ between slices and can cause variability in the data set, but a general negative trend was seen with increasing culture days, with a visual step change in the data around day 10. Previous data has shown that the majority of thymocyte depletion is earlier in the culture period when compared to the decrease in the total number of cells shown below.

Example 1. Time Course Studies of Cultured Thymus Tissue

The general appearance of the tissue, and consequently the histology slides, changes over the course of the culture period. Images presented in FIGS. 16A-B, 17A-B, 18A-B, 19A-B and 20A-B show the differences in appearance of the cultured thymus tissue in H&E stained slides at various time intervals, namely at 0, 5, 9, 12 and 21 days. The images are presented at 40× magnification. The days chosen for these images and further analysis are from days that have been identified as important from a manufacturing process perspective. Day 0 represents the incoming tissue. Histology at Day 0 is taken for identity purposes. Both the Day 0 and Day 5-9 histology samples were formalin fixed and taken to the pathology laboratory for paraffin embedding and sectioning. The sections were stained and assessed by a board certified pathologist.

Figure 21A:
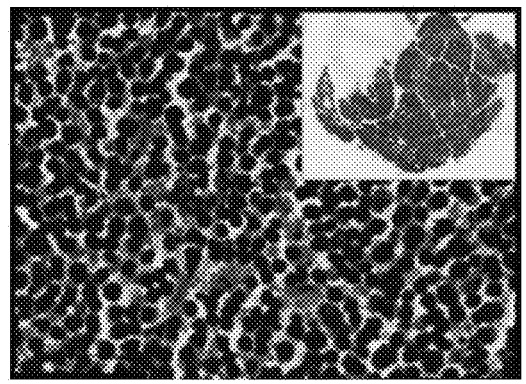
FIGS. 21A-21E are images of H&E stained cultured thymus tissue at 0, 5, 9, 2 and 21 days depicting changes in the appearance of nuclei at Day 0, 5, 9, 12 and 21.
Figure 21B:
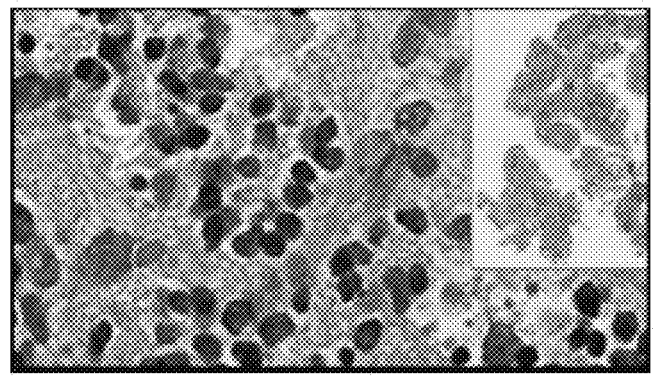
Figure 21C:
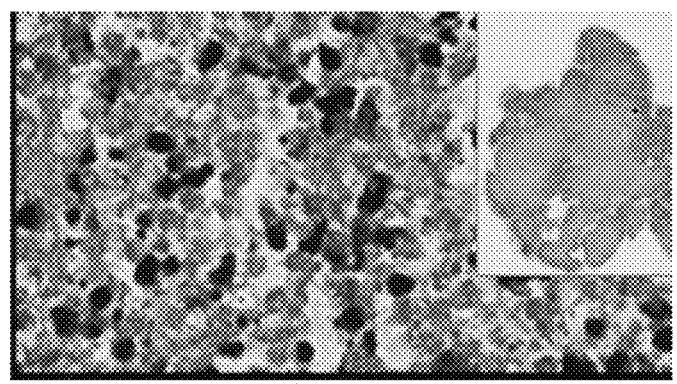
Figure 21D:
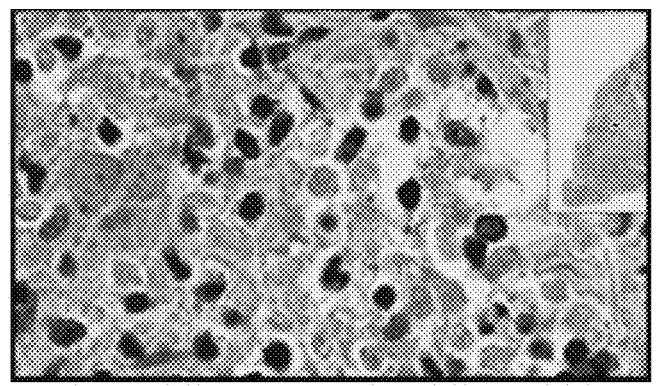
Figure 21E:
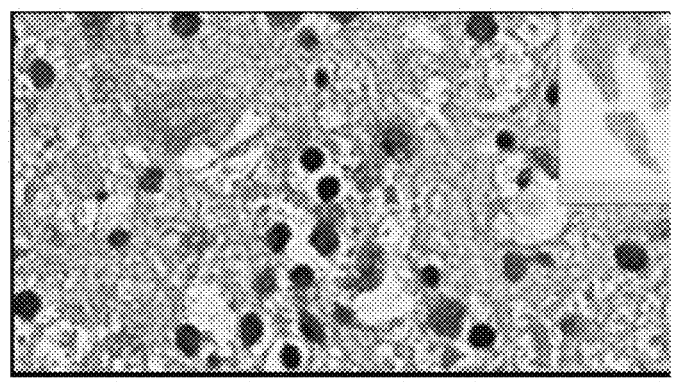

FIGS. 21A-21E are images of H&E stained cultured thymus tissue at 0, 5, 9, 2 and 21 days depicting changes in the appearance of nuclei at Day 0, 5, 9, 12 and 21. FIG. 21A shows a high proportion of the nuclei have a higher integrated density indicative of a high number of thymocytes. As thymocytes are washed out of the tissue, the tissue at Day 5 (FIG. 21B), 9 (FIG. 21C), 12 (FIG. 21D) and 21 (FIG. 21E) show a marked decrease in integrated density and a profile more similar to the profile for thymic epithelial cells.

Figure 22:
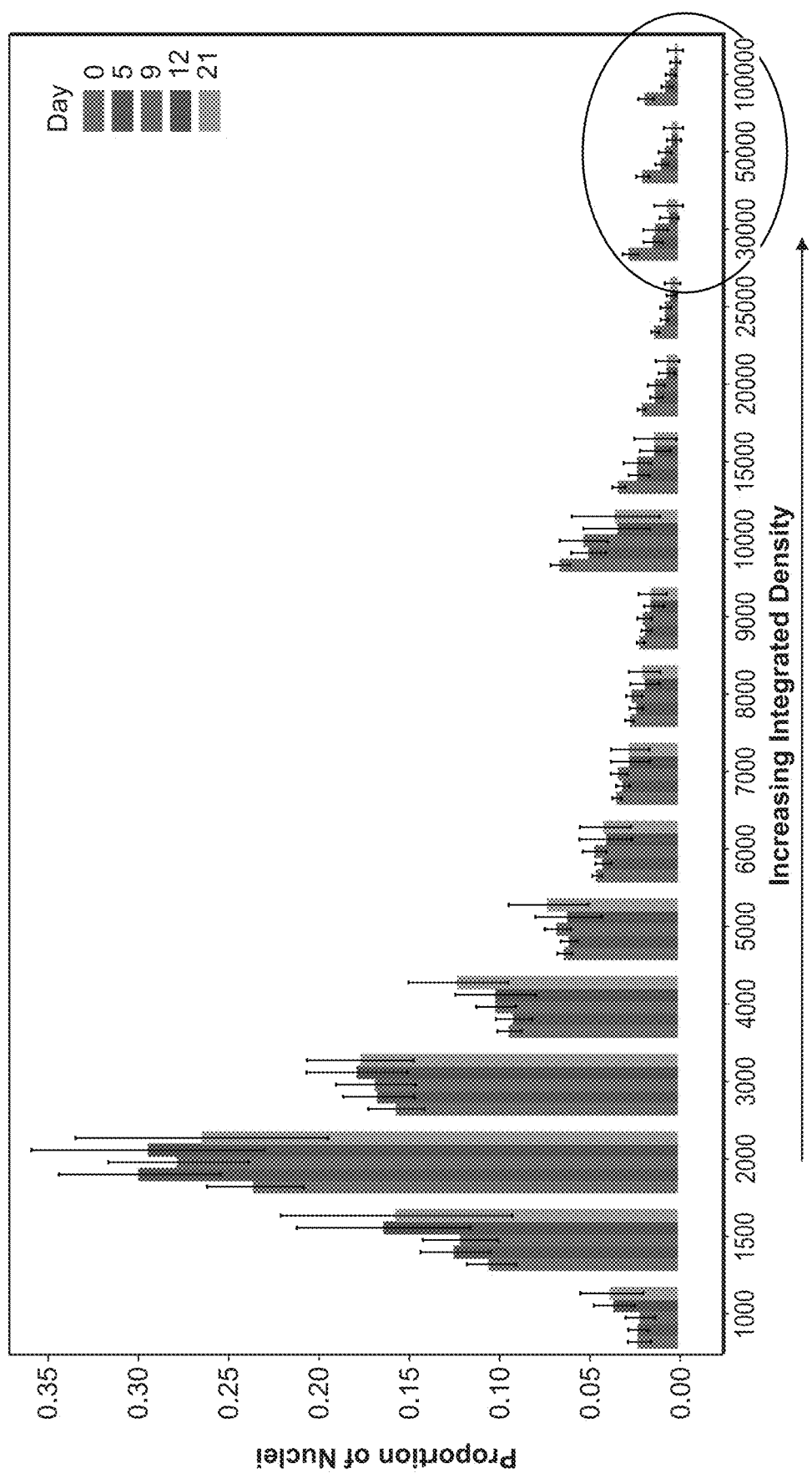
FIG. 22 is a graph showing the time course of integrated density determinations from technical batches of allogeneic cultured postnatal thymus tissue-derived product. As thymocytes are washed out of the tissue, the tissue at Day 5 shows a marked decrease in integrated density and a profile more similar to the profile for thymic epithelial cells. Error bars are one S.D. from the mean.

FIG. 22 shows the time course of integrated density determinations from technical batches of allogeneic cultured postnatal thymus tissue-derived product. As thymocytes are washed out of the tissue, the tissue at Day 5 shows a marked decrease in integrated density and a profile more similar to the profile for thymic epithelial cells. Error bars are one S.D. from the mean.

Figure 23:
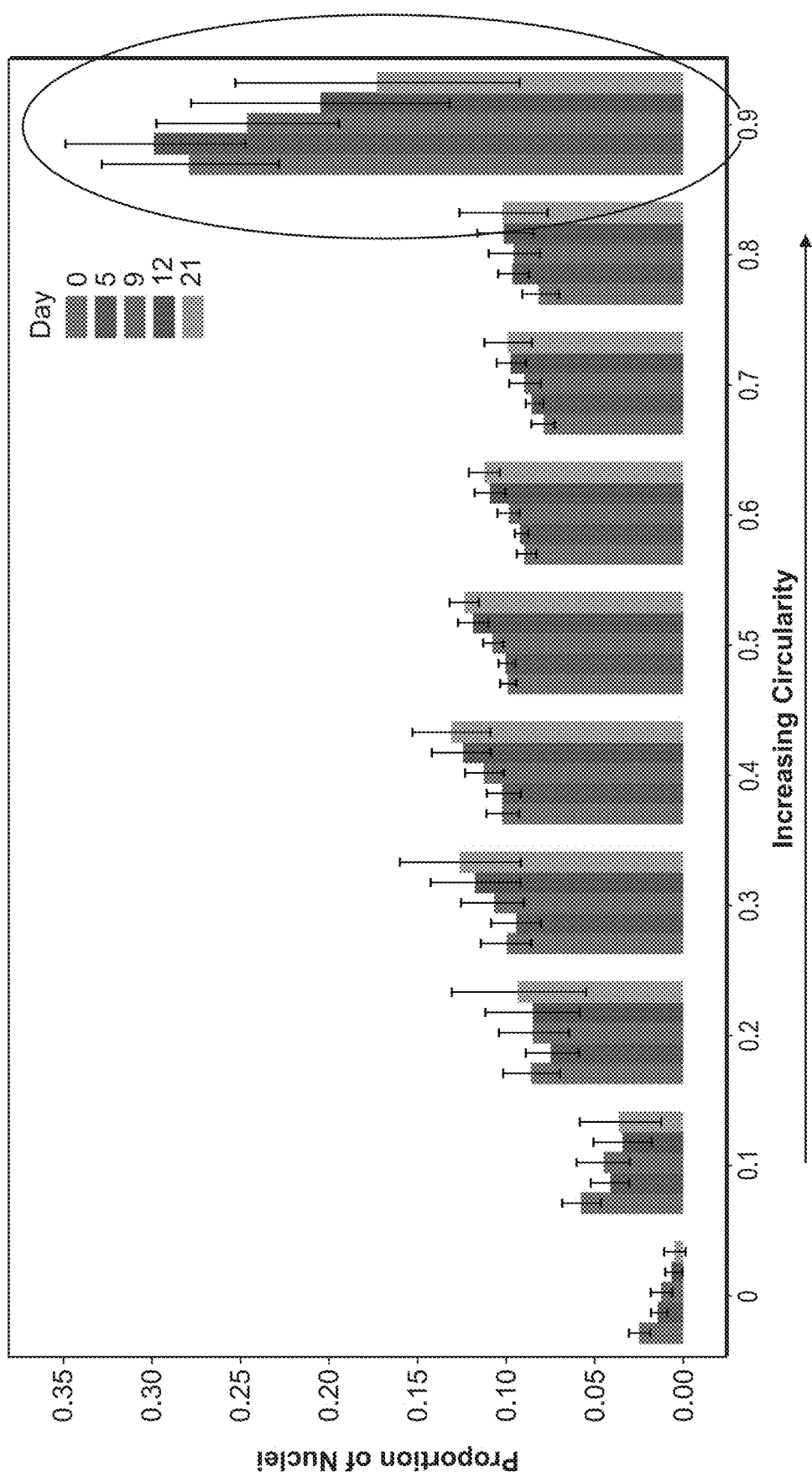
FIG. 23 is a graph showing measurements of circularity. The number of cells with very high circularity diminishes over time throughout the culturing process. This is likely due to apoptosis resulting in nuclei that are less circular as well as washing out of the very circular thymocytes. For samples at Day 0 with lower circularity it is likely due to clumping of thymocytes being measured as a single entity with lower circularity than a single nuclei. Error bars are one S.D. from the mean.

FIG. 23 shows measurements of circularity. The number of cells with very high circularity diminishes over time throughout the culturing process. This is likely due to apoptosis resulting in nuclei that are less circular as well as washing out of the very circular thymocytes. For samples at Day 0 with lower circularity it is likely due to clumping of thymocytes being measured as a single entity with lower circularity than a single nuclei. Error bars are one S.D. from the mean.

Figure 24:
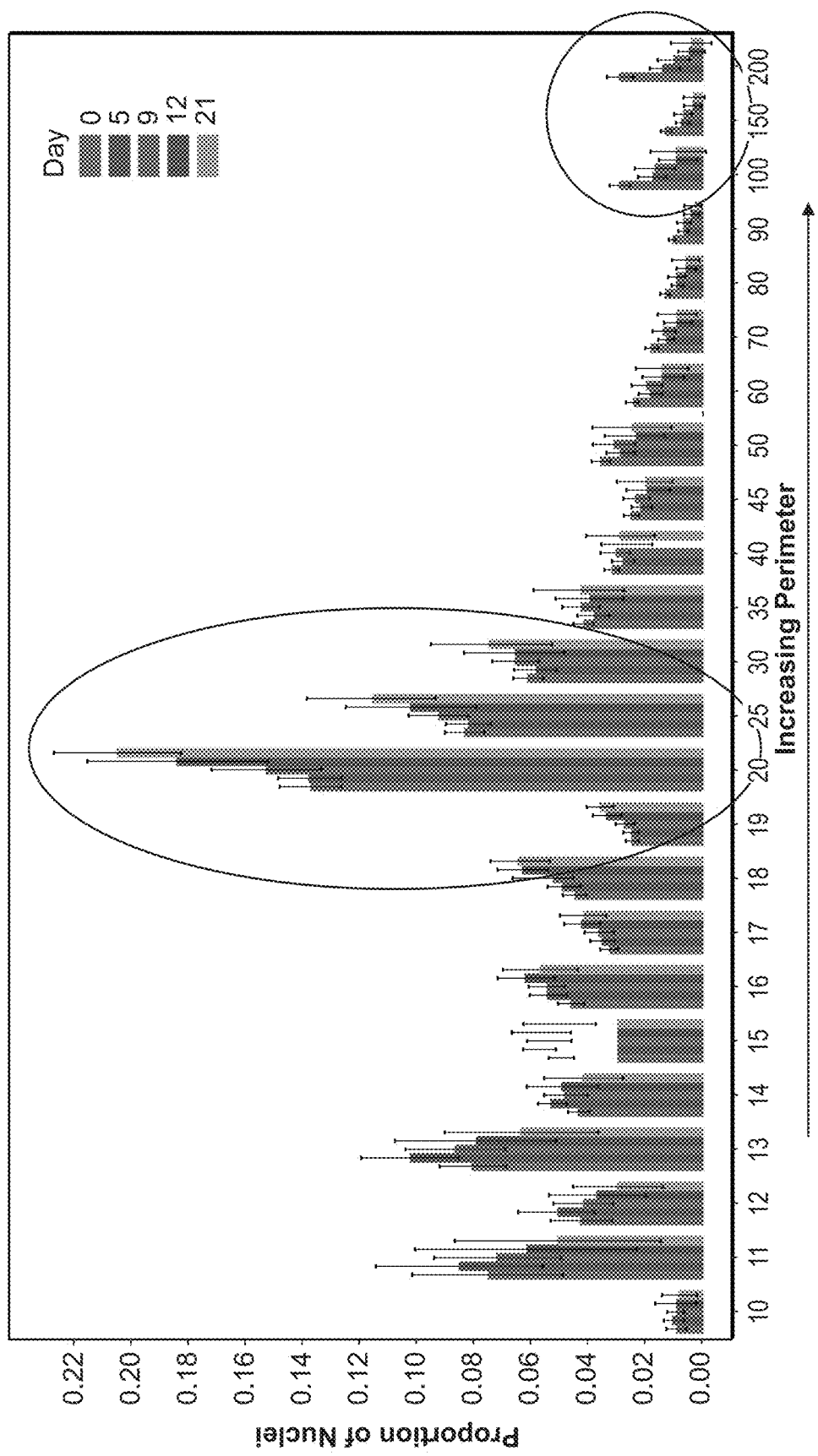
FIG. 24 is a graph showing measurements of perimeter. At Day 0 At Day 0 there are a large proportion of cells with high perimeters, which is likely due to clumps of cells being read in the program as a single shape resulting in the large perimeter values. The increase in perimeter is likely a combination of the thymocyte washing out as well as cells undergoing apoptosis over culture time and a resulting increase in perimeter from that event. Error bars are one S.D. from the mean.

FIG. 24 shows measurements of perimeter. At Day 0 there are a large proportion of cells with high perimeters, which is likely due to clumps of cells being read in the program as a single shape resulting in the large perimeter values. The increase in perimeter is likely a combination of the thymocyte washing out as well as cells undergoing apoptosis over culture time and a resulting increase in perimeter from that event. Error bars are one S.D. from the mean.

Figure 25:
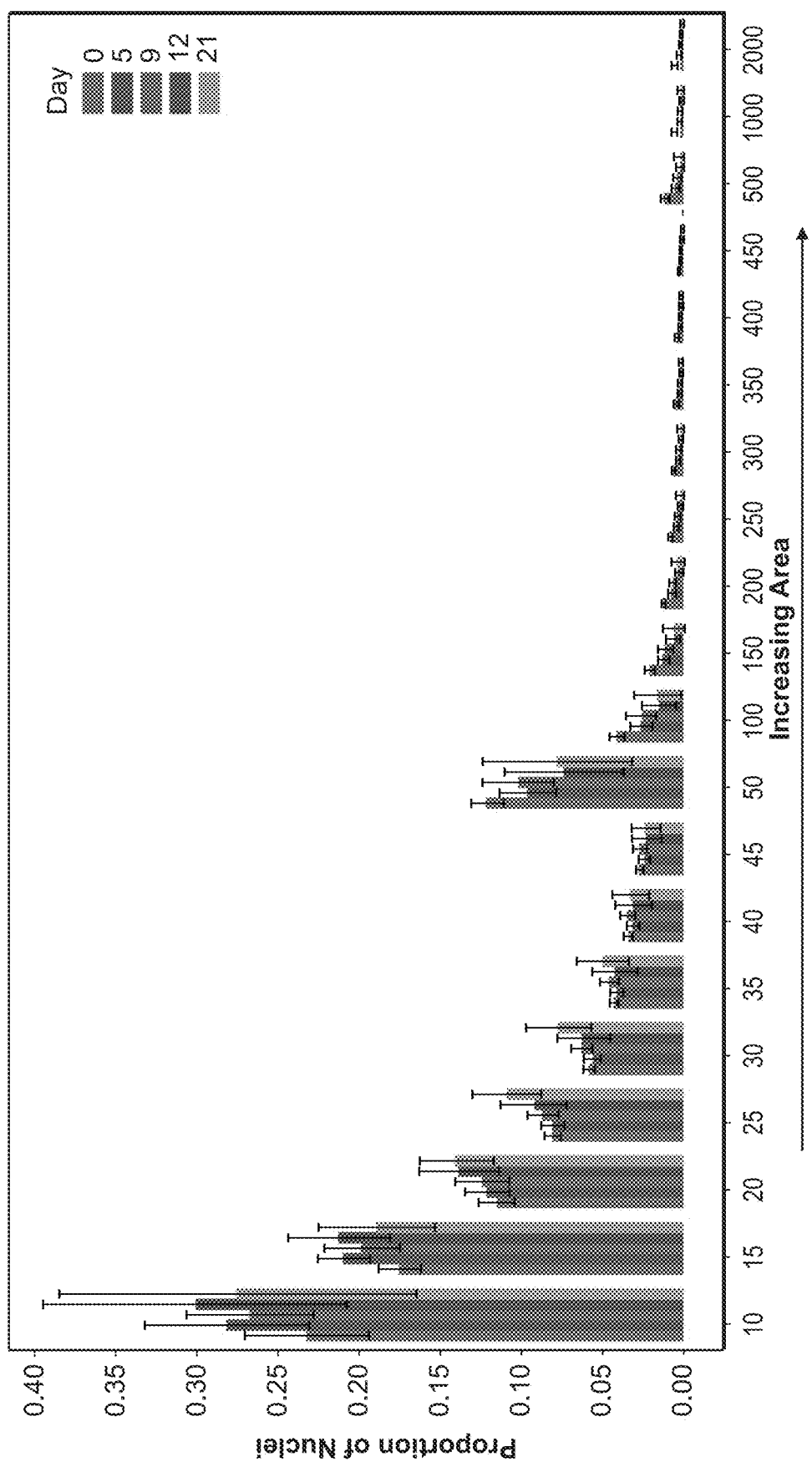
FIG. 25 is a graph showing the time course of area. This technique used the Euclidean distance (the square root of the sum square of error between a sample and the grand centroid) to measure the similarity between two samples when taking into account all four variables examined. For reference, the lower the Euclidean distance, the more similar two samples are to each other. Error bars are one S.D. from the mean.

FIG. 25 shows the Euclidean distance (the square root of the sum square of error between a sample and the grand centroid) to measure the similarity between two samples when taking into account all four variables examined. For reference, the lower the Euclidean distance, the more similar two samples are to each other. Error bars are one S.D. from the mean.

Figure 26:
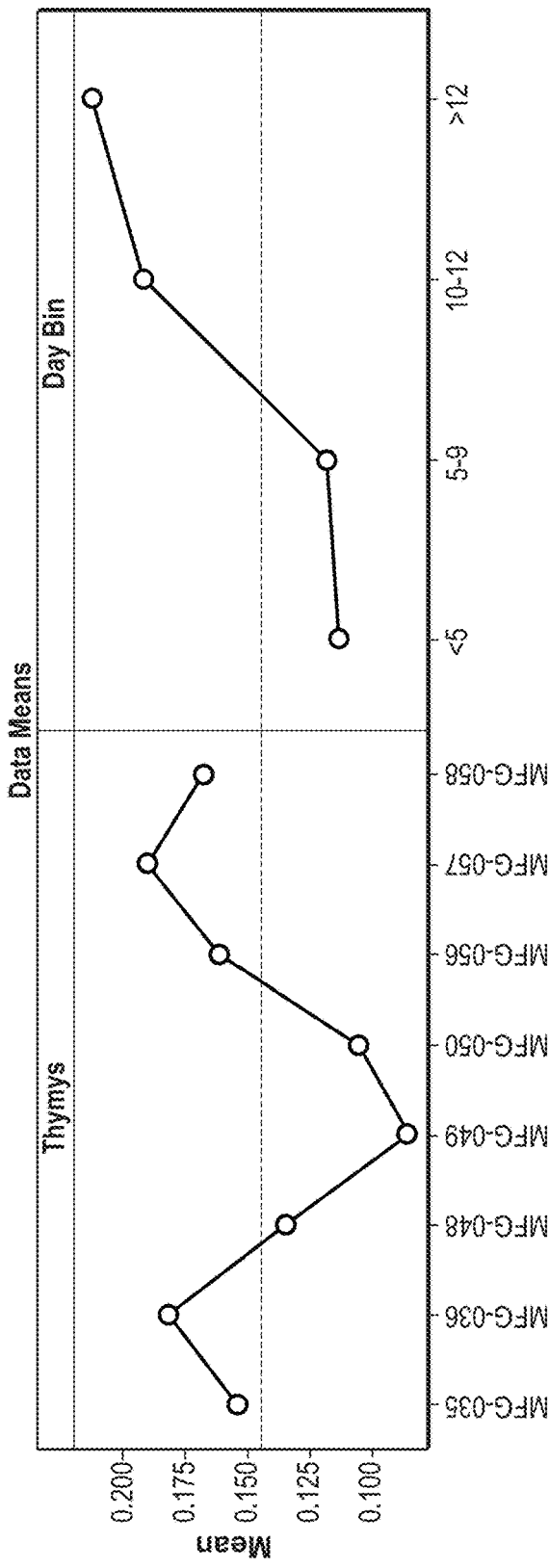
FIG. 26 is a main effects plot and interaction plot of the data. The data shown in FIG. 26 confirms that cultured thymus tissue behaves similarly over time.
Figure 26:
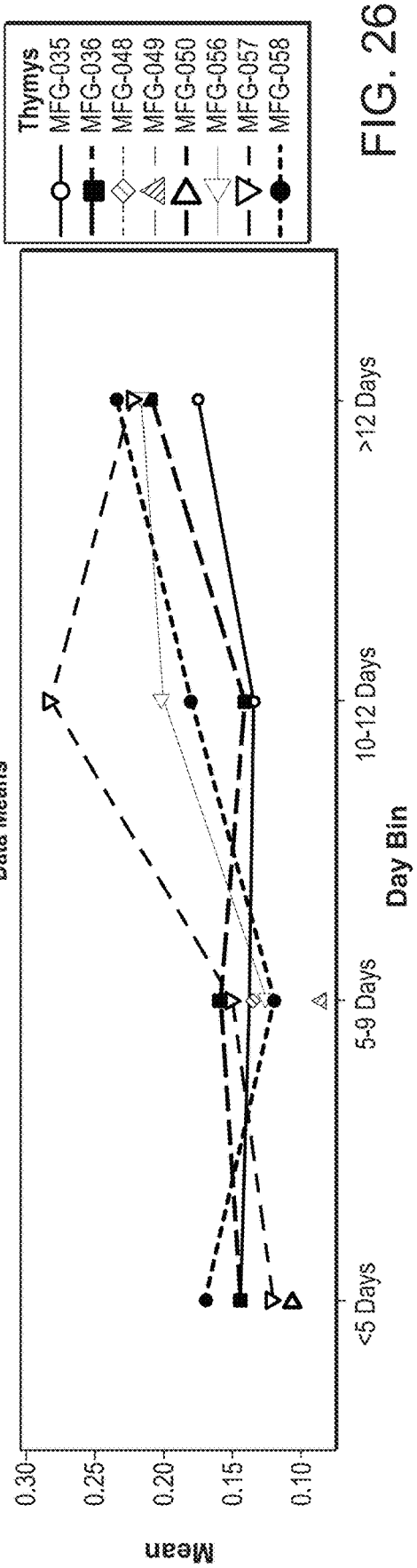

FIG. 26 is a main effects plot and interaction plot of the data. The data shown in FIG. 26 confirms that cultured thymus tissue behaves similarly over time.

Overall, nuclear characteristics over the course of culture time aligns with theoretical expectations for trends. Most of the apparent shifts in the data are prior to the intended release days of the lots. This suggests that many of the changes in occur during the initial days of culture, after which the environment is able to be sustained for up to 21 days. This is supportive of the assay to detect true trends in the cell populations and how they change over time.

Example 2: Inter-Thymus Variability Study

Inter thymus variability was examined to better understand if samples are similar between thymuses. Inter thymus variability was assessed in a similar manner to intra thymus variability where samples examined are from a single day, but instead of being restricted to a single thymus, include samples across lots. The Euclidean distance of each sample was calculated to the center point of all samples within the isolated data set. ANOVA's were then performed on the distances to center by thymus. This analysis was performed on samples on Days 5 and 9.

Inter thymus variability was examined to better understand if samples are similar between thymuses. Inter thymus variability was assessed in a similar manner to intra thymus variability where samples examined are from a single day, but instead of being restricted to a single thymus, include samples across lots. The Euclidean distance of each sample was calculated to the center point of all samples within the isolated data set. ANOVA's were then performed on the distances to center by thymus. This analysis was performed on samples on Days 5 and 9.

Figure 27:
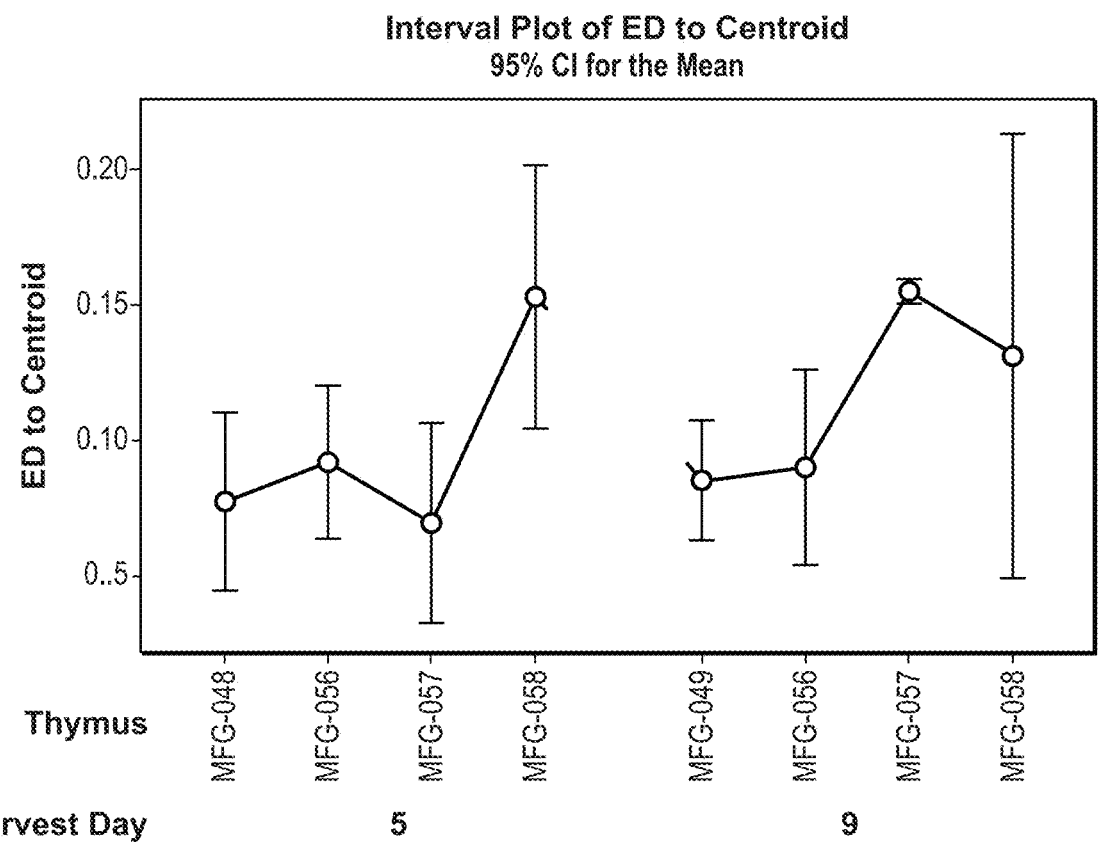
FIG. 27 is a graph showing 95% confidence intervals of distance from centroid by thymus per day.

From Table 6 below, there is no detectable differences between lots at Day 9. There are slight statistical differences between thymuses at Day 5. It is hard to determine if these result in practical differences that result in differences in product quality. To assess this in a different manner, 95% confidence intervals at each day were generated per thymus. As can be seen in FIG. 27, batch MFG-058 does not overlap the confidence intervals for the other tissues on Day 5, but does by Day 9. This lot was manufactured in a representative manner to the other lots, and no differences were observed via gross histological examination at either day. As such, it is likely that this is an artifact of the sensitivity of the method to slight differences in nuclear distributions between tissues.

TABLE 6

ANOVA analysis of inter thymus variability, analysis performed by thymus to center point of the day group

| Day | Thymus | Number of Samples | Between Difference Detected? | Within Variability Detected? |
|---|---|---|---|---|
| 5 | MFG-048 | 8 | Yes | No |
|  | MFG-056 | 11 |  |  |
|  | MFG-057 | 4 |  |  |
|  | MFG-058 | 5 |  |  |
| 9 | MFG-049 | 20 | No | No |
|  | MFG-056 | 11 |  |  |
|  | MFG-057 | 3 |  |  |
|  | MFG-058 | 6 |  |  |

Example 3: Thymic Epithelial Cell Analysis

Figure 28A:
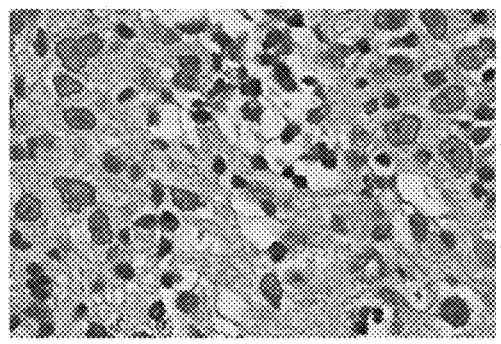
FIGS. 28A and 28B are exemplary images of thymic epithelial cells, which have been outlined in red by a pathologist.
Figure 28B:
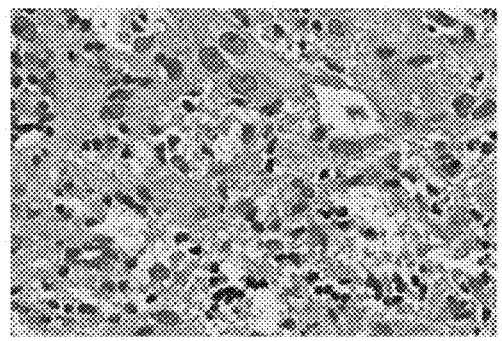
Figure 29:
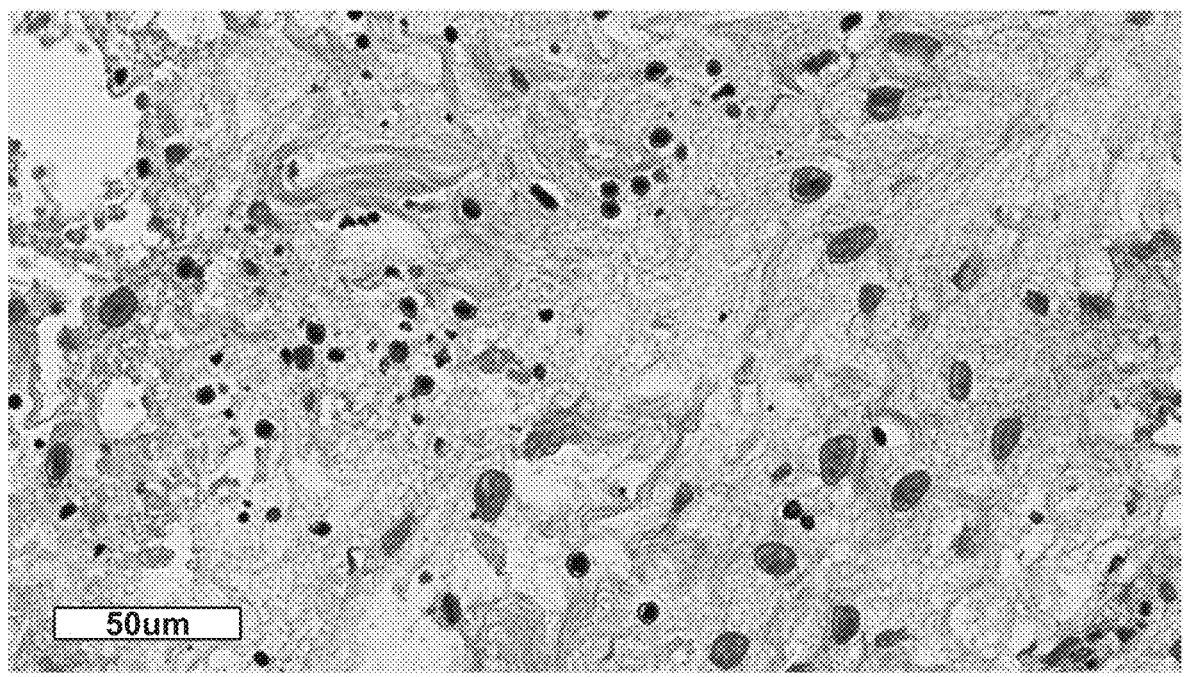
FIG. 29 is an image of thymic epithelial cells (TECs) outlined in red by a pathologist. Thymocytes are outlined in blue.

A more specific analysis of only thymic epithelial cells was performed to help characterize the allogeneic, cultured postnatal thymus tissue-derived product. Thymic epithelial cells are hypothesized to be critical for the mechanism of action of the allogeneic, cultured postnatal thymus tissue-derived product. Images were sent to a pathologist. The pathologist selected nuclei for cells identified as thymic epithelial cells (refer to FIGS. 28A-B). The nuclei of thymic epithelial cells differ from other cells in the tissue population. TECS are generally larger, and have a nucleolus present, which appears as a darker purple dot within the center of the lighter purple outer nucleus in FIGS. 28A-B.

Known marked cells were extracted as individual data points from the software. Using this data, a filter was devised to enable the following steps to be performed in sequential order. Two size filters remove any cells outside of the size range window both pre- and post-splitting of conjoined cells. The following filtering steps were carried out.

The darkest cells were removed from the dataset by defining threshold of inclusion below darkest pixels (included pixels between 100-130 to 150-180 pixel intensity dependent on staining intensity).

Cells below 50 $\mu m^2$ in area were removed.

Holes were filled, watershed applied to split conjoined cells.

Cells outside range of 30-250 $\mu m^2$ and circularity <0.75 were filtered out of the dataset.

Figure 30:
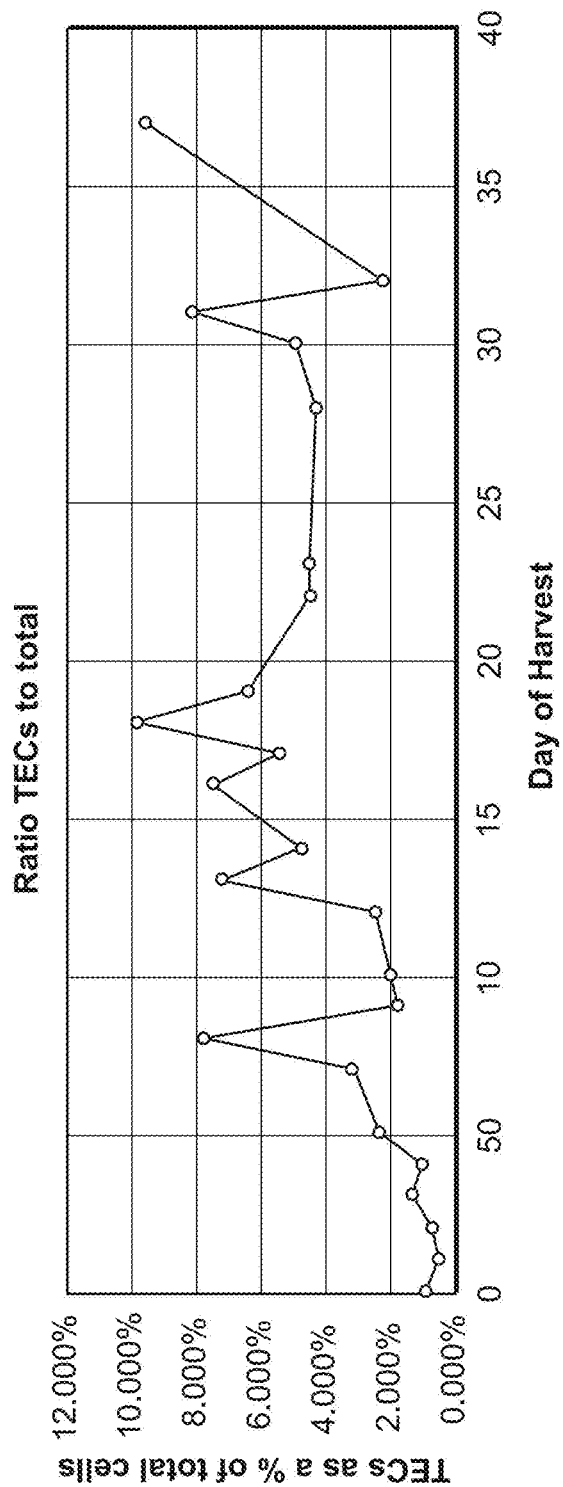
FIG. 30 is a plot of the ratio of TECs to the total number of cells from the H&E slides.
Figure 31:
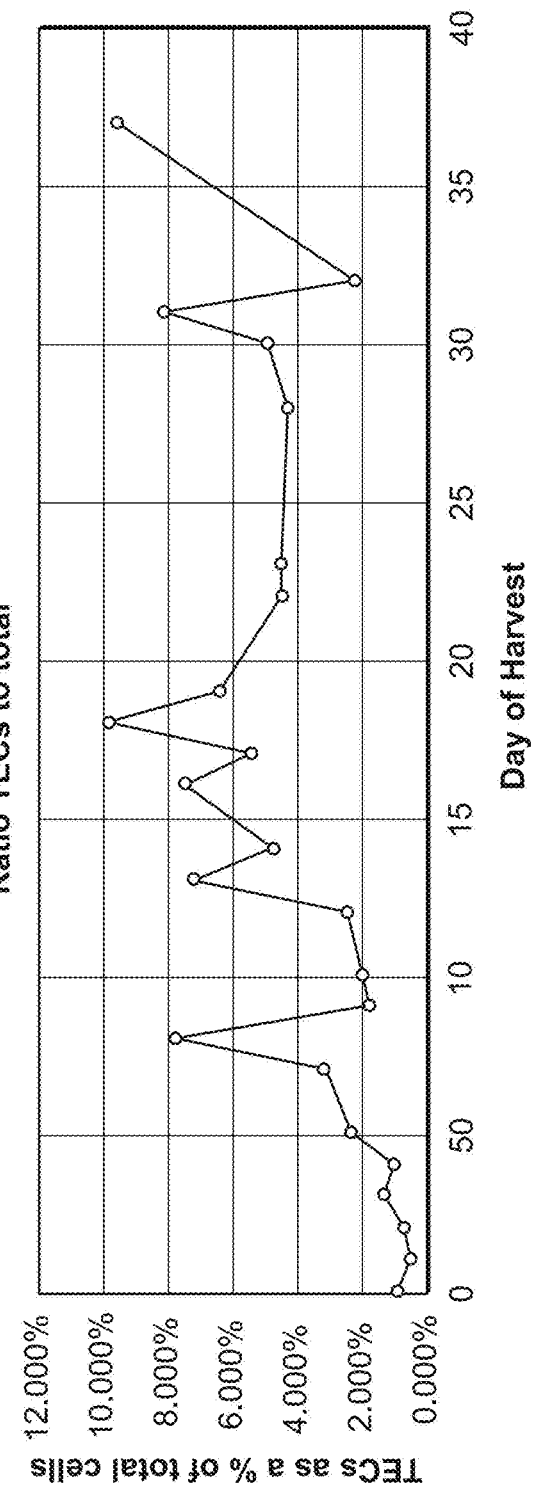
FIG. 31 is a plot of the ratio of TECs to the total number of cells normalized for the selected tissue area.

The foregoing filters permitted analysis of images with data sets generated and restricted to characterize the TEC cells. When examining the total proportion of cells in the tissue over the course of the culture period, there is a general increase in TECs. The increase in TECS is because, as the thymocytes are washed out of the tissue, a larger number of the remaining cells are TECs. This change can be visualized in FIG. 30: Ratio of TECs to the total number of cells from H&E slides. These determination also show that the TECs are maintained throughout the culture period as would be required for the efficacy of the product. The same trend can be seen when normalized for tissue area as exhibited in FIG. 31. Data for classifying and extracting TECs from the analysis set was done on one sample per day and subject to sample to sample variability.

Example 4: Thymocyte Analysis

Figure 17A:
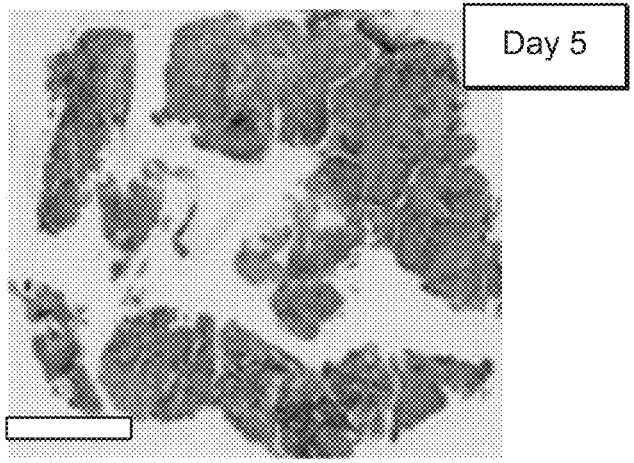
FIGS. 17A-17B are images of thymus tissue at Day 5 of the culturing process.
Figure 17B:
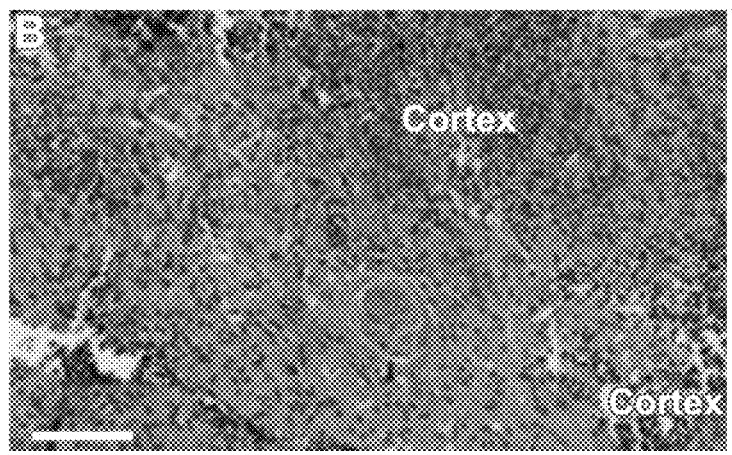
Figure 18A:
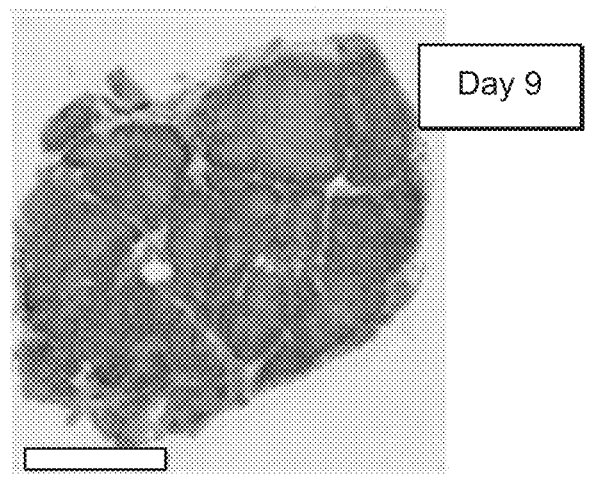
FIGS. 18A-18B are images of thymus tissue at Day 9 of the culturing process.
Figure 18B:
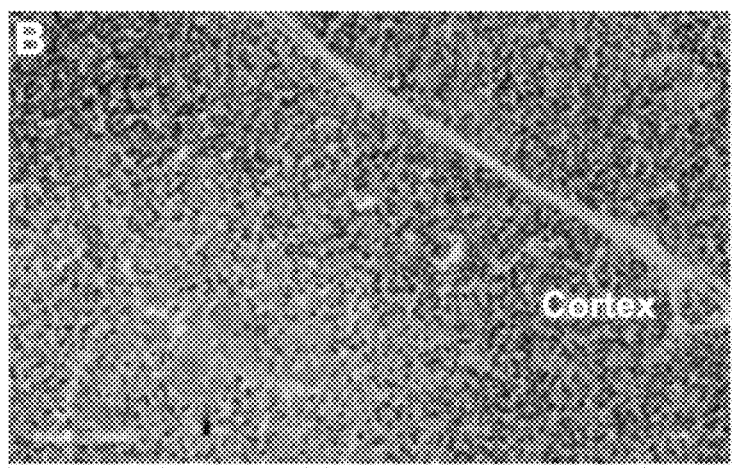
Figure 19A:
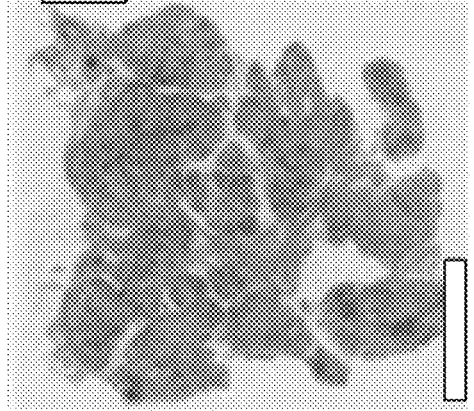
FIGS. 19A-19B are images of thymus tissue at Day 12 of the culturing process.
Figure 19B:
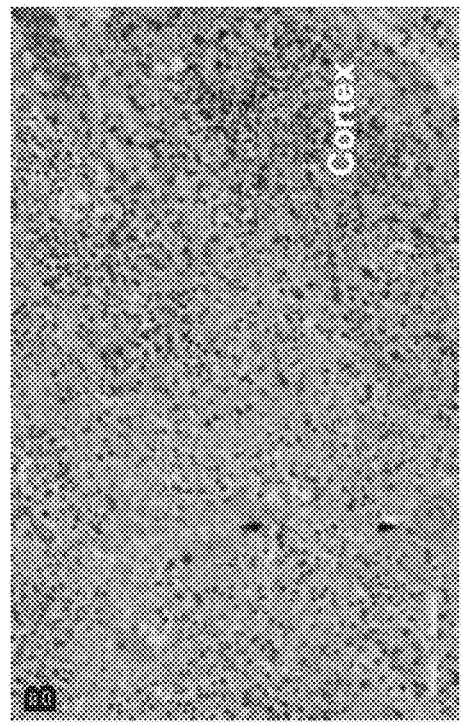
Figure 20A:
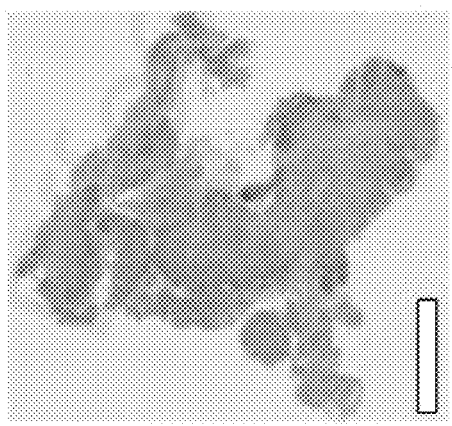
FIGS. 20A-20B are images of thymus tissue at Day 21 of the culturing process.
Figure 20B:
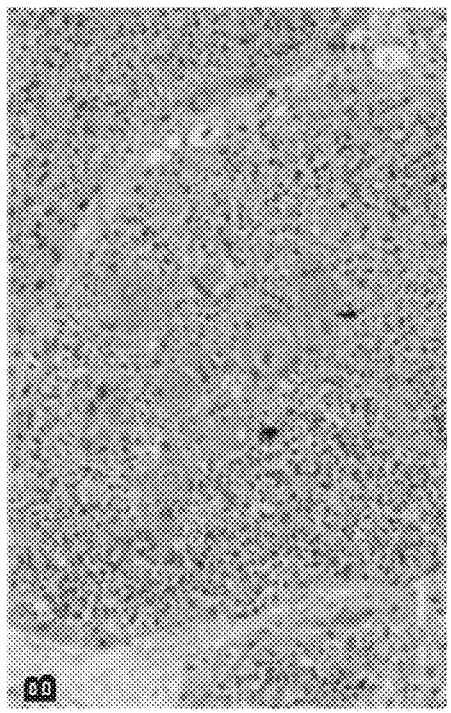

The TEC analysis of Example 3 also gives a better view of the trends of the thymocytes washing out of the tissue through the culture period. A similar analysis was not performed for the thymocytes, but it can be inferred from the above data, that the number of thymocytes is reduced during the course of the culture as the ratio of TECs increase. This change can also be visualized in images of the H&E stained slides at multiple magnifications (See, for example, FIGS. 16 to 21). The thymocytes in these images are the smaller dark purple nuclei. In the day 0 images of FIGS. 16A and 16B, they are numerous, and by Day 5 there is a marked decrease, as shown in FIGS. 17A and 17B. This has been noted in numerous pathology reports as well as in cytokine and chemokine analysis of L-Selectin, a thymocyte marker (REP-016). Overall data trends also agree with this analysis using the quantitative analysis as previously discussed.

Example 5: Hierarchal Cluster Analysis

Figure 32:
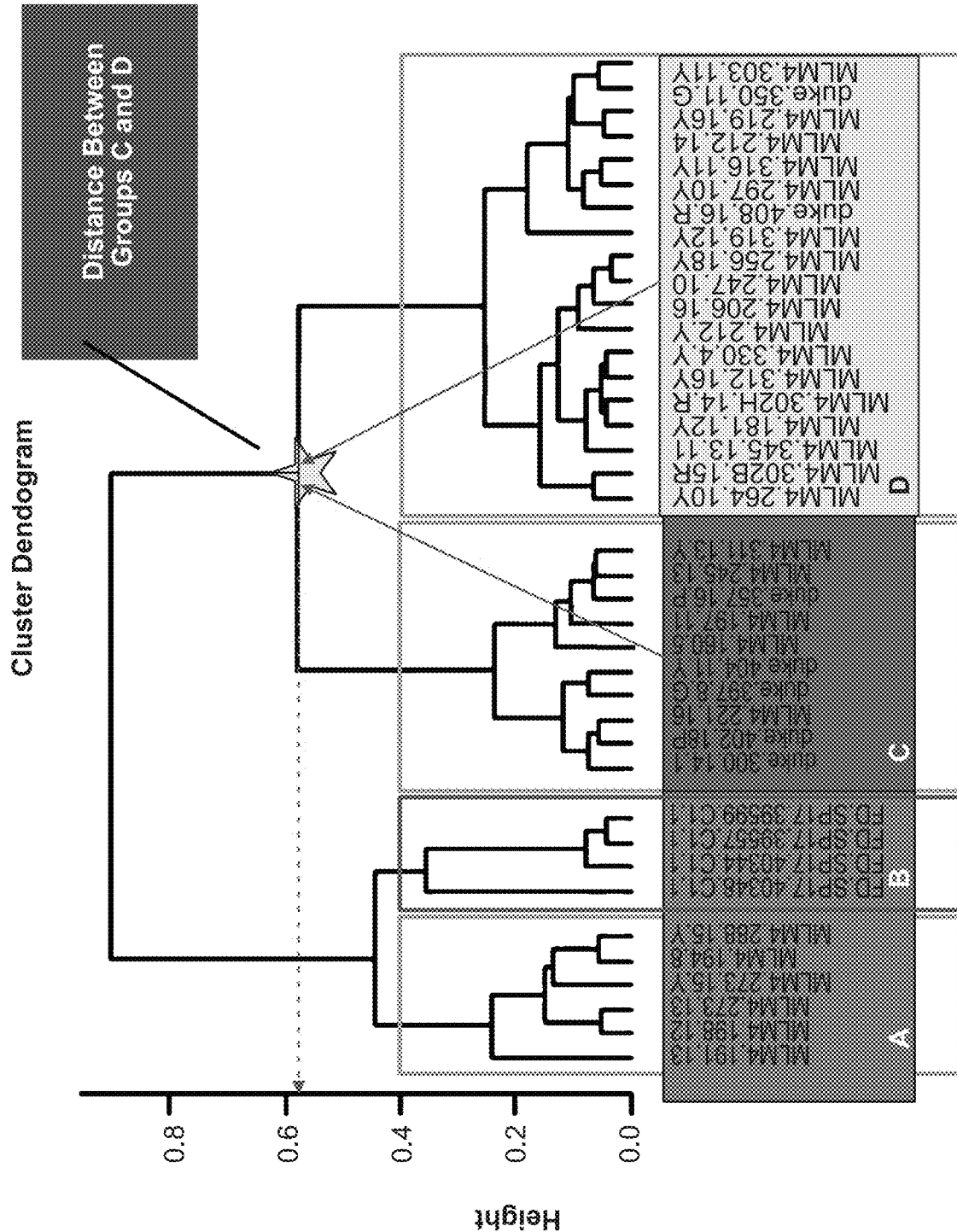
FIG. 32 is cluster dendrogram showing the distance between groups "C" and "D" as an example. The highlighted green and red boxes indicate single groupings. This is based on a cutoff y-axis height of 0.43. In this example, groups C and D are at a distance of 0.6 and therefore are considered to be two separate groups. Samples within each group are considered to be statistically similar while those in different groups are considered statistically different.

The data presented in Examples 1-4 shows the samples broken into 4 groups as illustrated in FIG. 32. The groups depicted in FIG. 32 were generated through hierarchal cluster analysis. This analysis systematically and statistically identifies samples with similar characteristics by iteratively grouping data based on similarities resulting in meaningful clusters of data of similar properties (referred to as "groups"). The process for grouping cells required the following steps:

The distance between groups is calculated. Distance is a measure of similarity between groups.

The cost: of joining two groups is calculated. The cost here is how much error is added by joining the groups.

The groups that have the least merging cost are joined.

The process is repeated until all data are joined into one group.

The resulting data set essentially shows a family tree of how "related" or similar the samples are to each other. The height between the branches shows how related two groups are to each other. Distance on the horizontal x-axis does is not indicative of any closer relationship. Refer to FIG. 32 for an illustration of this. FIG. 32 is cluster dendrogram showing the distance between groups "C" and "D" as an example. The highlighted green and red boxes indicate single groupings. This is based on a cutoff y-axis height of 0.43. In this example, groups C and D are at a distance of 0.6 and therefore are considered to be two separate groups. Samples within each group are considered to be statistically similar while those in different groups are considered statistically different.

To determine where the cut height is between the different groups, a Screen Plot can be used to examine where the distances between the groups are most significant. This ensures that minimal differences between samples do not overly influence the algorithm. Too small of differences will result in more likely fracturing of future samples into independent groups as the samples have to be too similar to cluster together than is realistic for allogeneic, cultured postnatal thymus tissue-derived product. Alternatively, the groups must have an appropriate cut off to ensure that there is differentiation between samples. In the case of allogeneic, cultured postnatal thymus tissue-derived product, there is high likelihood of heterogeneity due to the nature of the tissue and the lot-to-lot variability that can present itself. By examining samples that showed previous positive clinical outcomes (here defined by survival) and comparing to tissues that were degraded, the appropriate level of differentiation can be determined.

Example 6: Training Set Determination

In a preferred embodiment, a training set was selected that contained the most information relating to clinical outcomes. Initially, samples were included from various representative R&D studies as well as multiple forced degradation conditions and clinical samples. This resulted in a clustering analysis that included many good and bad groups (refer to FIG. 33). After further development of the assay, it was decided that the training set would be most informative if restricted to known "good" and known "bad" samples that are representative of future in-process samples to be examined for lot release. This restricts the samples in the following manner.

Samples were removed if they were not from the midpoint or Day 5-9 of the culture period. This is when in-process samples for lot release based on quantitative histology will be taken.

Samples were removed if they were from R&D lots that are believed to be representative but there are no associated clinical outcomes to examine.

Samples were removed if they were associated with negative clinical outcomes. These samples were not believed to be "bad" as they were released from the facility based on the qualitative histology assay in use, and there were no cases where it was believed that the lot itself was the cause of the clinical outcome. These cases were removed because there is no definitive proof that they did work.

Samples were removed from the forced degradation arm if orthogonal methods were unable to confirm degradation. These samples were examined by a pathologist as well as spent media samples examined for cytokines and chemokines and any sample that was not confirmed to be "bad" by another method was left out of the final training set Allogeneic cultured postnatal thymus tissue-derived product has been shown to be hardy to a variety of conditions, and the analysis should not be skewed to detect for cases that still likely result in "good" tissue. Conditions that remained in the analysis set were from samples that were frozen at −20° C. or where the media was replaced with 10×PBS. For a full listing of degradation conditions and results refer to Table 7.

TABLE 7

Analysis of forced degraded tissues via three methods

| Condition | Time at Condition | Qualitative Histology | Quantitative Histology | Significant Change |
|---|---|---|---|---|
| 55° C. | 4 hrs | No change detected | Clusters with Negative Control | Significant Change |
| −20° C. | 4 hrs | Significant Degradation | Negative Control | Significant Change |
| Media = 10X PBS | 24 hrs | Significant Degradation | Negative Control | Significant Change |
| Media = Saline | 24 hrs | Minimal changes detected | Clusters with Positive Control | Minimal Change |
| | 48 hrs | Minimal changes detected | Clusters with Positive Control/ | Minimal Change |

TABLE 7-continued

Analysis of forced degraded tissues via three methods

| Condition | Time at Condition | Qualitative Histology | Quantitative Histology | Significant Change |
|---|---|---|---|---|
| Media = None (dehydration) | 24 hrs | No change detected | Clusters with Positive Control/Indeterminate[2] | Minimal Change |
| | 48 hrs | No change detected | Clusters with Positive Control | Minimal Change |
| Media = 1% DMSO | 4 hrs | No change detected | Clusters with Positive Control | Minimal Change |
| Room Temperature | 24 hrs | No change detected | Clusters with Positive Control | Minimal Change |

[1]Pathologist determined that this condition likely fixed the tissue.
[2]Indeterminate results caused the groups to shift.

Figure 33:
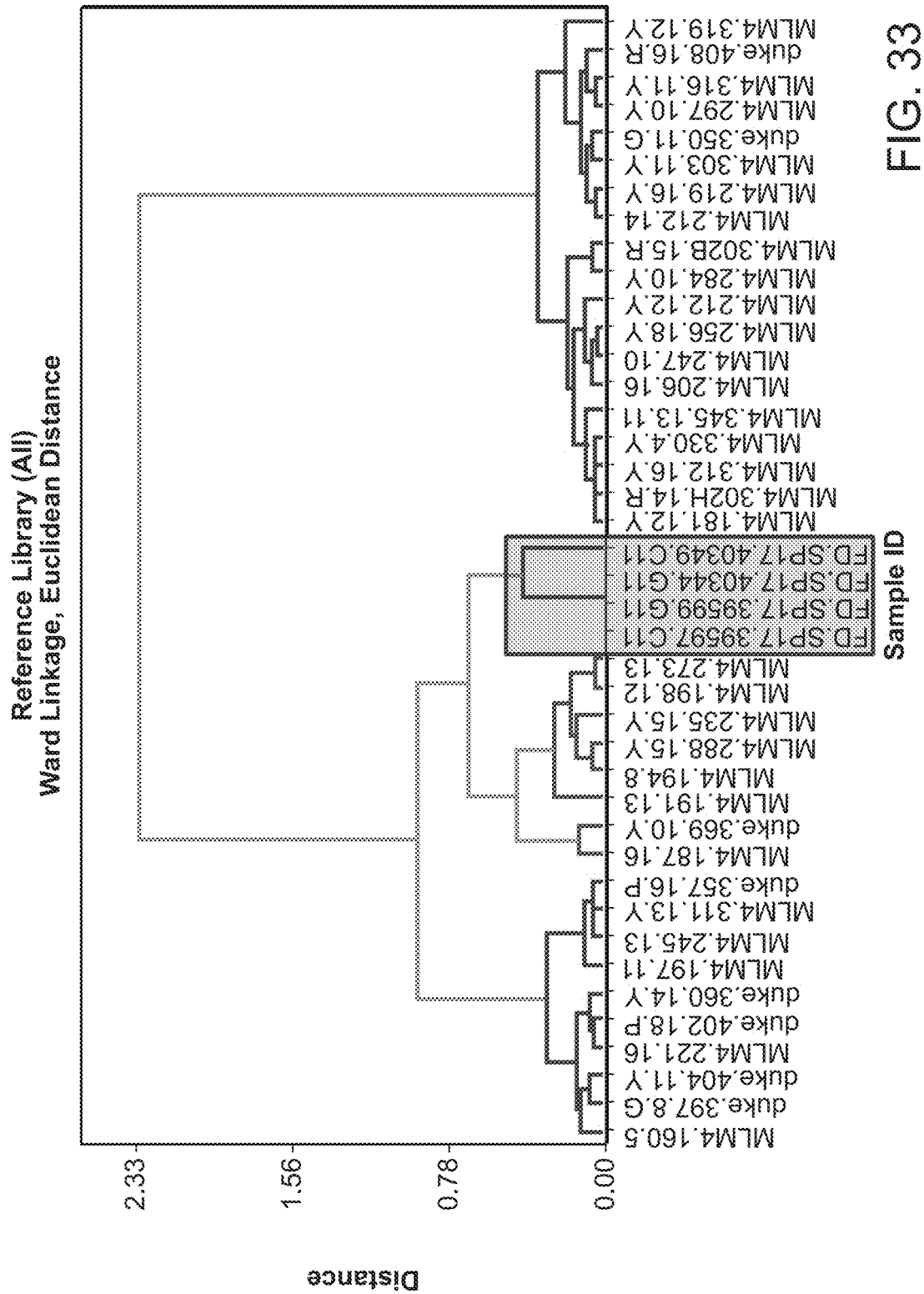
FIG. 33 is a graph showing a training set with all clinically good and confirmed bad samples. The cluster with the box is the forced degraded samples.

The remaining samples that were used in the final training set are those that are either from clinical cases with shown survival at 1 year or were from cases that were confirmed to be degraded R&D tissues. The resulting clusters are depicted in FIG. 33.

This resulted in five clusters initially, four clusters with clinically good samples and one cluster with confirmed bad samples. One of the good clusters contained only two samples; it did not have high variability within itself and therefore would cause leverage on the model to cause shifts. So, when new samples would be examined, these two samples will more likely cause the other clusters to move around to allow those samples to be grouped appropriately. To test this, a systematic removal of each sample and subsequent re-clustering was examined. It was found that either one of these samples, if isolated, would cause the resulting samples to shift. As such, these samples were removed. It was determined that while this may result in additional samples that are similar to these two tissues to cluster independently, the overall result would be a more robust algorithm and training set to compare against. These samples may be used in conjunction with future samples to reassess the buckets at a later date when the data set can be expanded. The final training library that was validated in the software is depicted in FIG. 34.

Example 7: Group by Group Analysis

Figure 34:
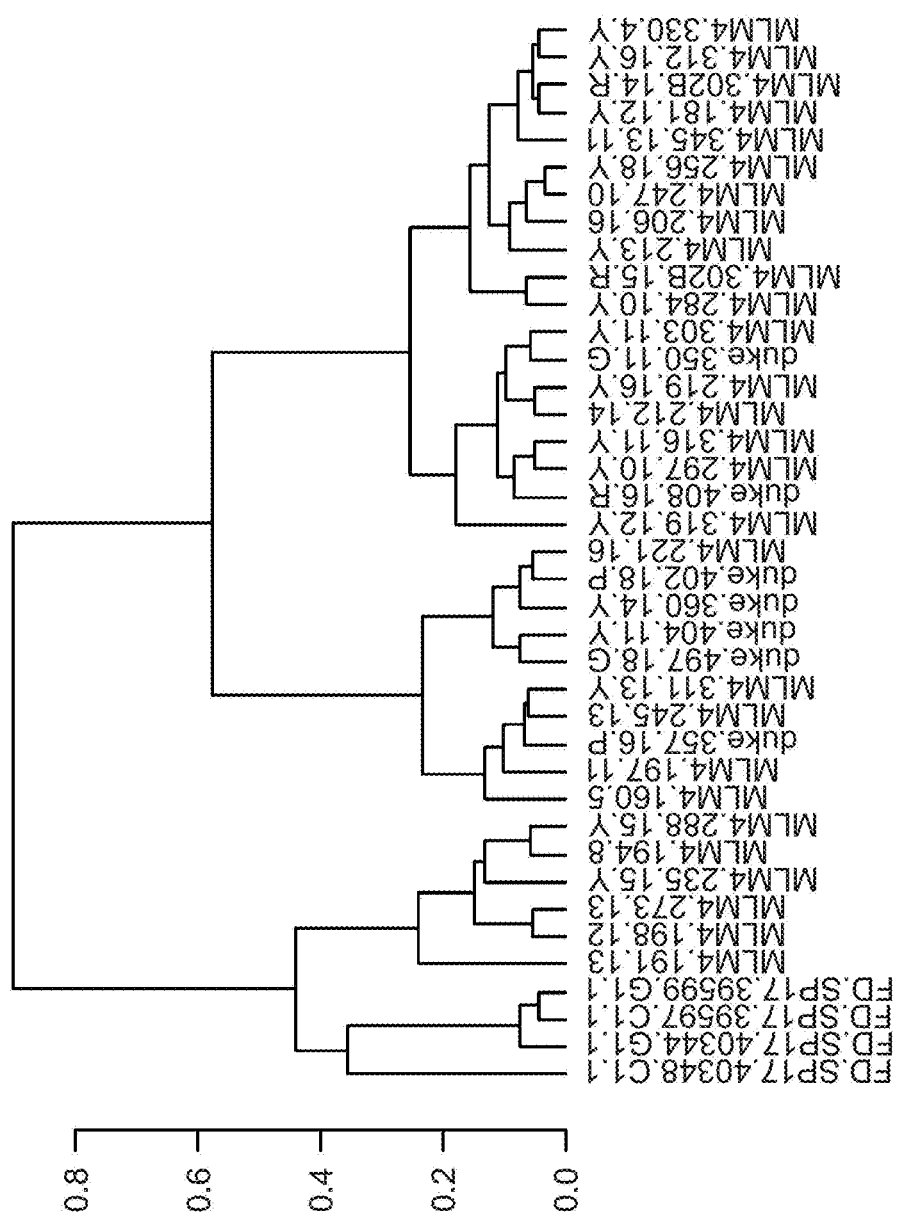
FIG. 34 depicts a final sample library. From left to right the groups are referred to as Group 4, Group 3, Group 2, and Group 1. Groups 1, 2 and 3 are associated with a pass classification and Group 4 is associated with a fail classification.

The underlying data for the four groups depicted in FIG. 34 was examined to try and better understand what underlying features result in the various clusters. Groups will be referred to as groups 1, 2, 3 and 4. The dendrogram above in FIG. 32 has mapped which group name belongs to each cluster, but for additional reference, Groups 1, 2, and 3 are from samples with positive clinical outcomes and Group 4 is comprised of forced degraded samples. Representative images from tissues from each group are shown in FIG. 35A-35D. FIGS. 35A-35D depict representative images for each cluster group in final sample library. Groups 1 (FIG. 35A), 2 (FIG. 35B), and 3 (FIG. 35C) are comprised of samples with positive clinical outcomes. Group 4 (FIG. 35D) is comprised of confirmed degraded samples. Group 1 sample is from LOT-345, Group 2 sample is from LOT-160, Group 3 sample is from LOT-194, and Group 4 sample is from FD.SP17-40348-C1.1 (method of degradation: Freezing at −20° C.

Figure 36A:
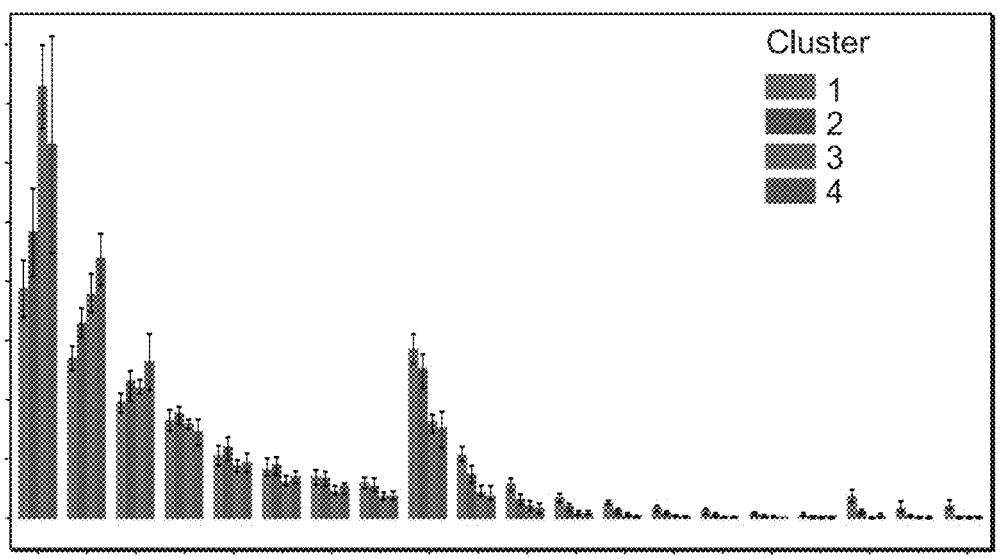
FIGS. 36A-36D is a graphical representation of the different parameters, as broken up by group.
Figure 36B:
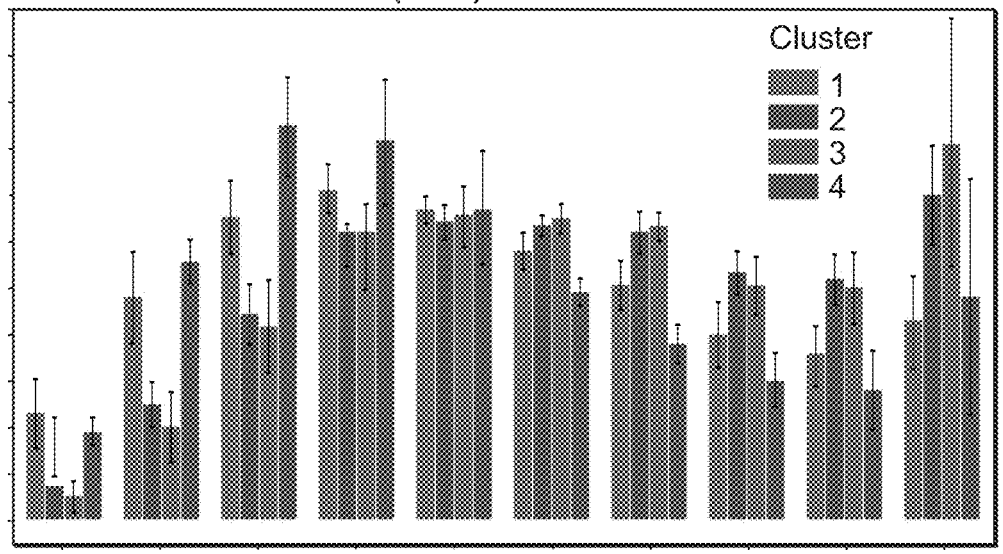
Figure 36C:
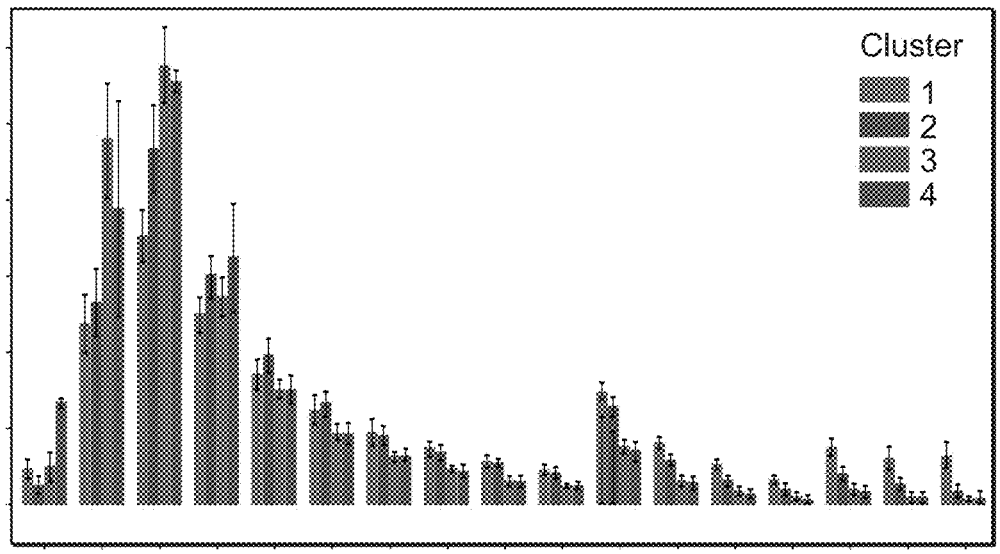
Figure 36D:
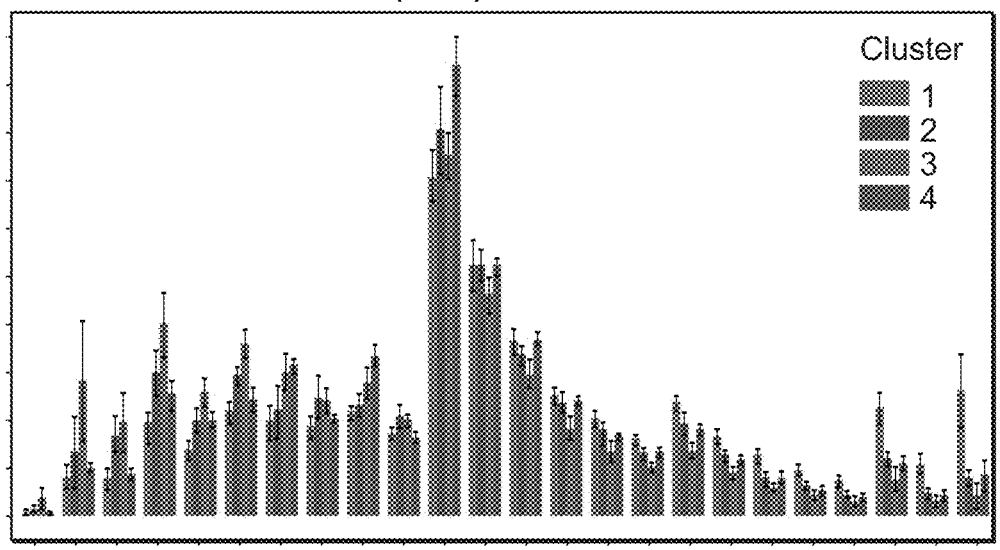

A graphical representation of all the clusters next to each other is shown in FIGS. 36A-36D. FIG. 36A is a graphical representation of clusters of data on area determinations. FIG. 36B is a graphical representation of clusters of data on circularity determinations. FIG. 36C is a graphical representation of clusters of data on integrated density determinations. FIG. 36D is a graphical representation of clusters of data on perimeter determinations.

FIGS. 36A-36D depicts representative images for each cluster group in final sample library. Groups 1, 2, and 3 are comprised of samples with positive clinical outcomes. Group 4 is comprised of confirmed degraded samples. Group 1 sample is from LOT-345, Group 2 sample is from LOT-160, Group 3 sample is from LOT-194, and Group 4 sample is from FD.SP17-40348-C1.1 (method of degradation: Freezing at −20° C.).

As can be seen by the data plotted in FIGS. 36A-36D, different parameters drive the differentiation of the groups with positive clinical outcomes (e.g. mid-sized area, high circularity, and high perimeter). The forced degraded samples are also noticeably different from the other groups in many ways as shown by the red bars on the graphs. This data demonstrates that there are multiple data sets that result in good clinical outcomes. There may be other ways in which samples can appear good or bad that are currently not captured in the data sets and therefore would not be clustered in any group.

Group 1. Group 1 is the largest cluster. It is comprised of 19 different tissues with positive clinical outcomes Group 1 is characterized by a larger proportion of nuclei that have large perimeters, high integrated densities, and high area with lower circularity. This is likely due to the presence of clumps of nuclei that cannot be read as independent cells by the software. This would more likely occur in tissues that still have larger number of thymocytes present in the earlier days of the culture period. When a blinded study was run, a sample from a Day 0 tissue clustered into Group 1, thereby lending support to the above theory. While it does not appear that this assay will reject tissues that have large numbers of thymocytes present, the samples in Group 1 had positive clinical outcomes when implanted at the end of the culture period.

Figure 37:
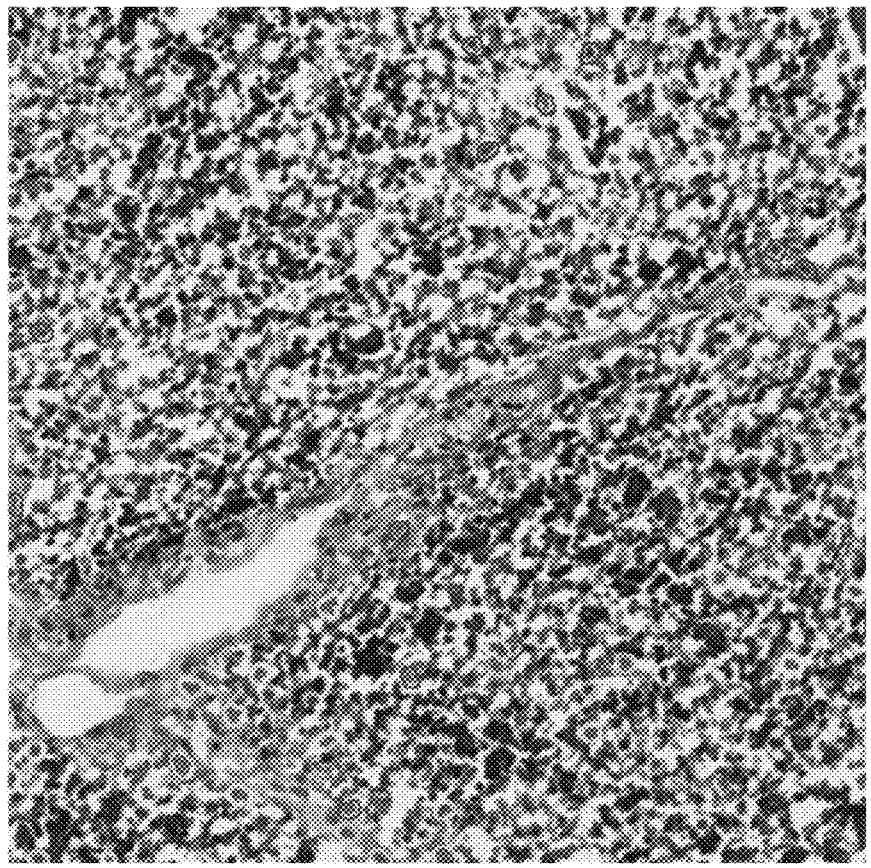
FIG. 37 is an image from Group 1 with features within Area-10 (red), Circularity-0.9 (green), Perimeter-18 (blue), and Integrated Density-1500 (yellow) highlighted. These groups generally show the largest variation between the groups.

FIG. 37 is an image from Group 1 with features within Area-10 (red), Circularity-0.9 (green), Perimeter-18 (blue), and Integrated Density-1500 (yellow) highlighted. These groups generally show the largest variation between the groups.

Figure 38:
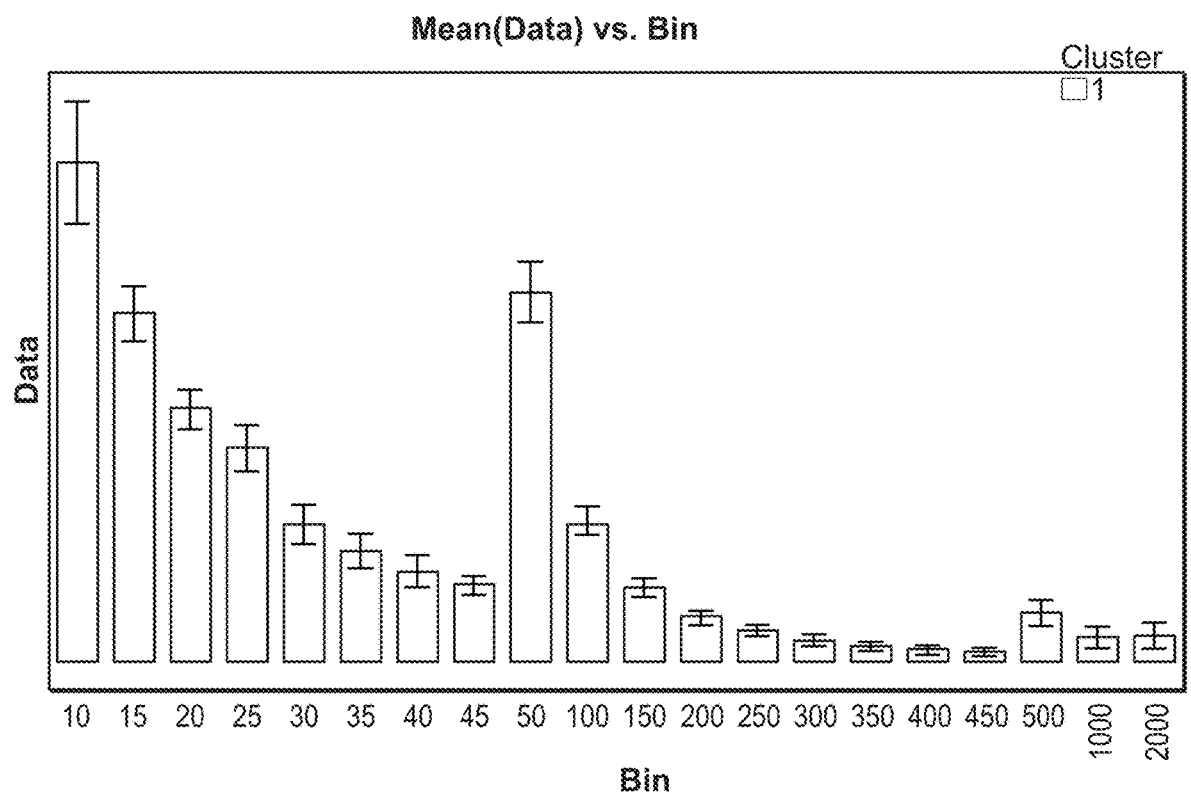
FIG. 38 is a histogram depicting area measurements of cells in Group 1.

FIG. 38 is a histogram depicting area measurements of cells in Group 1.

Figure 39:
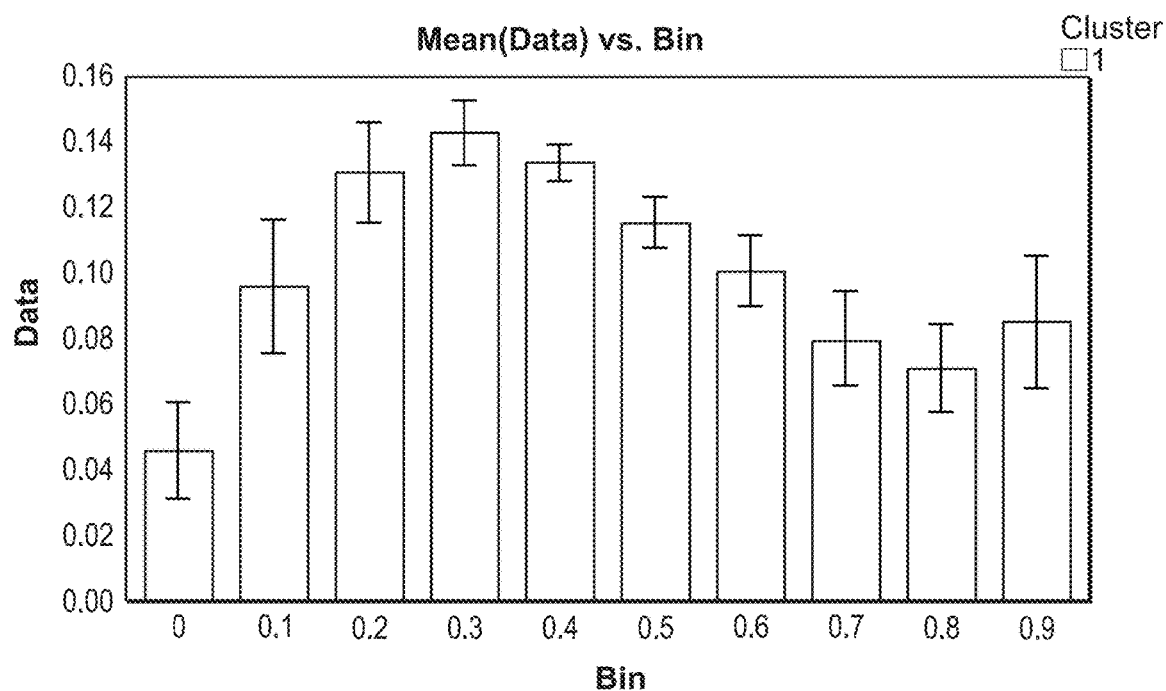
FIG. 39 is a histogram depicting circularity measurements of cells in Group 1.

FIG. 39 is a histogram depicting circularity measurements of cells in Group 1.

Figure 40:
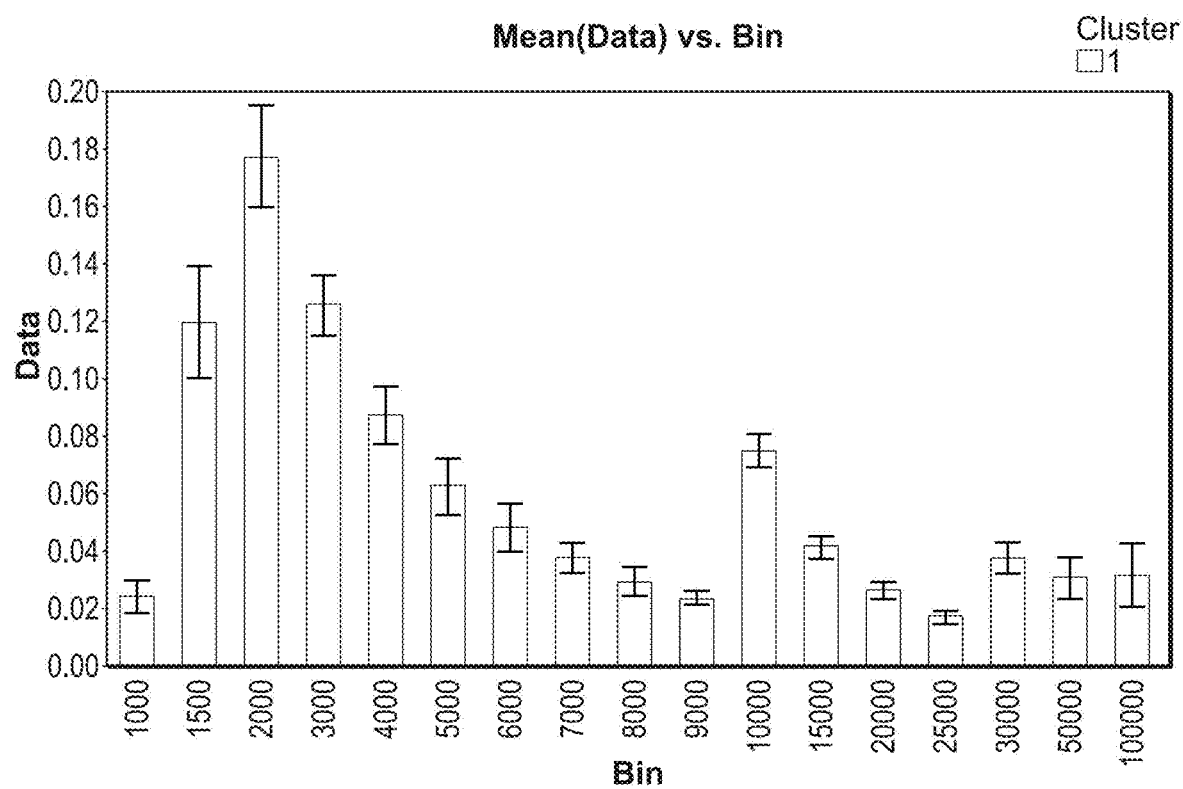
FIG. 40 is a histogram depicting integrated density measurements of cells in Group 1.

FIG. 40 is a histogram depicting integrated density measurements of cells in Group 1.

Figure 41:
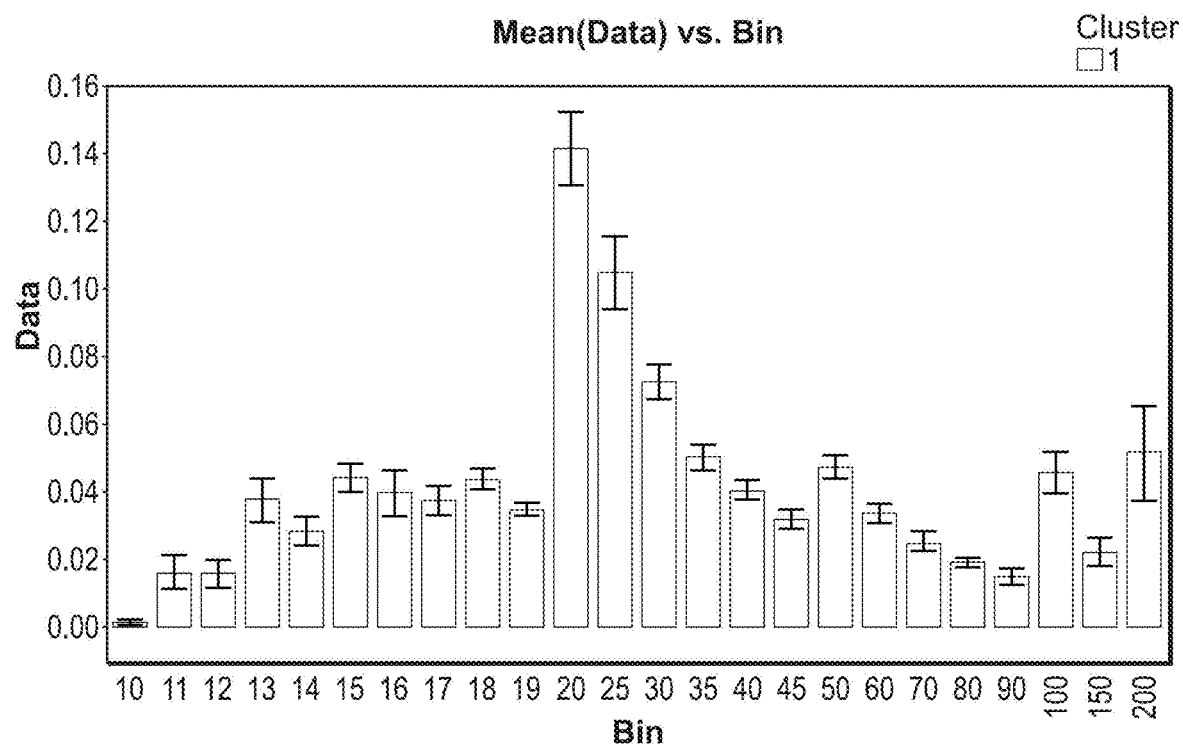
FIG. 41 is a histogram depicting perimeter measurements of cells in Group 1.

FIG. 41 is a histogram depicting perimeter measurements of cells in Group 1.

Group 2.

Group 2 contains 10 lots of tissues that had positive clinical outcomes. Groups 2 and 3 both have large proportions of cells with high circularity values. Group 2 also appears to have cells with higher area when compared to groups 3 and 4, and mid-range integrated density. These values are expected for healthy viable tissues in the mid-range of the culture period as shown by the samples that form Group 2. Histograms of the measurements of area, circularity, integrated density and perimeter appear in FIGS. 43-46.

Figure 42:
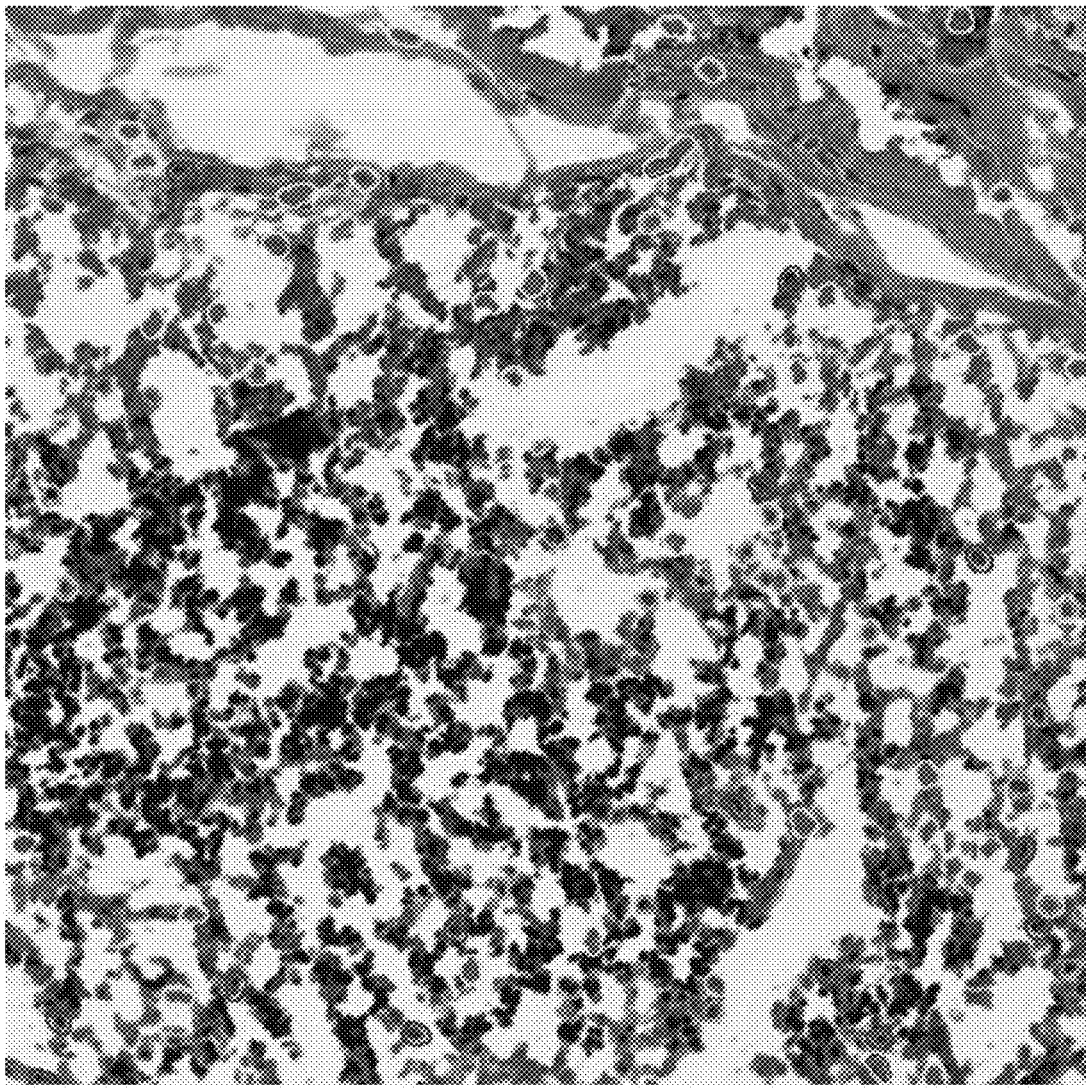
FIG. 42 is an image of Group 2 with features within Area-10 (red), Circularity-0.9 (green), Perimeter-18 (blue), and IntegratedDensity-1500 (yellow) highlighted. These groups generally show the largest variation between the groups.

FIG. 42 is an image of Group 2 with features within Area-10 (red), Circularity-0.9 (green), Perimeter-18 (blue), and IntegratedDensity-1500 (yellow) highlighted. These groups generally show the largest variation between the groups.

Figure 43:
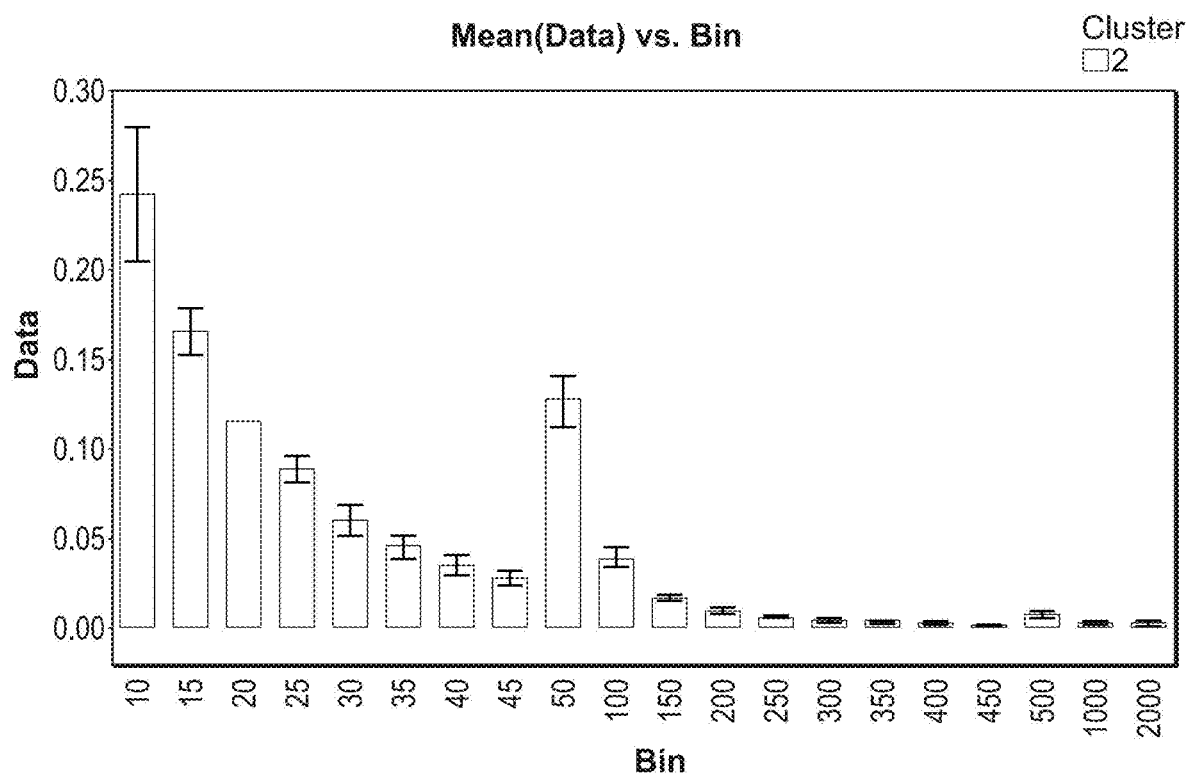
FIG. 43 is a histogram depicting area measurements of cells in Group 2.

FIG. 43 is a histogram depicting area measurements of cells in Group 2.

Figure 44:
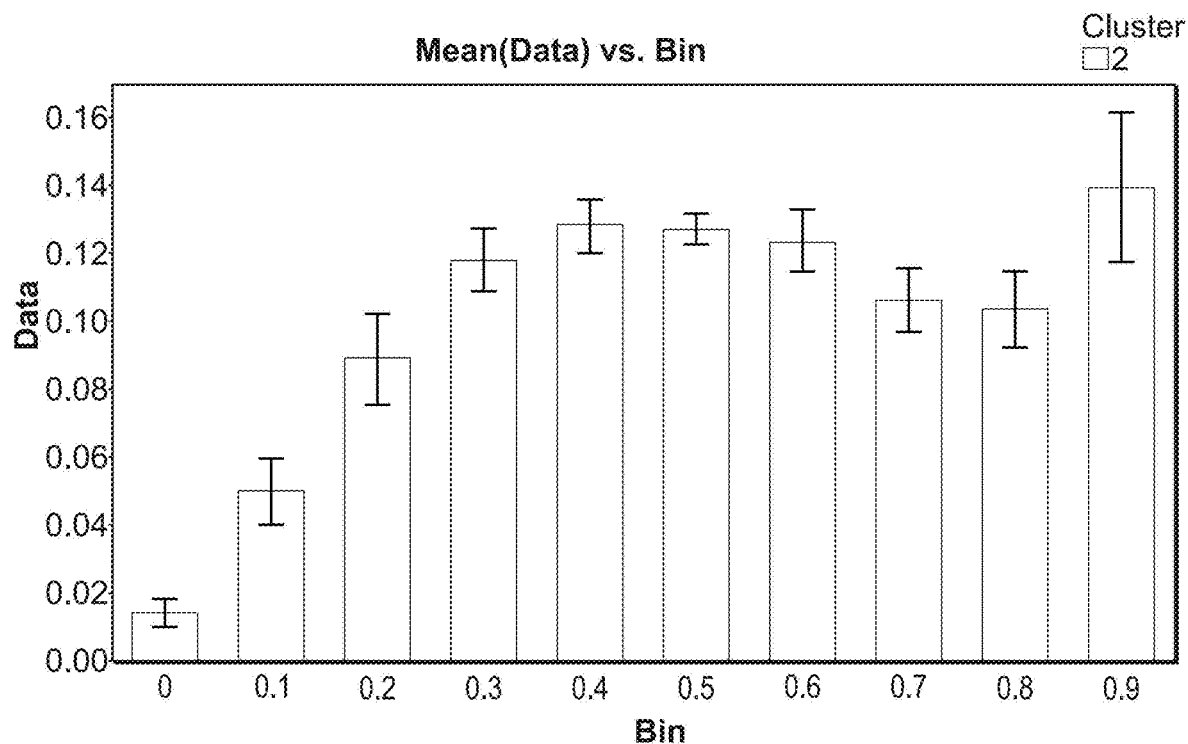
FIG. 44 is a histogram depicting circularity measurements of cells in Group 2.

FIG. 44 is a histogram depicting circularity measurements of cells in Group 2.

Figure 45:
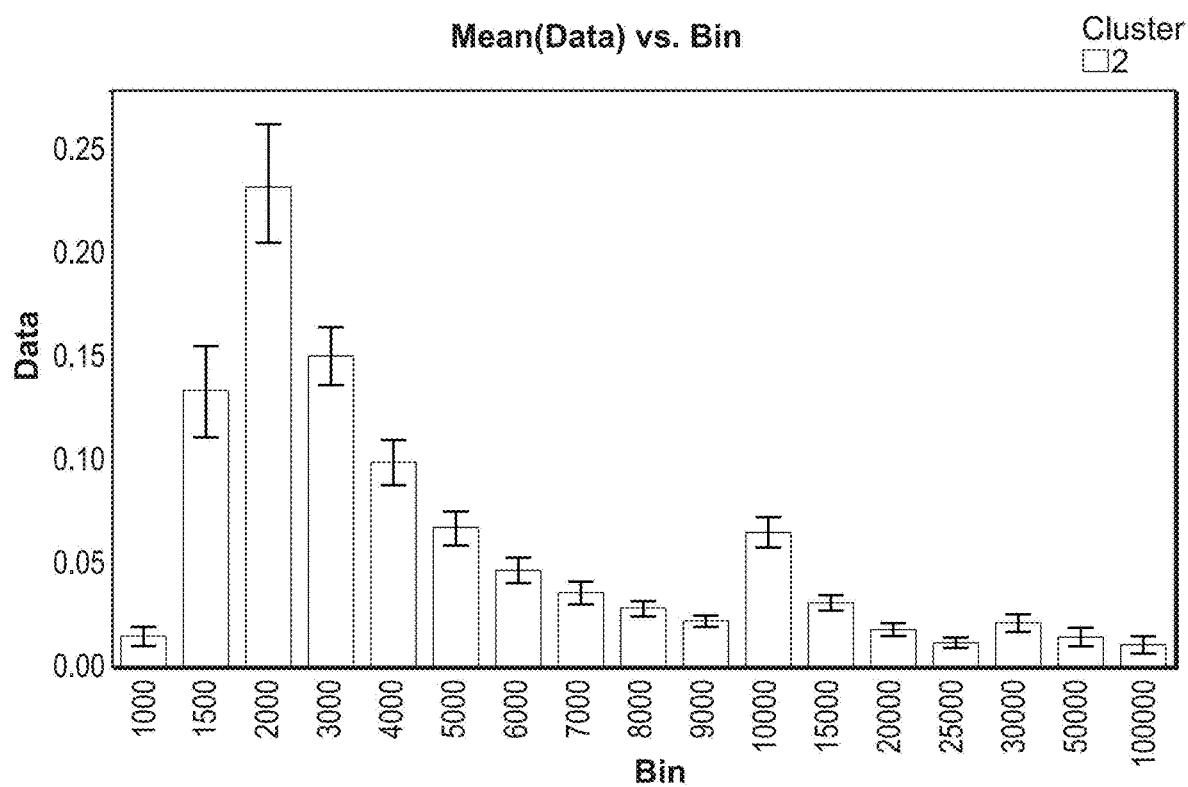
FIG. 45 is a histogram depicting integrated density measurements of cells in Group 2.

FIG. 45 is a histogram depicting integrated density measurements of cells in Group 2.

Figure 46:
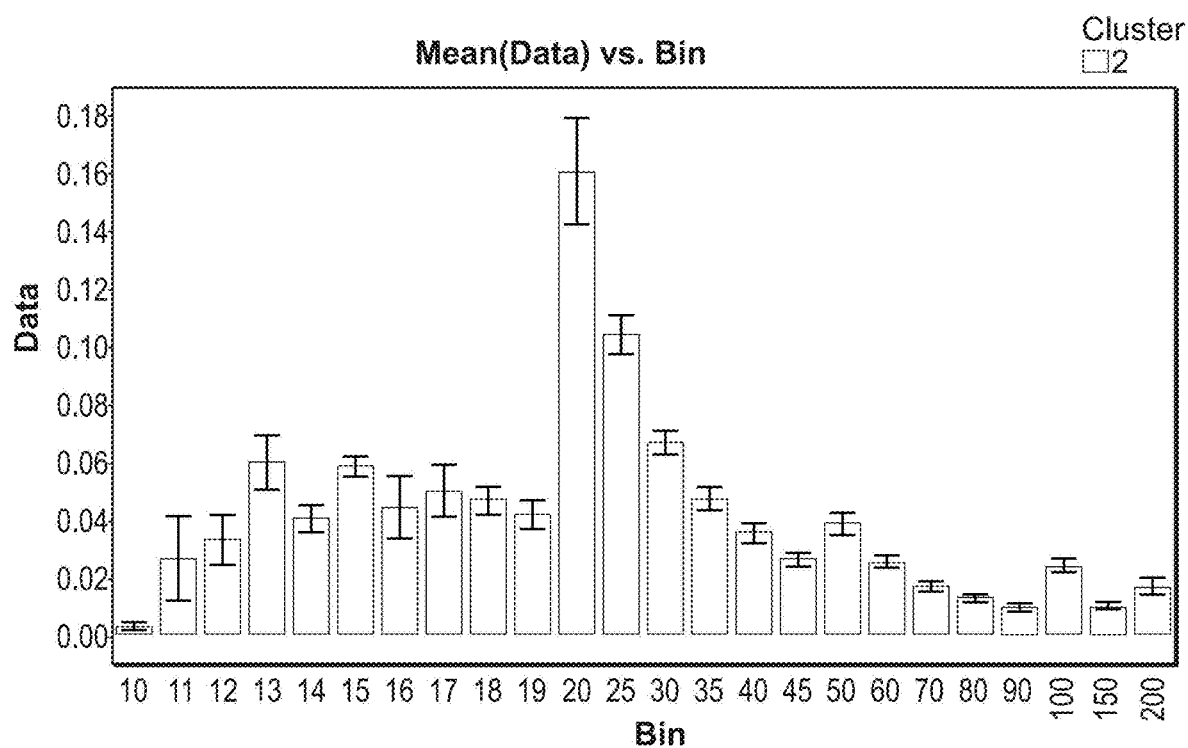
FIG. 46 is a histogram depicting perimeter measurements of cells in Group 2.

FIG. 46 is a histogram depicting perimeter measurements of cells in Group 2.

Group 3.

Group 3 is comprised of 6 lots that showed positive clinical outcomes. Like group 2, group 3 has a large proportion of cells with high circularity, showing both thymocytes and overall cellular viability. Group 3 has the highest proportion of cells of the smallest area and also in the lower range of integrated density (2nd and 3rd bins).

Figure 47:
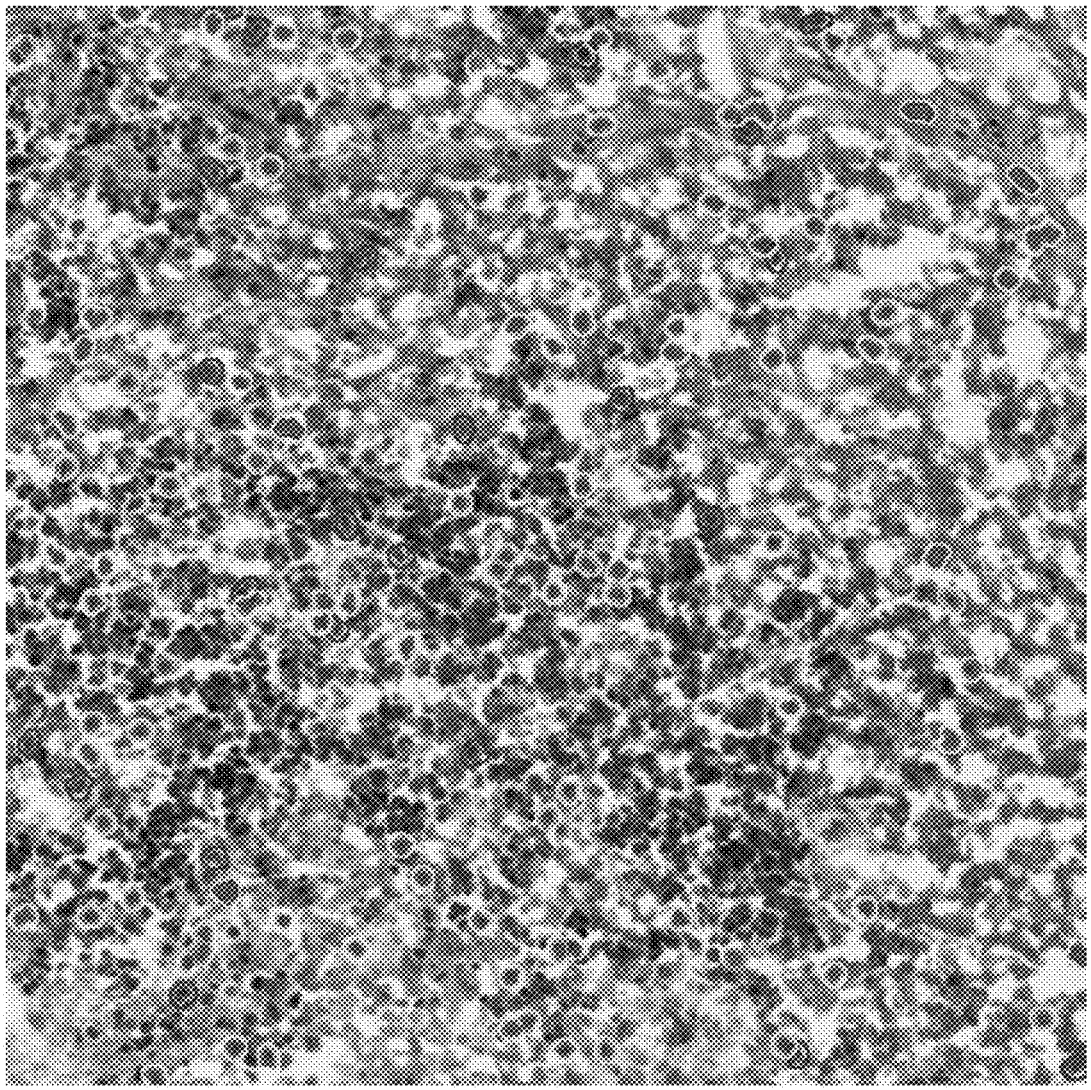
FIG. 47 is an image from Group 3 with features within Area-10 (red), Circularity-0.9 (green), Perimeter-18 (blue), and Integrated Density-1500 (yellow) highlighted. These groups generally show the largest variation between the groups.

FIG. 47. Is an image from Group 3 with features within Area-10 (red), Circularity-0.9 (green), Perimeter-18 (blue), and Integrated Density-1500 (yellow) highlighted. These groups generally show the largest variation between the groups.

Histograms of the measurements of area, circularity, integrated density and perimeter appear in FIGS. 48-51.

Figure 48:
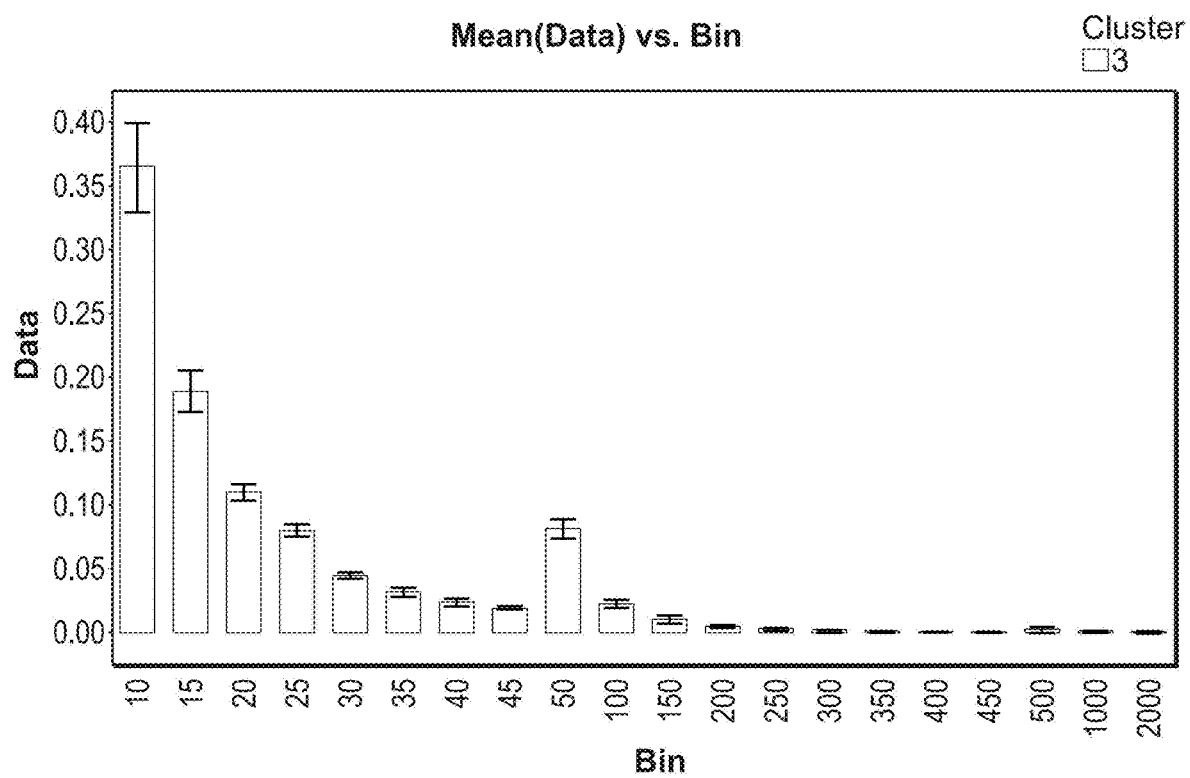
FIG. 48 is a histogram depicting area measurements of cells in Group 3.

FIG. 48 is a histogram depicting area measurements of cells in Group 3.

Figure 49:
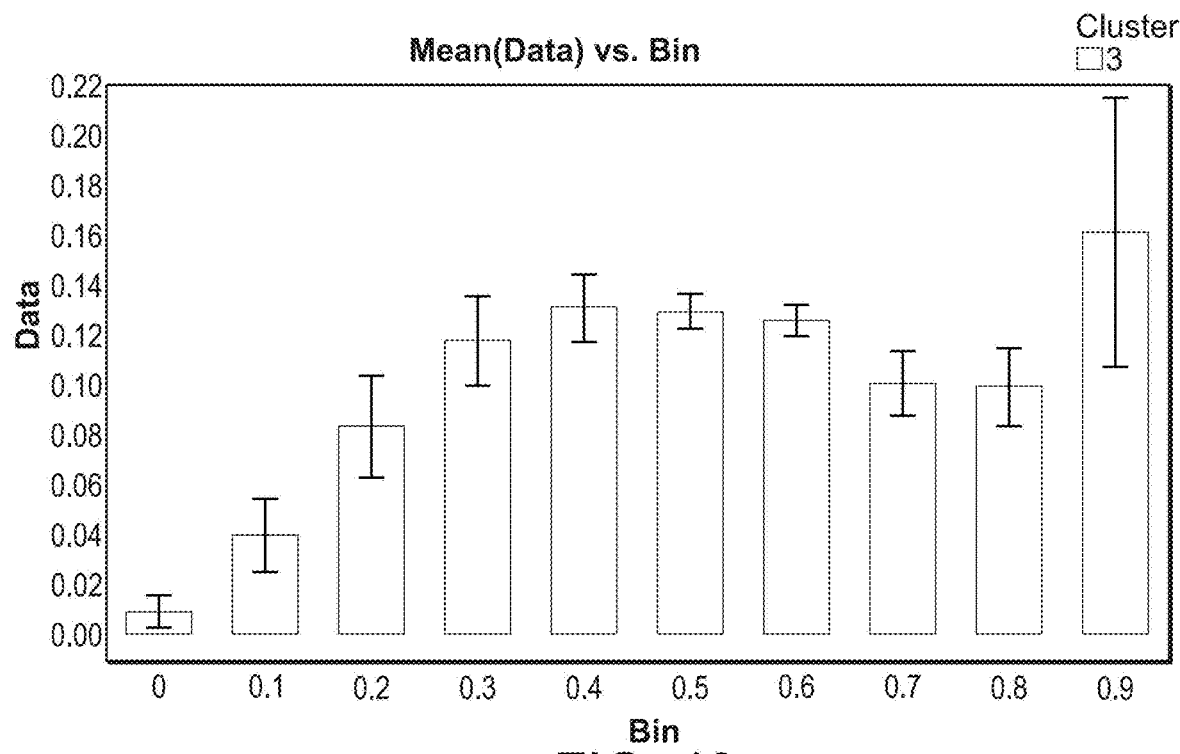
FIG. 49 is a histogram depicting circularity measurements of cells in Group 3.

FIG. 49 is a histogram depicting circularity measurements of cells in Group 3.

Figure 50:
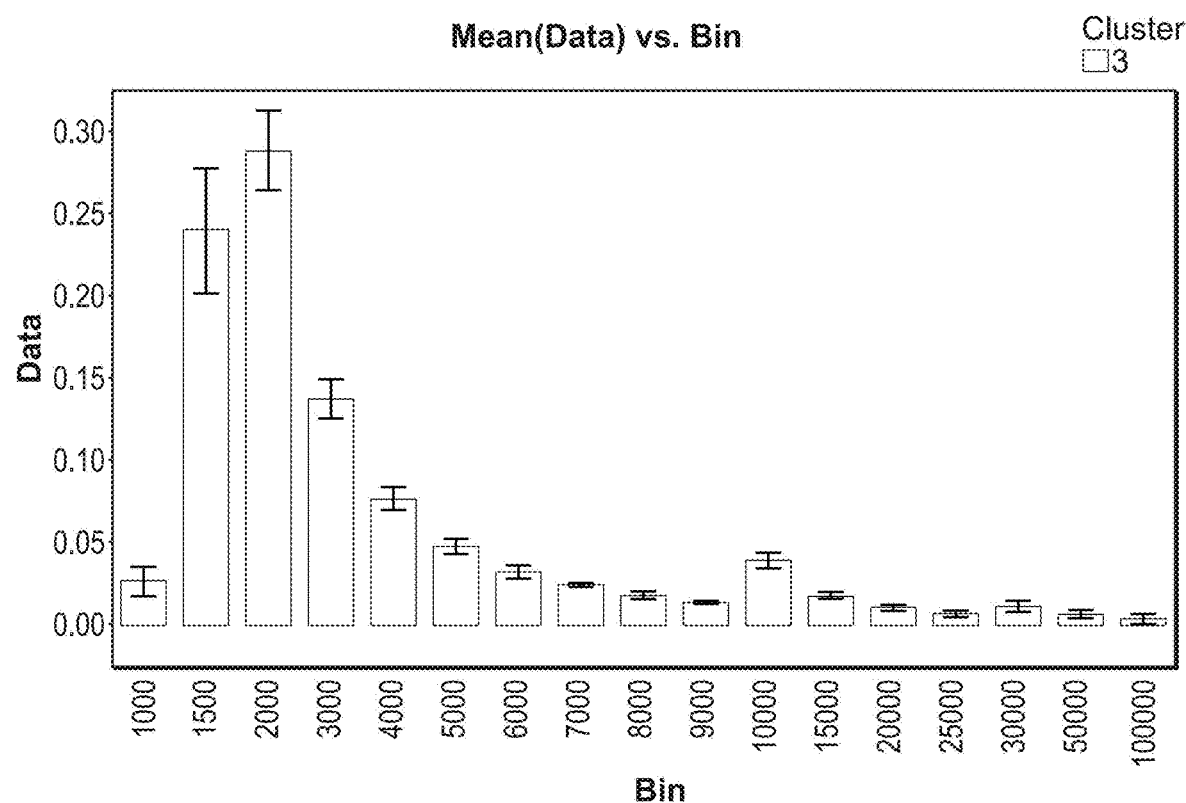
FIG. 50 is a histogram depicting integrated density measurements of cells in Group 3.

FIG. 50 is a histogram depicting integrated density measurements of cells in Group 3.

Figure 51:
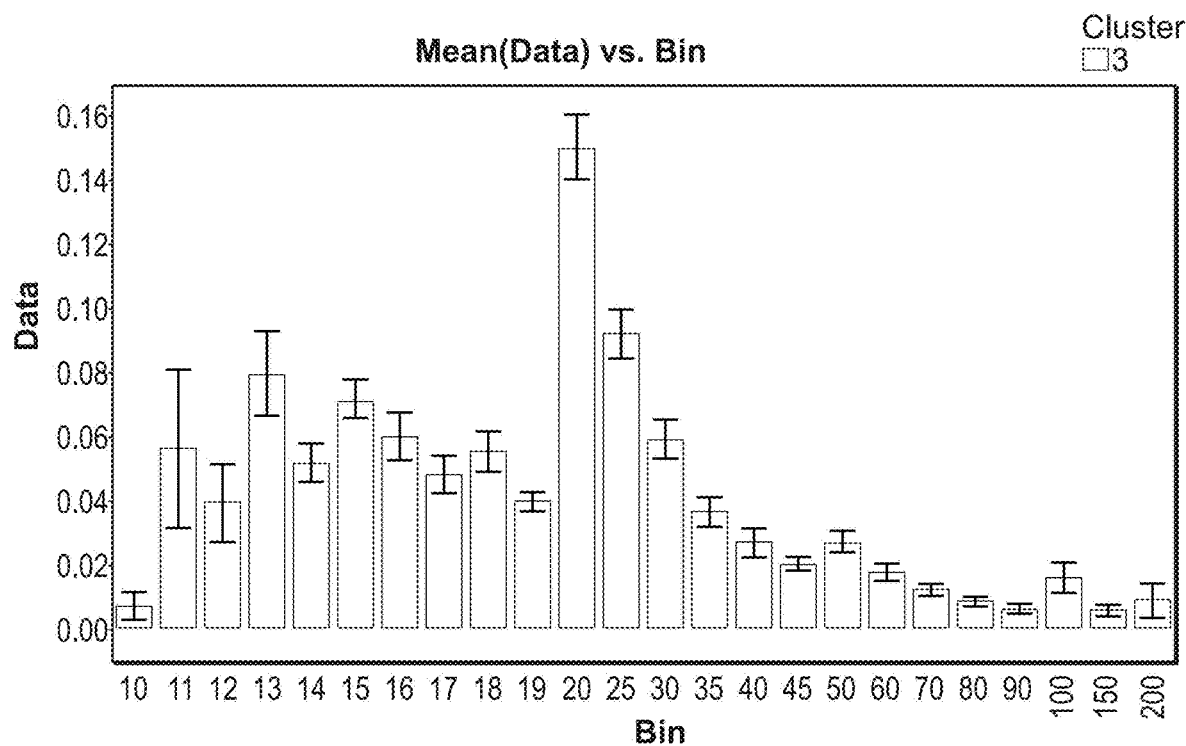
FIG. 51 is a histogram depicting perimeter measurements of cells in Group 3.

FIG. 51 is a histogram depicting perimeter measurements of cells in Group 3.

Group 4.

Group 4 is comprised of 4 forced degraded samples. The degradation conditions shown here are for samples that have been frozen at −20° C. for 4 hours and samples where the culture media was replaced with 10×PBS for 24 hrs. Both of these conditions showed significant degradation per qualitative histology and significant changes when examining CCL21, which is a biomarker for TEC health. A table of all forced degraded conditions and the results for each method is included below.

Figure 52:
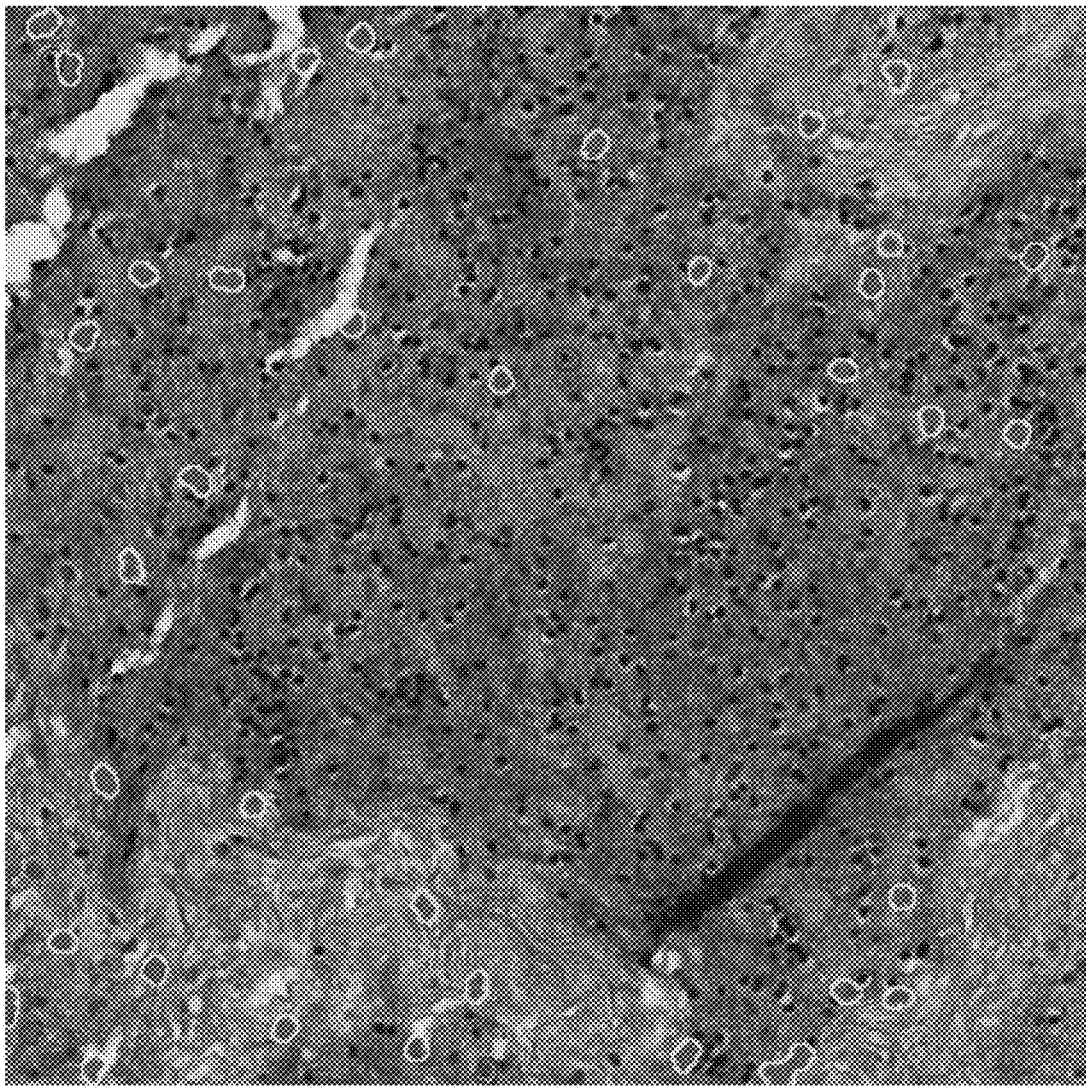
FIG. 52 is an image from Group 4 with features within Area-10 (red), Circularity-0.9 (green), Perimeter-18 (blue), and Integrated Density-1500 (yellow) highlighted. These groups generally show the largest variation between the groups.

FIG. 52 is an image from Group 4 with features within Area-10 (red), Circularity-0.9 (green), Perimeter-18 (blue), and Integrated Density-1500 (yellow) highlighted. These groups generally show the largest variation between the groups.

Histograms of the measurements of area, circularity, integrated density and perimeter appear in FIGS. 53-56.

Figure 53:
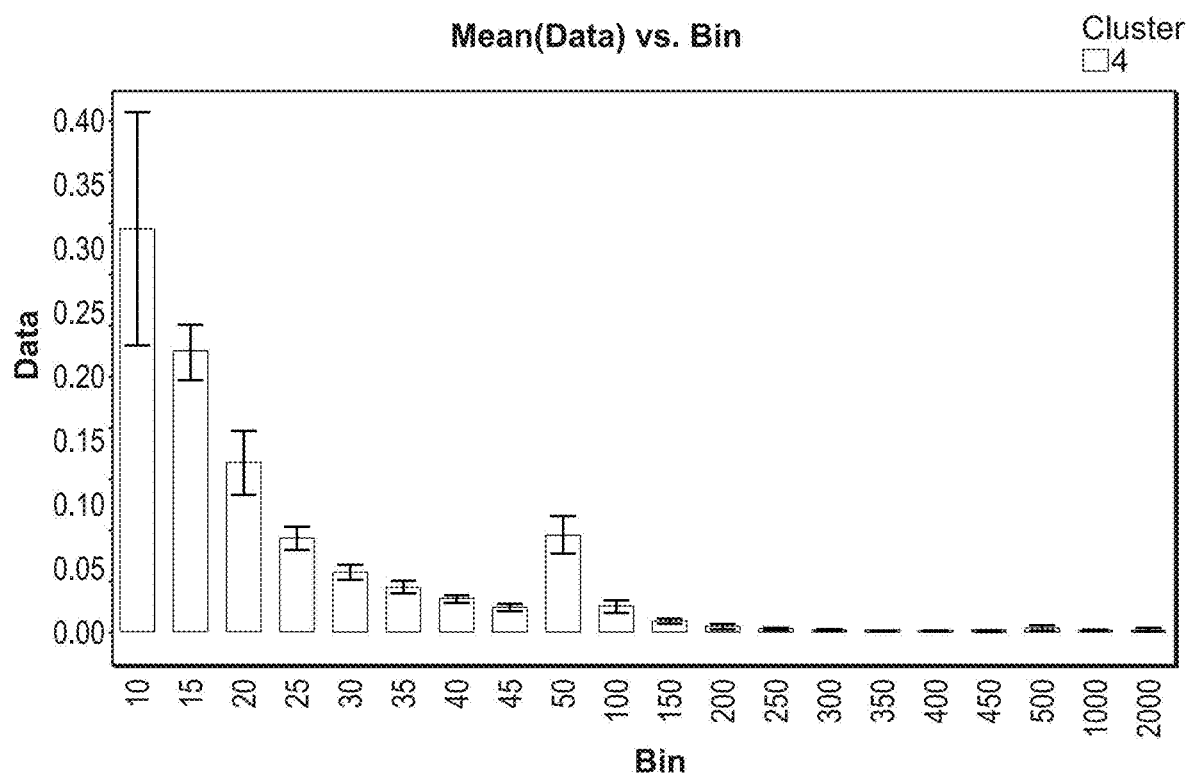
FIG. 53 is a histogram depicting area measurements of cells in Group 4.

FIG. 53 is a histogram depicting area measurements of cells in Group 4.

Figure 54:
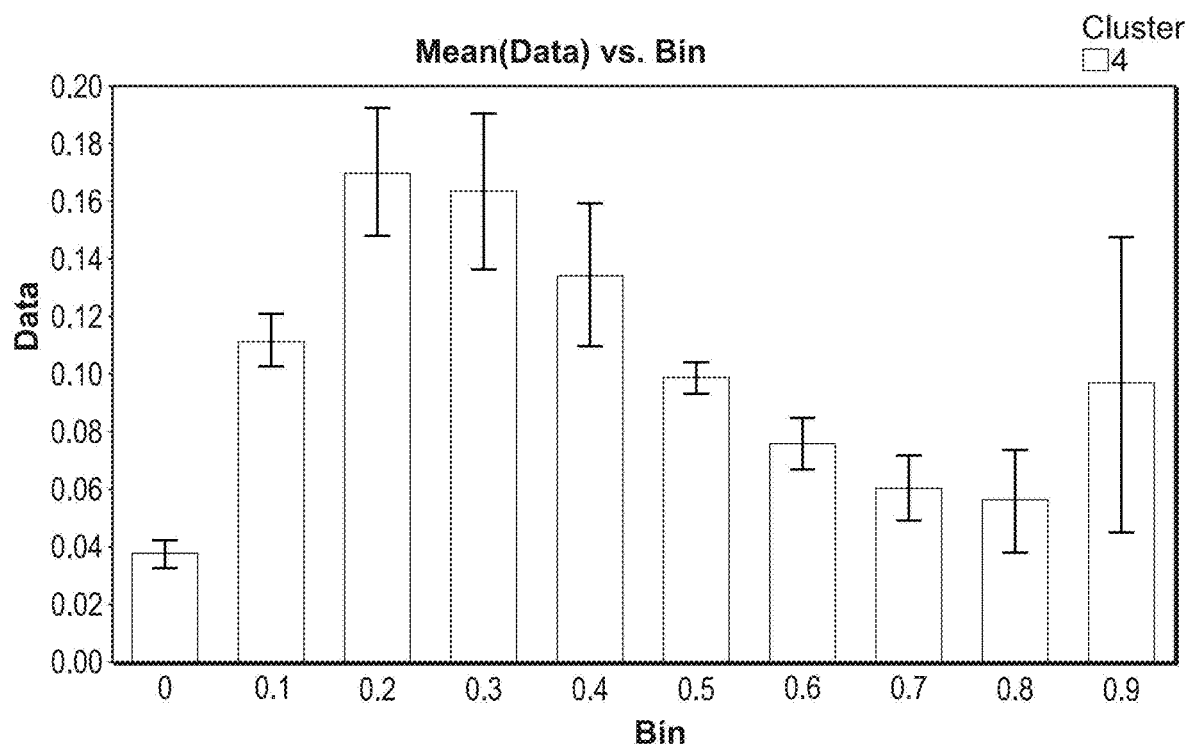
FIG. 54 is a histogram depicting circularity measurements of cells in Group 4.

FIG. 54 is a histogram depicting circularity measurements of cells in Group 4.

Figure 55:
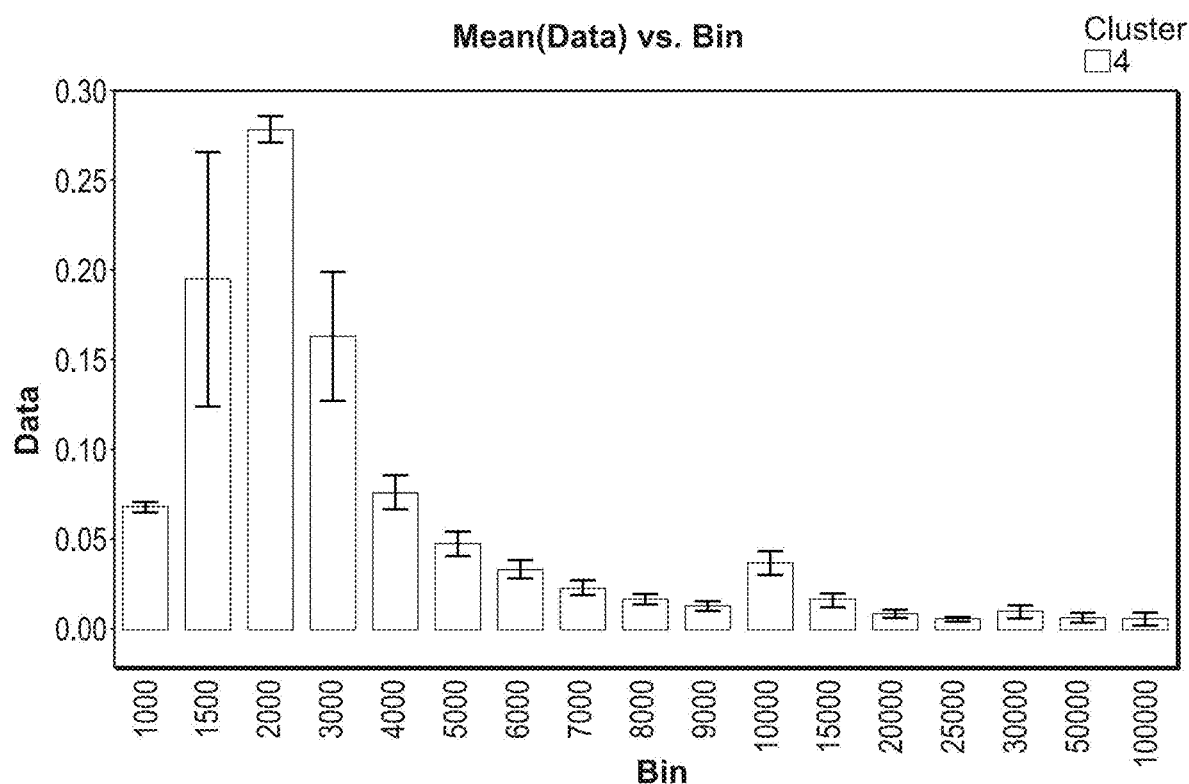
FIG. 55 is a histogram depicting integrated density measurements of cells in Group 4.

FIG. 55 is a histogram depicting integrated density measurements of cells in Group 4.

Figure 56:
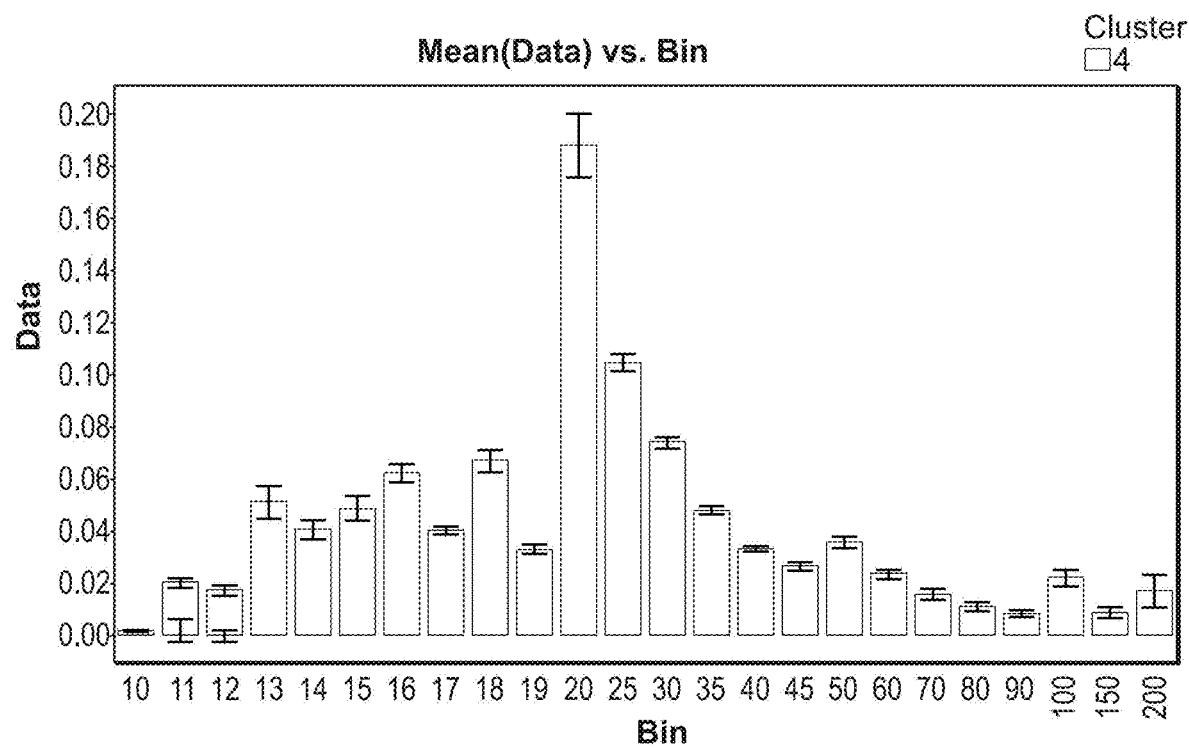
FIG. 56 is a histogram depicting perimeter measurements of cells in Group 4.

FIG. 56 is a histogram depicting perimeter measurements of cells in Group 4.

Example 8: Forced Degradation Study

A forced degradation study was run where the samples were placed back in thymus organ medium (TOM) prior to the samples being removed on days 5 and 9. This shows how hardy allogeneic cultured postnatal thymus tissue-derived product is to variations in process conditions. It is interesting to note that heating the samples to 55° C. was not detectable by the present method of traditional histology. This is likely because heating the tissue essentially fixed it from a histopathological perspective. However, the degradation was apparent via CCL21 analysis. Many of the tested conditions did not cause degradation detectable via any of the measures used. It is believed that these conditions did not permanently damage the tissue to a point where it was either not functional or not viable. There are process controls to ensure the product is never exposed to any of the above conditions. As would be expected of degraded samples, there are large proportions of cells with lower circularity, and low area and higher perimeters. This shows cells that are no longer able to maintain viability and are therefore changing morphology and shrinking with shriveled edges. The forced degradation conditions of the study appear in Table 7.

To show the similarity within a group, analysis of the variability for each bin was examined. Group 4 regularly exhibited the highest standard deviation within a bin across the samples in it. This is possibly due to the fewer samples within that group, but it is also not unexpected for tissue as it degrades to be less consistent (see FIG. 57).

Figure 57:
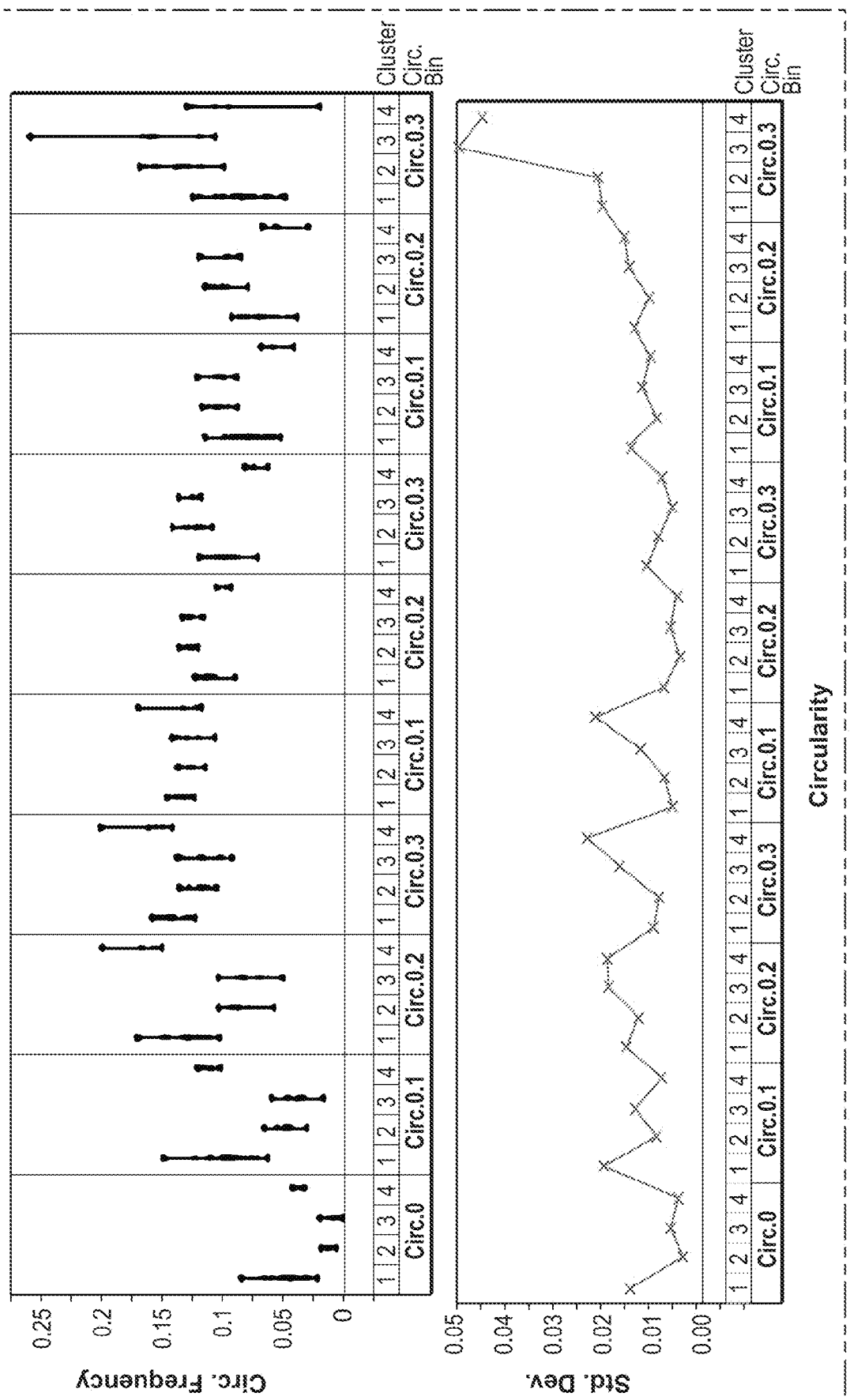
FIG. 57 are plots of an analysis of variability between and within the groups on a bin-by-bin basis. Data is shown on the x axis first by group then by bin for the parameter. The top graph for each parameter are the individuals and the bottom is the standard deviation of that group. Both can be used to visualize the spread of the data.
Figure 57:
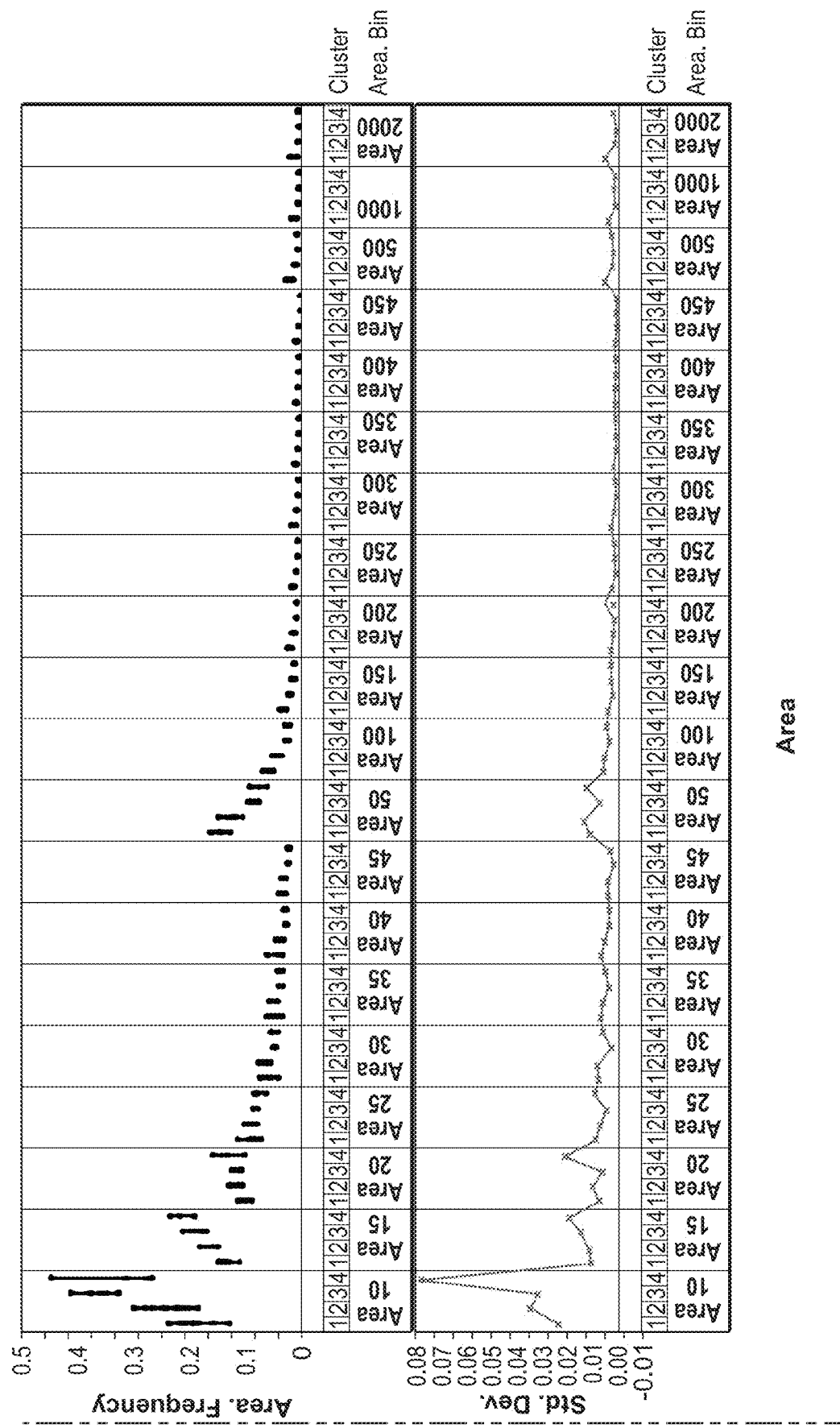
Figure 57:
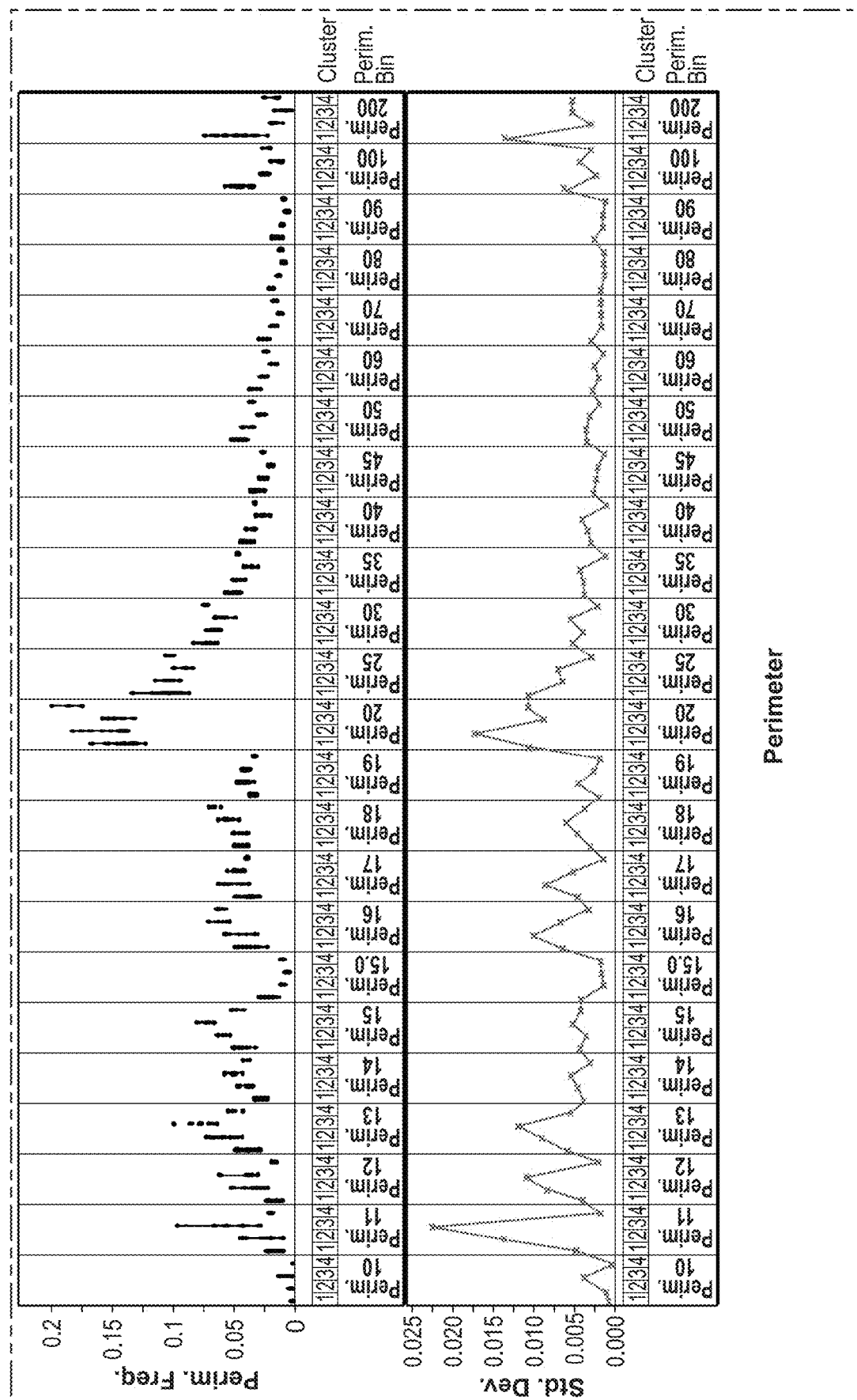
Figure 57:
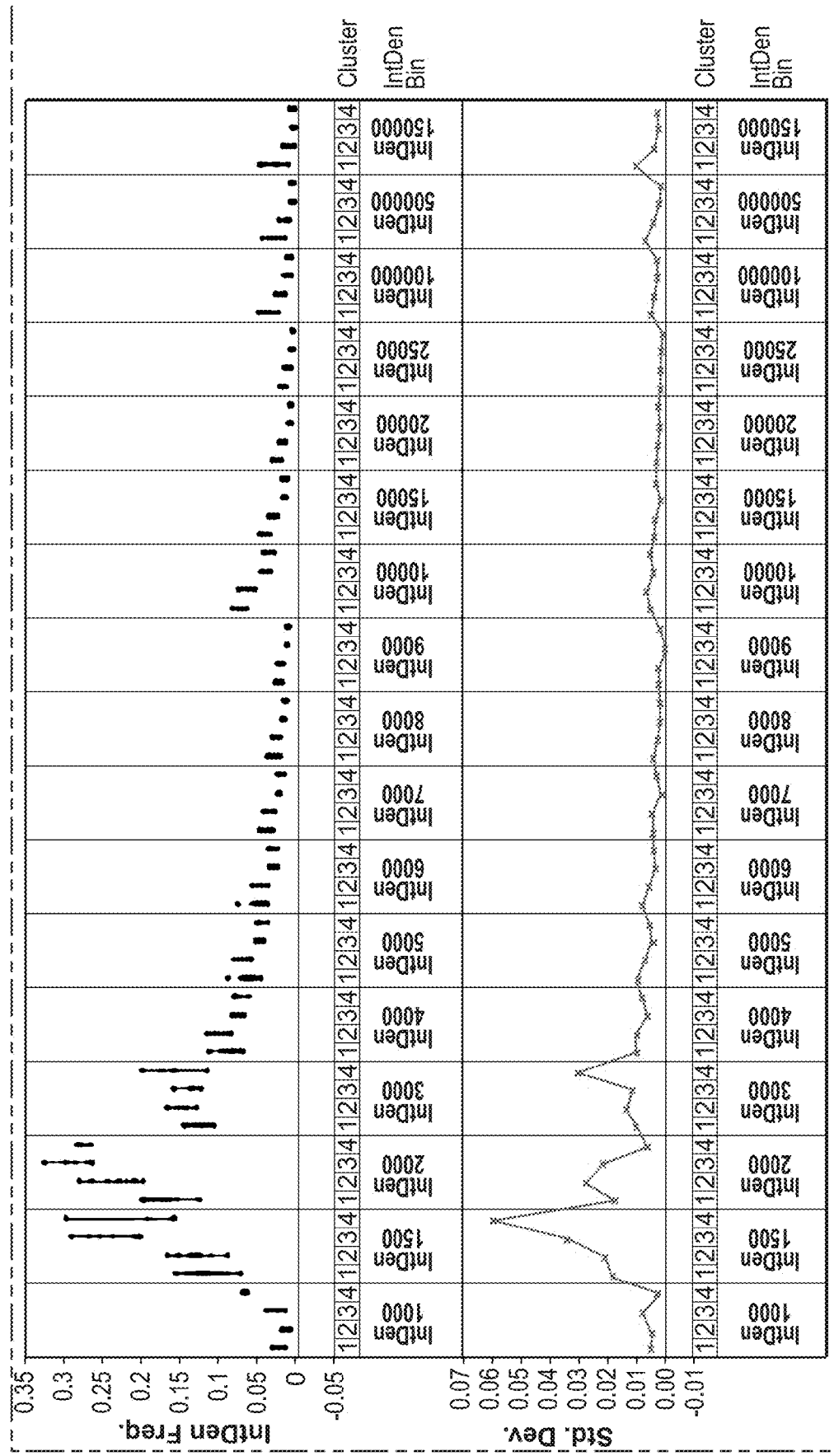

FIG. 57 are plots of an analysis of variability between and within the groups on a bin by bin basis. Data is shown on the x axis first by group then by bin for the parameter. The top graph for each parameter are the individuals and the bottom is the standard deviation of that group. Both can be used to visualize the spread of the data.

Abbreviations:

AE1/AE3: A cocktail of 2 antibodies that react with all cytokeratins to identify epithelial cells.

CD3: An antibody that reacts with T cells, including thymocytes. CK14: An antibody that detects only cytokeratin 14, a component of the cytoskeleton in a subset of epithelial cells hypothesized to have repopulating potential.

FFPE: Formalin-fixed paraffin embedded tissue sections.

H&E: Hematoxylin and eosin, a histologic stain that is most commonly used for light microscopy of mammalian tissue sections.

Ki-67: The Ki-67 antibody recognizes the Ki-67 antigen, a protein associated with cellular proliferation.

TEC: Thymic epithelial cells.

References discussed in the application, which are incorporated by reference in their entirety, for their intended purpose, which is clear based upon its context.

All patents, patent applications and publications cited herein are hereby incorporated by reference in their entirety. The disclosures of these publications in their entireties are hereby incorporated by reference into this application.

The disclosures of each and every patent, patent application, publication, and accession number cited herein are hereby incorporated herein by reference in their entirety.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The foregoing embodiments and advantages are merely exemplary and are not to be construed as limiting the present invention. The present teachings can be readily applied to other types of methods, systems and classifiers, experiments and surgical procedures. Also, the description of the embodiments of the present invention is intended to be illustrative and not to limit the scope of the claims. Many alternatives, modifications, and variations will be apparent to those skilled in the art While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

REFERENCES

Markert M L, Devlin B H, McCarthy E A, 2010, "Thymus transplantation," *Clin Immunol.*, 135(2): 236-46.
Markert M L. et al., 2004, "Postnatal thymus transplantation with immunosuppression as treatment for DiGeorge syndrome," *Blood* 104(8):2574-2581.
Markert M L, et al., 1999, "Transplantation of thymus tissue in complete DiGeorge syndrome," *N Engl J Med* 341(16): 1180-1189 27). Markert M L, et al., 2008, "Use of allograft biopsies to assess thymopoiesis after thymus transplantation," *J Immunol* 180(9):6354-6364.
Markert M L, et al., 2007, "Review of 54 patients with complete DiGeorge anomaly enrolled in protocols for thymus transplantation: outcome of 44 consecutive transplants," *Blood* 109(10):4539-454728).
Chinn I K, Devlin B H, Li Y J, & Markert M L, 2008, "Long-term tolerance to allogeneic thymus transplants in complete DiGeorge anomaly," *Clin Immunol* 126(3):277-281).
Markert M L, 2014, Thymus Transplantation. Stiehm's Immune Deficiencies, eds Sullivan K E & Stiehm E R (Academic Press), 1st Ed, pp 1059-1067.

What is claimed is:

1. A method of training a tissue classifier for performing quantitative histopathological assessment, comprising:
   converting a slide image into a binary slide image, wherein the slide image is selected from a library of control images, wherein each slide image in the library of control images is associated with a pass classification or a fail classification;
   detecting one or more nuclei within the binary slide image;
   for each detected nucleus, extracting a feature from the detected nucleus, wherein the feature represents a property of the detected nucleus within the binary slide image and comprises at least one of an area of the detected nucleus, a perimeter of the detected nucleus, an integrated density of the detected nucleus, or a circularity of the detected nucleus;
   for each detected nucleus, generating, based on the feature, a feature fingerprint associated with the binary slide image, wherein the feature fingerprint is a numerical value calculated from processing the feature;
   incorporating the binary slide image into a cluster wherein the cluster comprises a plurality of images, wherein each of the first plurality of images is associated with a corresponding feature fingerprint, and wherein the incorporating is based on comparing the feature fingerprint with the corresponding feature fingerprint;
   applying a cutoff height to the cluster to form a plurality of groups, wherein the cutoff height minimizes a number of groups within the plurality of groups based on multivariate analysis of variance analysis of the cluster;
   categorizing a first group within the plurality of groups as a positive control set if the first group comprises first slide images associated with the pass classification; and
   categorizing a second group within the plurality of groups as a negative control set if the second group comprises second slide images associated with the fail classification.

2. The method according to claim 1, wherein the tissue classifier is capable of determining potency or the quality of the tissue for transplantation into a subject.

3. The method according to claim 2, wherein the tissue is thymus tissue.

4. The method according to claim 3, wherein the tissue is allogeneic cultured postnatal thymus tissue-derived product slices for implantation into a human subject.

5. The method according to claim 4, wherein the human subject is suffering from complete DiGeorge syndrome associated with 22q11.2 deletion; coloboma, heart defect, choanal atresia, growth or mental retardation, genital hypoplasia and ear anomalies or deafness syndrome (CHARGE), or athymia associated with forkhead box protein N1 (FOXN1) deficiency.

6. The method according to claim 2, wherein the tissue classifier determines potency or quality of a tissue for transplantation into a subject of an unknown tissue for transplantation by generating feature fingerprints of detected nuclei within slide images in a control library and clustering the slide images based on their corresponding feature fingerprints.

7. The method according to claim 6, wherein the unknown tissue is thymus tissue.

8. The method according to claim 7, where the thymus tissue has been subjected to a culturing process in a thymus organ medium for a period of time to partially deplete the thymus tissue of thymocytes.

9. The method according to claim 8, wherein the period of time is up to 21 days.

10. The method according to claim 8, wherein the period of time is from about 12 to about 21 days.

11. The method according to claim 8, wherein the period of time is from about 5 to about 9 days.

12. The method according to claim 8, wherein the culturing process preserves the functional architecture of the thymic stroma.

13. The method according to claim 12, wherein the thymic stroma comprises thymic epithelial cells and fibroblasts.

14. The method according to claim 1, wherein the tissue is selected from the group consisting of vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

15. The method according to claim 1, wherein the feature fingerprint is generated from measurements comprising numerical values of an area of the detected nucleus, a perimeter of the detected nucleus, an integrated density of the detected nucleus, and a circularity of the detected nucleus.

16. A method for performing quantitative histopathological assessment of an unclassified slide image of a tissue, comprising:
    detecting a hematoxylin channel from the unclassified slide image, wherein the hematoxylin channel is associated with a cellular nucleus within the unclassified slide image of a tissue;
    extracting a feature from the detected hematoxylin channel, wherein the feature represents a property of the nucleus within the binary slide image and comprises at least one of an area of the nucleus, a perimeter of the nucleus, an integrated density of the nucleus, or a circularity of the nucleus;
    generating, based on the feature, a feature fingerprint associated with the unclassified slide image, wherein the feature fingerprint is a numerical value calculated from processing the feature;
    co-clustering the feature fingerprint with a first set of fingerprints associated with one or more positive control sets and a second set of fingerprints associated with a negative control set, wherein the positive control set(s) comprises a first set of slide images associated with a pass classification and the negative control set comprises a second set of slide images associated with a fail classification; and
    determining, based on the co-clustering, if the feature fingerprint is associated with the pass classification or the fail classification.

17. The method according to claim 16, wherein the feature fingerprint is capable of determining potency or the quality of the tissue for transplantation into a subject.

18. The method according to claim 17, wherein the tissue is thymus tissue.

19. The method according to claim 18, wherein the tissue is allogeneic cultured postnatal thymus tissue-derived product slices for implantation into a human subject.

20. The method according to claim 19, wherein the human subject is suffering from complete DiGeorge syndrome associated with 22q11.2 deletion; coloboma, heart defect, choanal atresia, growth or mental retardation, genital hypoplasia and ear anomalies or deafness syndrome (CHARGE), or athymia associated with forkhead box protein N1 (FOXN1) deficiency.

21. The method according to claim 17, wherein the feature fingerprint determines potency or quality of the tissue for transplantation into a subject of an unknown tissue by generating feature fingerprints of detected nuclei within slide images in a control library and clustering the slide images based on their corresponding feature fingerprints.

22. The method according to claim 21, wherein the unknown tissue is thymus tissue.

23. The method according to claim 22, where the thymus tissue has been subjected to a culturing process in a thymus organ medium for a period of time to partially deplete the thymus tissue of thymocytes.

24. The method according to claim 23, wherein the period of time is up to 21 days.

25. The method according to claim 23, wherein the period of time is from about 12 to about 21 days.

26. The method according to claim 23, wherein the period of time is from about 5 to about 9 days.

27. The method according to claim 23, wherein the culturing process preserves the functional architecture of the thymic stroma.

28. The method according to claim 27, wherein the thymic stroma comprises thymic epithelial cells and fibroblasts.

29. The method according to claim 16, wherein the tissue is selected from the group consisting of vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

30. The method according to claim 17, wherein the feature fingerprint is generated from measurements comprising numerical values of an area of the detected nucleus, a perimeter of the detected nucleus, an integrated density of the detected nucleus, and a circularity of the detected nucleus.

31. A system for classifying objects within digital images of tissue, comprising:
    means for converting a slide image into a binary slide image, wherein the slide image is selected from a library of control images, wherein each slide image in the library of control images is associated with a pass classification or a fail classification;
    means for detecting a nucleus within the binary slide image;
    means for extracting a feature from the detected nucleus, wherein the feature represents a property of the detected nucleus within the binary slide image and comprises at least one of an area of the detected nucleus, a perimeter of the detected nucleus, an integrated density of the detected nucleus, or a circularity of the detected nucleus;
    means for generating, based on the feature, a feature fingerprint associated with the binary slide image, wherein the feature fingerprint is a numerical value calculated from processing the feature;
    means for incorporating the binary slide image into a cluster wherein the cluster comprises a plurality of images, wherein each of the first plurality of images is associated with a corresponding feature fingerprint, and wherein the incorporating is based on comparing the feature fingerprint with the corresponding feature fingerprint;
    means for applying a cutoff height to the cluster to form a plurality of groups, wherein the cutoff height minimizes a number of groups within the plurality of groups based on multivariate analysis of variance analysis of the cluster;
    means for categorizing a first group within the plurality of groups as a positive control set if the first group comprises first slide images associated with the pass classification; and means for categorizing a second group within the plurality of groups as a negative control set if the second group comprises second slide images associated with the fail classification.

32. The system according to claim 31, wherein the system is capable of determining potency or the quality of a tissue for transplantation into a subject.

33. The system according to claim 32, wherein the tissue is thymus tissue.

34. The system according to claim 33, wherein the thymus tissue is allogeneic cultured postnatal thymus tissue-derived product slices for implantation into a human subject.

35. The system according to claim 34, wherein the human subject is suffering from complete DiGeorge syndrome associated with 22q11.2 deletion; coloboma, heart defect, choanal atresia, growth or mental retardation, genital hypoplasia and ear anomalies or deafness syndrome (CHARGE), or athymia associated with forkhead box protein N1 (FOXN1) deficiency.

36. The system according to claim 31, wherein the system classifies potency or quality of a tissue for transplantation into a subject of an unknown tissue by generating feature fingerprints of detected nuclei within slide images in a control library and clustering the slide images based on their corresponding feature fingerprints.

37. The system according to claim 36, wherein the unknown tissue is thymus tissue.

38. The system according to claim 37, where the thymus tissue has been subjected to a culturing process in a thymus organ medium for a period of time to partially deplete the thymus tissue of thymocytes.

39. The system according to claim 38, wherein the period of time is up to 21 days.

40. The system according to claim 38, wherein the period of time is from about 12 to about 21 days.

41. The system according to claim 38, wherein the period of time is from about 5 to about 9 days.

42. The system according to claim 38, wherein the culturing process preserves the functional architecture of the thymic stroma.

43. The system according to claim 42, wherein the thymic stroma comprises thymic epithelial cells and fibroblasts.

44. The system according to claim 31, wherein the tissue is selected from the group consisting of vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

45. The system according to claim 36, wherein the feature fingerprint is generated from measurements comprising numerical values of an area of the detected nucleus, a perimeter of the detected nucleus, an integrated density of the detected nucleus, and a circularity of the detected nucleus.

46. A classifier, comprising:
means for detecting a hematoxylin channel from the unclassified slide image, wherein the hematoxylin channel is associated with a cellular nucleus within the unclassified slide image of a tissue;
means for extracting a feature from the detected hematoxylin channel, wherein the feature represents a property of the nucleus within the binary slide image and comprises at least one of an area of the nucleus, a perimeter of the nucleus, an integrated density of the nucleus, or a circularity of the nucleus;
means for generating, based on the feature, a feature fingerprint associated with the unclassified slide image, wherein the feature fingerprint is a numerical value calculated from processing the feature;
means for co-clustering the feature fingerprint with a first set of fingerprints associated with a positive control set and a second set of fingerprints associated with a negative control set, wherein the positive control set comprises a first set of slide images associated with a pass classification and the negative control set comprises a second set of slide images associated with a fail classification; and
means for determining, based on the co-clustering, if the feature fingerprint is associated with the pass classification or the fail classification.

47. The classifier according to claim 46, wherein the system is capable of determining potency or the quality of a tissue for transplantation into a subject.

48. The classifier according to claim 47, wherein the tissue is thymus tissue.

49. The classifier according to claim 48, wherein the thymus tissue is allogeneic cultured postnatal thymus tissue-derived product slices for implantation into a human subject.

50. The classifier according to claim 49, wherein the human subject is suffering from complete DiGeorge syndrome associated with 22q11.2 deletion; coloboma, heart defect, choanal atresia, growth or mental retardation, genital hypoplasia and ear anomalies or deafness syndrome (CHARGE), or athymia associated with forkhead box protein N1 (FOXN1) deficiency.

51. The classifier according to claim 46, wherein the system classifies potency of an unknown tissue by generating feature fingerprints of detected nuclei within slide images in a control library and clustering the slide images based on their corresponding feature fingerprints.

52. The classifier according to claim 51, wherein the unknown tissue is thymus tissue.

53. The classifier according to claim 52, where the thymus tissue has been subjected to a culturing process in a thymus organ medium for a period of time to partially deplete the thymus tissue of thymocytes.

54. The classifier according to claim 53, wherein the period of time is up to 21 days.

55. The classifier according to claim 53, wherein the period of time is from about 12 to about 21 days.

56. The classifier according to claim 53, wherein the period of time is from about 5 to about 9 days.

57. The classifier according to claim 53, wherein the culturing process preserves the functional architecture of the thymic stroma.

58. The classifier according to claim 57, wherein the thymic stroma comprises thymic epithelial cells and fibroblasts.

59. The classifier according to claim 46, wherein the tissue is selected from the group consisting of vascular tissue, skin tissue, hepatic tissue, pancreatic tissue, neural tissue, urogenital tissue, gastrointestinal tissue, skeletal tissue including bone and cartilage, adipose tissue, connective tissue including tendons and ligaments, amniotic tissue, chorionic tissue, dura, pericardia, muscle tissue, glandular tissue, facial tissue, ophthalmic tissue.

60. The classifier according to claim 46, wherein the feature fingerprint is generated from measurements comprising numerical values of an area of the detected nucleus, a perimeter of the detected nucleus, an integrated density of the detected nucleus, and a circularity of the detected nucleus.

* * * * *